(12) United States Patent
Shiao et al.

(10) Patent No.: US 10,610,576 B2
(45) Date of Patent: Apr. 7, 2020

(54) PRECISION GLYCOCONJUGATES AS THERAPEUTIC TOOLS

(71) Applicant: KORANEX CAPITAL, Montreal (CA)

(72) Inventors: Tze Chieh Shiao, Montreal (CA); Rene Roy, Terrebonne (CA)

(73) Assignee: Koranex Capital, Montreal (CA)

( * ) Notice: Subject to any disclaimer, the term of this patent is extended or adjusted under 35 U.S.C. 154(b) by 0 days.

(21) Appl. No.: 16/362,363

(22) Filed: Mar. 22, 2019

(65) Prior Publication Data

US 2019/0290746 A1 Sep. 26, 2019

Related U.S. Application Data

(60) Provisional application No. 62/647,151, filed on Mar. 23, 2018.

(51) Int. Cl.
*A61K 39/00* (2006.01)
*A61P 35/00* (2006.01)

(52) U.S. Cl.
CPC ...... *A61K 39/001169* (2018.08); *A61P 35/00* (2018.01); *A61K 2039/6037* (2013.01); *A61K 2039/627* (2013.01)

(58) Field of Classification Search
None
See application file for complete search history.

(56) References Cited

U.S. PATENT DOCUMENTS

| | | | | |
|---|---|---|---|---|
| 4,727,136 A * | 2/1988 | Jennings | ............ | A61K 39/0258 424/197.11 |
| 6,765,091 B1 * | 7/2004 | Bencomo | ............. | A61K 39/102 536/1.11 |
| 9,950,054 B2 * | 4/2018 | Gu | ........................ | A61K 39/095 |
| 10,392,420 B2 * | 8/2019 | Han | .................... | A61K 47/6415 |
| 10,429,388 B2 * | 10/2019 | Elsemore | ......... | G01N 33/56966 |
| 2002/0055168 A1 * | 5/2002 | Smith | .................... | A61K 39/092 435/320.1 |
| 2017/0189549 A1 * | 7/2017 | Helin | ................. | A61K 41/0095 |
| 2018/0110876 A1 * | 4/2018 | Sun | ..................... | C07F 9/65583 |
| 2018/0271769 A1 * | 9/2018 | Ghandi | ................. | A01N 25/10 |
| 2019/0224310 A1 * | 7/2019 | Porro | ................... | A61K 39/092 |
| 2019/0330265 A1 * | 10/2019 | Han | ..................... | A61K 39/092 |

FOREIGN PATENT DOCUMENTS

| | | | | |
|---|---|---|---|---|
| WO | WO-2012069168 A2 * | 5/2012 | ......... | B24B 13/0055 |
| WO | WO-2012069188 A1 * | 5/2012 | ............ | C08B 37/00 |
| WO | WO-2015189478 A1 * | 12/2015 | ......... | A61K 41/0095 |
| WO | WO-2016147031 A2 * | 9/2016 | .......... | C07F 9/65583 |

OTHER PUBLICATIONS

Ada et al, Clin. Microbiol. Infect., 2003, 9:79-85. (Year: 2003).*
Borman et al, C&EN:Coverstory-Carbohydrate Vaccines, Aug. 9, 2004, 82/32:31-35 (Year: 2004).*
Haung et al, PNAS, USA, Feb. 13, 2013, 110/7:2517-2522 (Year: 2013).*
Costantino et al, Expert Opin. Drug Discov., 2011, 6/10:1045-1066 (Year: 2011).*
Jaurigue et al, Frontiers in Cellular and Infection Microbiology, Jun. 2017, vol. 7: Article 248. published Jun. 12, 2017 (Year: 2017).*
Weyant et al, Current Opinion in Chemical Engineering, 2018, 19:77-85. available online: Jan. 11, 2018 (Year: 2018).*
Zhu et al, Expert Rev. Vaccines, Oct. 2009, 8/10:1399-1413. (Year: 2009).*
Pichichero, Human Vaccines and Immunotherapeutics, Dec. 2013, 9/12:2505-2523 (Year: 2013).*
Cipolla et al. (1999) "Stereoselective synthesis of α-C-glycosides of N-acetylgalactosamine" Tetrahedron: Asymmetry, 11: 295-303.
Cui et al. (1998) "Stereocontrolled allylation of 2-amino-2-deoxy sugar derivatives by a free-radical procedure" Carbohydrate research, 309: 319-330.
Danishefsky et al. (2015) "Development of Globo-H Cancer Vaccine" ACS Pub. 48: 643-652.
Demian et al. (2014) "Direct targeted glycation of the free sulfhydryl group of cysteine residue (Cys-34) of BSA. Mapping of the glycation sites of the anti-tumor Thomsen-Friedenreich neoglycoconjugate vaccine prepared by Michael addition reaction" Mass Spec. 49: 1223-1233.
Dondoni et al. (2009) "A New Ligation Strategy for Peptide and Protein Glycosylation: Photoinduced Thiol-Ene Coupling" Chem. Euro J. 15: 11444-11449.
Dondoni et al. (2012) "Recent applications of thiol-ene coupling as a click process for glycoconjugation" Chem. Soc. Rev. 41: 573-586.
Feng et al. (2004) "Chemo-enzymatic synthesis of fluorinated 2-N-acetamidosugar nucleotides using UDP-GlcNAc pyrophosphorylase" Org. Biomol. Chem, 2: 1617-1623.
Heimburg et al. (2006) "Inhibition of Spontaneous Breast Cancer Metastasis by Anti—Thomsen-Friedenreich Antigen Monoclonal Antibody JAA-F11" 8;11: 939-948.
Knapp et al. (2002) "Synthesis of a-GalNAc Thioconjugates from an a-GalNAc Mercaptan" J. Org Chem. 67: 2995-2999.
Papadopoulos et al. (2012) "Diazo Transfer and Click Chemistry in the Solid Phase Syntheses of Lysine-Based Glycodendrimers as Antagonists against *Escherichia coli* FimH" Mol. Pharm. 9: 394-403.
Rittenhouse-Diakun et al. (1998) "Development and Characterization of Monoclonal Antibody to T-Antigen: (Galβ1—3GalNAc-α-O)" Hybridoma, 165-173.
Tati et al. (2017) "Humanization of JAA-F11, a Highly Specific Anti-Thomsen-Friedenreich Pancarcinoma Antibody and InVitro Efficacy Analysis" NepPlasia 19: 716-733.
Chemistry: A European Journal, Supporting Information, A New Ligation Strategy for Peptide and Protein Glycosylation: Photoinduced Thiol-Ene Coupling, Dondoni, et al., (2009) pp. 1-36.

* cited by examiner

*Primary Examiner* — Nita M. Minnifield

(74) *Attorney, Agent, or Firm* — Edward J. Baba; Bozicevic, Field & Francis LLP

(57) ABSTRACT

The present description relates to glycoconjugates, glycoconjugate immunogens and glycoconjugate vaccines comprising carbohydrate antigens coupled to immunogenic carrier proteins, or materials used for detection and screening of resulting antibodies. Improved methods of more directly and precisely conjugating carbohydrate antigens to free thiol groups of immunogenic carrier proteins are described, including "click-chemistry" approaches based on photocatalytic thiol-ene reactions.

20 Claims, 51 Drawing Sheets

Specification includes a Sequence Listing.

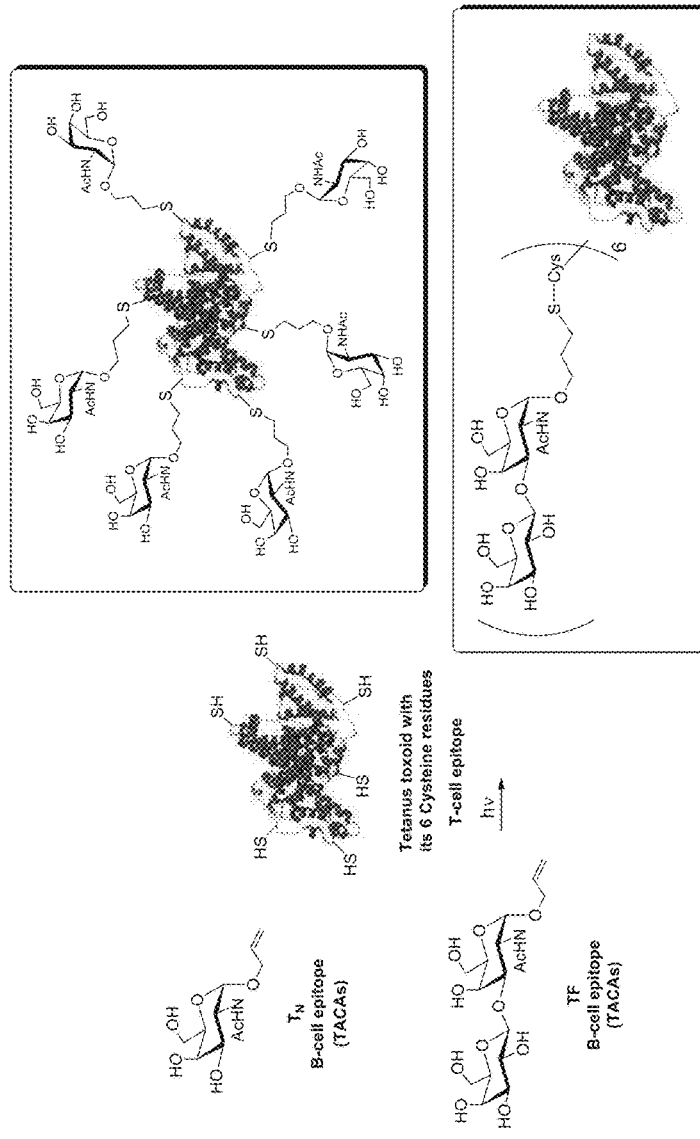

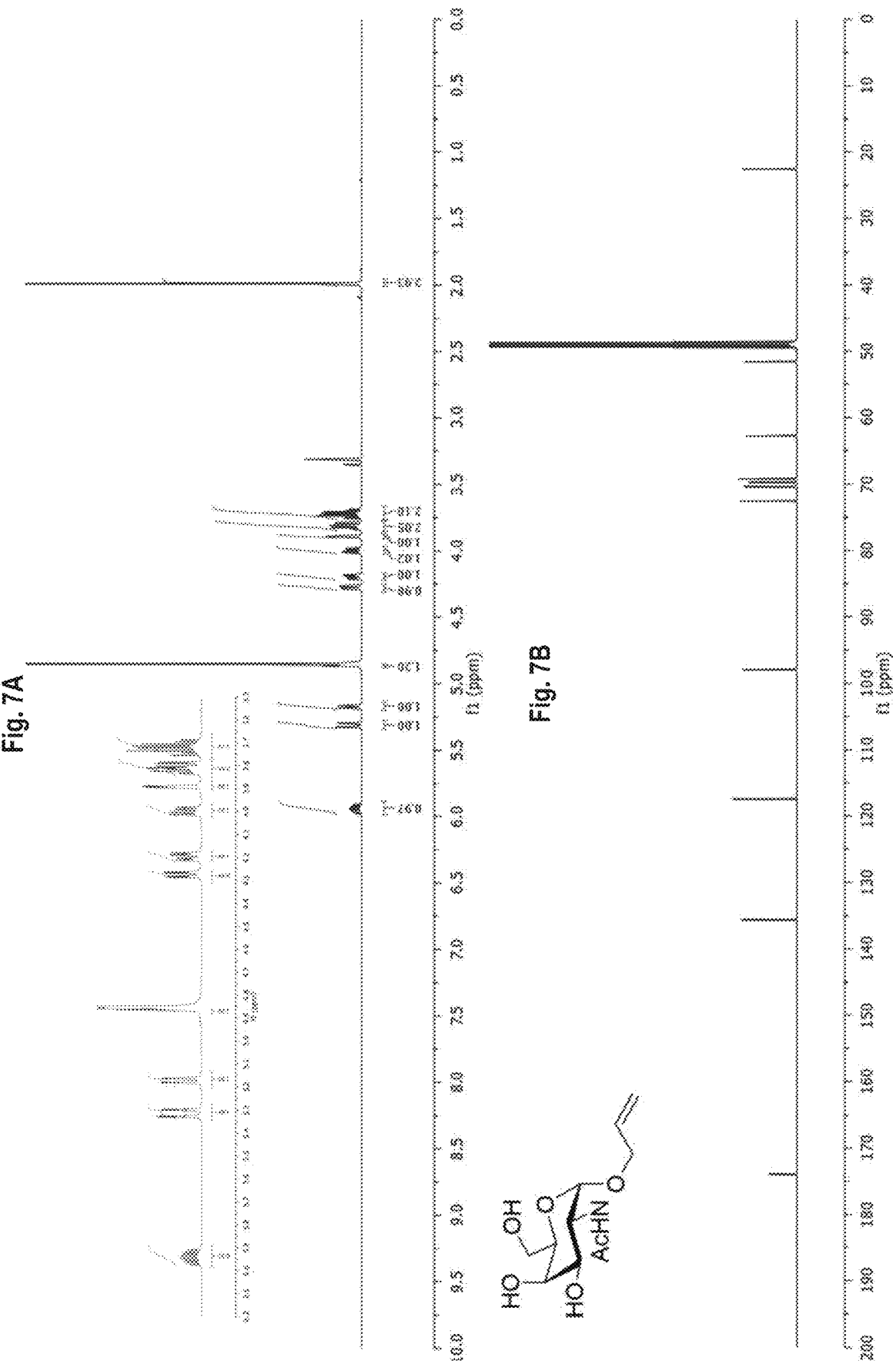

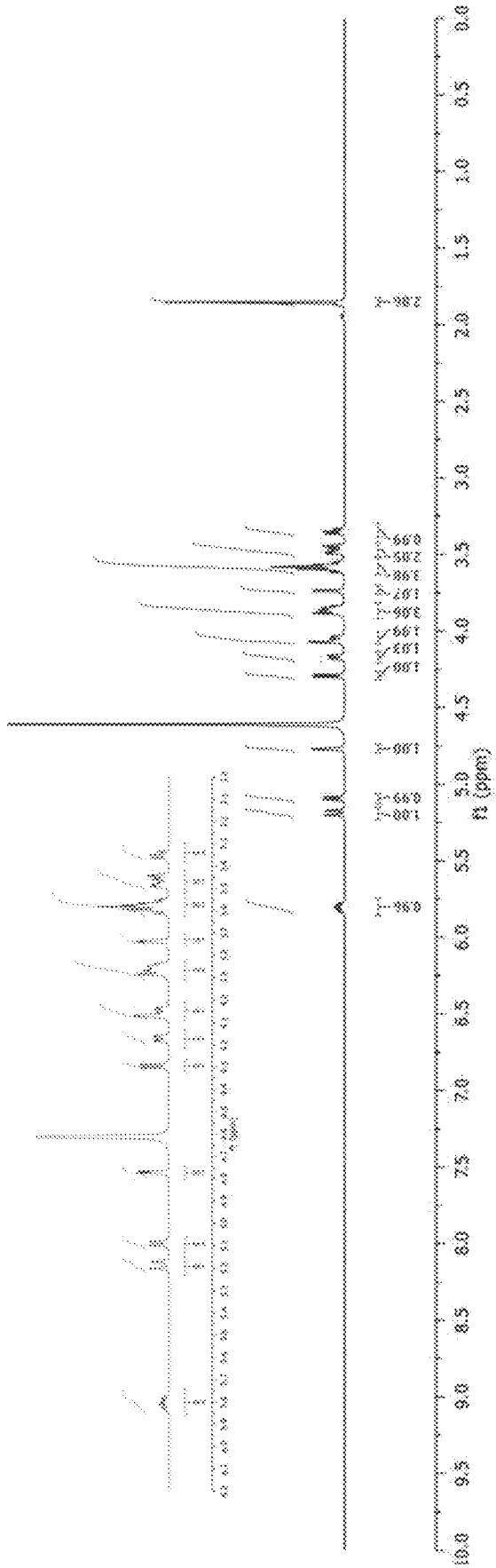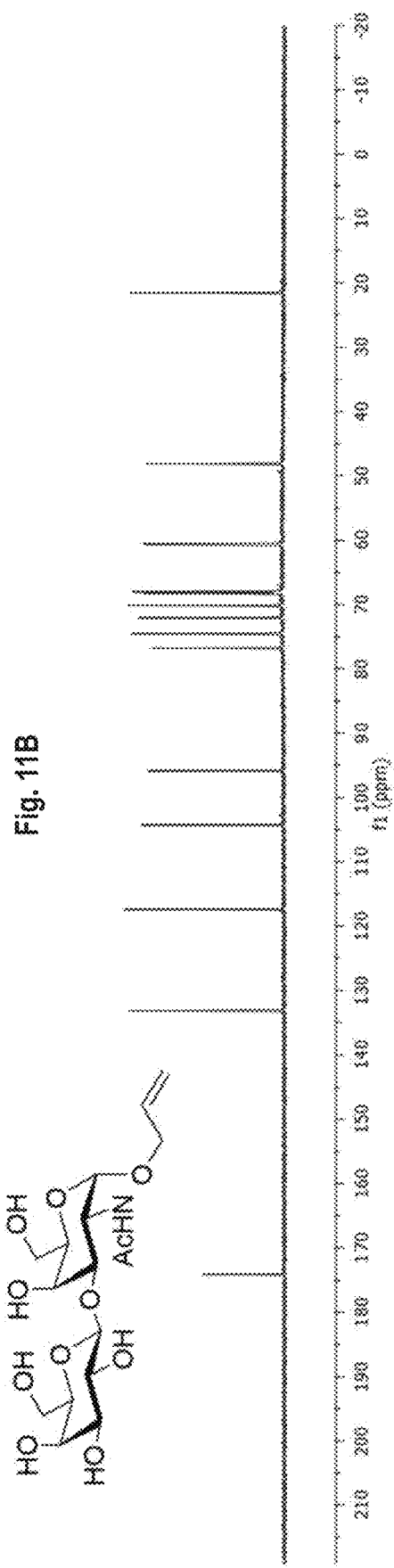
Fig. 11A
Fig. 11B

Fig. 34
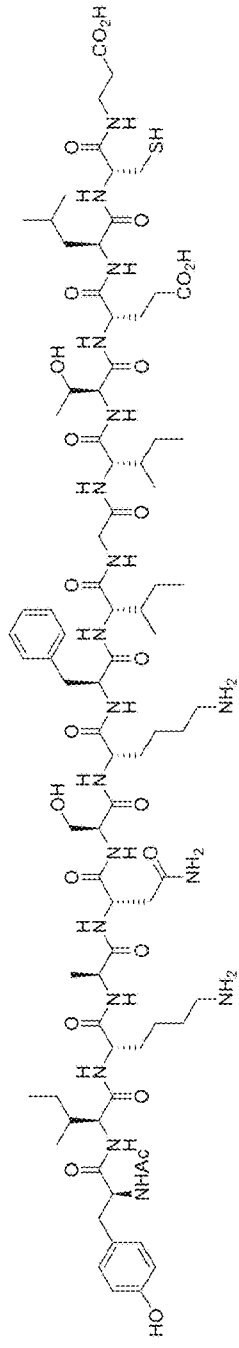
dTT831-844-Cys-βAla
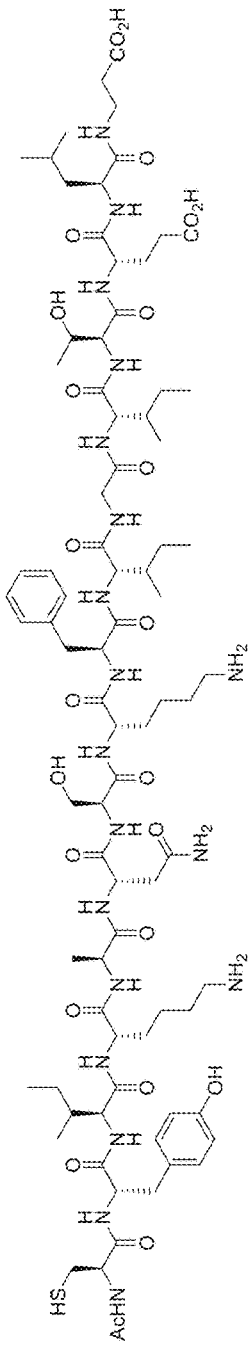
Cys-dTT831-844-βAla
Compound Table
| Compound Label | Data File | RT | Mass | Abund | Formula | Tgt Mass | Diff (ppm) |
|---|---|---|---|---|---|---|---|
| Cpd 1: C83 H133 N19 O24 S | Roy_Chichi_181019_STC-GV-III-023_LC_5-95-10_UV_10ul.d | 5.32 | 1811.9521 | 211331 | C83 H133 N19 O24 S | 1811.9492 | 1.59 |
| Cpd 1: C83 H133 N19 O24 S | Roy_Chichi_181019_STC-GV-____LC_5-95-10_UV_10ul.d |  | 1811.9526 | 331559 | C83 H133 N19 O24 S | 1811.9492 | 1.88 |

Fig. 37
dTT831-844-Cys-βAla-O-Tn
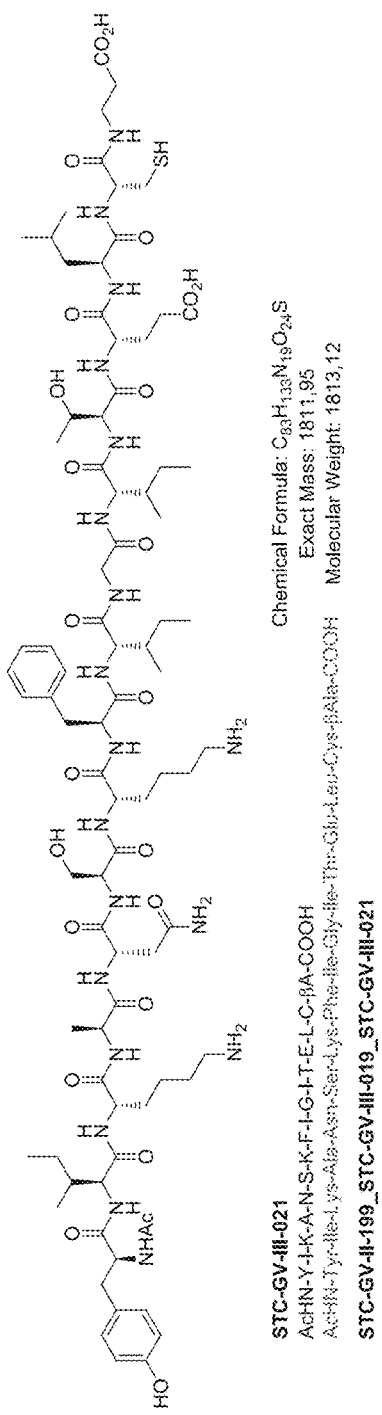
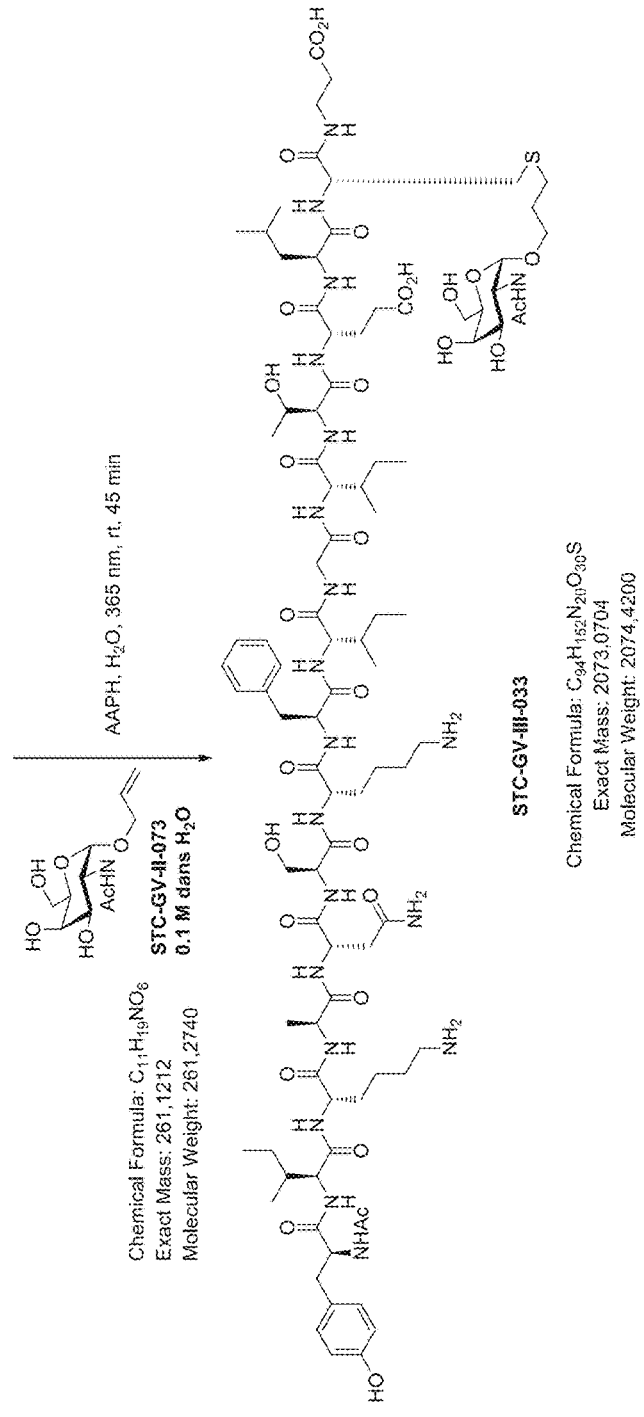

dTT831-844-Cys-βAla-O-Tn

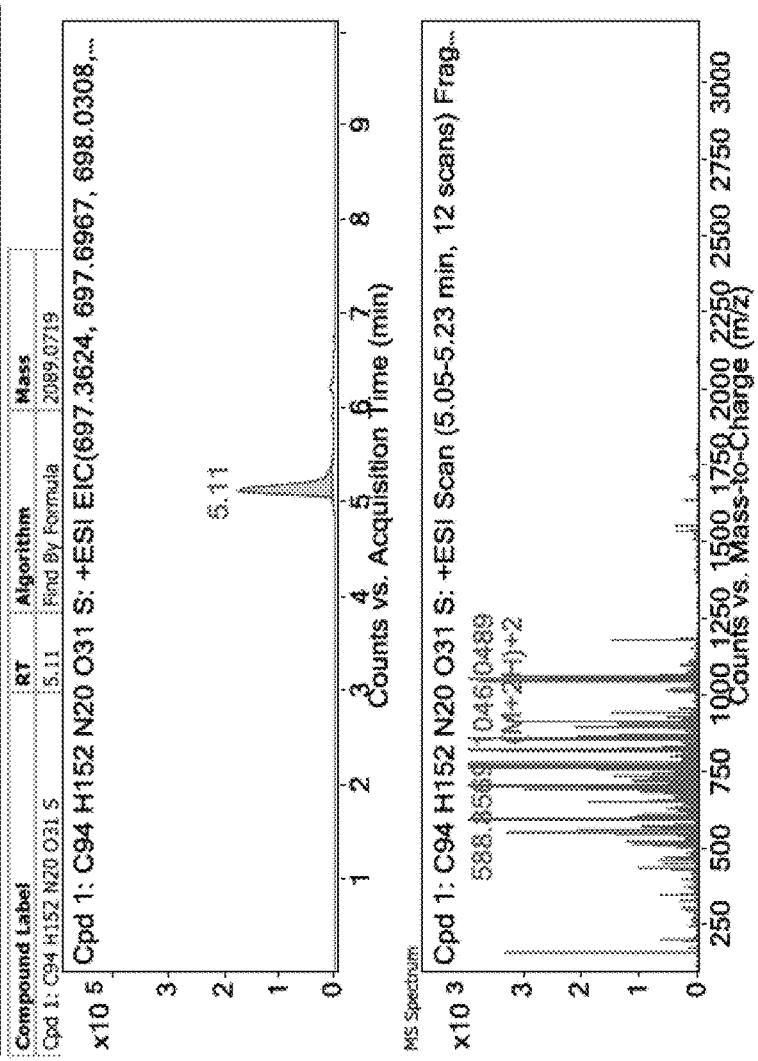

PRECISION GLYCOCONJUGATES AS THERAPEUTIC TOOLS

The present description relates to glycoconjugate therapeutic tools. More specifically, the present description relates to carbohydrate antigens non-randomly coupled to free thiol groups of immunogenic and antigenic carrier peptides and proteins, and improved methods of producing same using, for example, photocatalytic thiol-ene "click chemistry" reactions. Applications as antigens, immunogens, vaccines, and in diagnostics are also described.

The present description refers to a number of documents, the content of which is herein incorporated by reference in their entirety.

BACKGROUND

The ultimate objective of immunotherapy is to trigger the innate and adaptive responses of the immune system in a way similar to that produced during an infection or tumor progression. The principal interfaces between the innate and adaptive immune responses are the antigen-presenting cells (APCs), and particularly dendritic cells (DCs). APCs are able to recognize microorganisms through pattern recognition receptors (PRRs) such as Toll-like receptors (TLRs). On recognition of microbial surface determinants or aberrant and unnatural antigens, APCs undergo maturation and activation leading to a redistribution of MHC molecules from intracellular compartments to the cell surface, secretion of cytokines and chemokines. The microorganisms or tumors and their related antigenic markers can be engulfed by the APC through an endocytic pathway where it is typically degraded. The peptides and covalently linked antigens released by protein processing are then displayed on MHC class II molecules and are recognized by CD4+ T cells which in turn undergo functional maturation into different subsets, such as Th1 or Th2 cells, upon co-stimulatory signals received from the APC. Th1 cells lead to a predominantly pro-inflammatory response with the secretion of IFN-γ and TNF-α, whereas Th2 cells secrete typical cytokines. Albeit Th1 cells are mainly associated with a cell-mediated response, both types of Th cells support the production of antibodies by B cells, which in turn influences antibody isotype and function. For example, IL-12 and TNF-α are associated with the differentiation of Th1 cells and production of type 1 IgG subclasses, whereas IL-6 and other Th2 cytokines contribute to the type 2 IgG subclass (IgG1) production. It is thus desirable to be able to tailor vaccine-induced immunity to an appropriate response to deal with a pathogen or tumor antigen of interest.

Carbohydrates, as opposed to proteins and peptides, are T cell independent antigens not properly equipped to trigger the participation of Th cells and hence, cannot induce immune cell proliferation, antibody class switching, and affinity/specificity maturation. The major early advances initially encountered with carbohydrate-based vaccines have been supported by the discovery that, when properly conjugated to protein carriers, serving as T cell dependent epitopes, bacterial capsular polysaccharides became capable of acquiring the requisite immunochemical ability to produce opsonophagocytic antibodies.

Traditionally, strategies for conjugating carbohydrate antigens to carrier proteins have relied on either reductive amination of aldehyde-derived sugars onto the ε-amino groups of the lysine residues, or simply amide coupling reactions. In both cases, partial and random carbohydrate antigen conjugation generally occurs. Furthermore, if all amide partners (amines from lysine or acid from glutamic/aspartic acids) are used for carbohydrate conjugation, far too many carbohydrate antigens become attached to the carrier proteins, thus resulting in masking potentially essential T cell peptide epitopes with the inherent diminution/elimination of immunogenicity. Thus, current strategies for preparing glycoconjugate vaccines are inadequate and face significant regulatory and/or commercial obstacles, since the preparations lack the necessary homogeneity in terms of their carbohydrate distribution and reproducibility (i.e., the attachment points of the sugars onto the proteins are randomly distributed and in various densities from batch to batch). Thus, glycoconjugate vaccines having greater carbohydrate antigen homogeneity, more precisely characterizable structures, and reproducibility from batch to batch would be highly desirable.

SUMMARY

The present description relates to glycoconjugate immunogens comprising carbohydrate antigens directly coupled to immunogenic carrier proteins at precise (non-random) positions. More particularly, the carrier proteins comprise one or more free thiol groups (e.g., corresponding to the side chains of cysteine residues) and the carbohydrate antigens are conjugated to the carrier proteins at one or more of these free thiol groups. The present description also relates to improved methods for synthesizing glycoconjugate immunogens/vaccines involving directly conjugating carbohydrate antigens to free thiol groups of carrier proteins, for example using "click-chemistry" approaches (e.g., photocatalytic thiol-ene reactions). The improved conjugation methods described herein may be performed under conditions sufficiently mild (e.g., use of only water-soluble reagents, the absence of organic solvents, or use concentrations of organic solvents sufficiently low (e.g., <5%) to avoid carrier protein denaturation, and/or at relatively neutral pH) to avoid destroying the activity, antigenicity, and/or structure (e.g., cleavage of native disulfide bridges and/or denaturation) of a carrier protein, without affecting the specificity of the conjugation. Furthermore, photocatalytic thiol-ene reactions described herein may be performed under ultraviolet light in the presence of a catalyst (e.g., 355 nm or 365 nm), or under short-wave ultraviolet light (e.g., at 254 nm) in the absence of a catalyst, further simplifying the process.

In some aspects, the present description relates to a method for producing a glycoconjugate immunogen, the method comprising: (a) providing a carbohydrate antigen covalently linked to a terminal alkene (alkenyl carbohydrate antigen), the terminal alkene being directly conjugatable to a thiol group via a thiol-ene reaction; (b) providing a carrier protein having one or more free thiol groups; and (c) performing a photocatalytic thiol-ene reaction to directly conjugate the carbohydrate antigen to the carrier protein at the one or more free thiol groups, thereby producing the glycoconjugate immunogen; wherein the carrier protein is immunogenic when administered to a subject, and wherein conjugation of the carbohydrate antigen to the carrier protein increases the immunogenicity of the carbohydrate antigen upon administration to the subject, as compared to administration of the unconjugated carbohydrate antigen.

In some embodiments, the photocatalytic thiol-ene reaction is performed under reaction conditions that avoid carrier protein denaturation. In embodiments, the alkenyl carbohydrate antigen is water-soluble and the photocatalytic thiol-ene reaction is performed under reaction conditions that retain the carrier protein's activity, antigenicity, and/or structure (e.g., in the absence of any organic solvent, or in the presence of an organic solvent at a concentration sufficiently low (e.g., <5%) to avoid carrier protein denaturation). The photocatalytic thiol-ene reaction may be performed in the presence of a catalyst (e.g., a water-soluble or water-insoluble catalyst) under irradiation under short-wave (e.g., 254 nm) and/or long-wave (e.g., 355 or 365 nm) ultraviolet light.

In some embodiments, the photocatalytic thiol-ene reaction comprises reacting between 1 to 200 molar equivalents of the alkenyl carbohydrate antigen per free thiol group of the carrier protein; and/or the photocatalytic thiol-ene reaction is performed at a pH between about 3 and 10, 3.5 and 9.5, 4 and 9, 4.5 and 8.5, 5 and 8, 5.5 and 8, 6 and 8, or 6.5 and 7.5.

In some embodiments, the carbohydrate antigen, following conjugation to the carrier protein, is not cleavable from the carrier protein by an endogenous enzyme of the subject. In some embodiments, the alkenyl carbohydrate antigen is covalently linked to the terminal alkene, and/or the carbohydrate antigen is conjugated to the carrier protein, via a glycosidic bond, such as is an O-glycosidic bond, an S-glycosidic bond, an N-glycosidic bond, or a C-glycosidic bond, or a bond obtained by reductive amination, such as between an allyl amine and a reducing sugar (including bacterial CPS). In some embodiments, the carbohydrate antigen comprises a B cell epitope, and/or induces a humoral immune response in the subject. In some embodiments, the carbohydrate antigen comprises a T cell epitope, and/or induces a cell-mediated immune response in the subject. In some embodiments, the carbohydrate antigen comprises both a B cell epitope and a T cell epitope, and/or induces both a humoral and a cell-mediated immune response in the subject. In some embodiments, the carbohydrate antigen is or comprises a tumor associated carbohydrate antigen (TACA), such as Tn, S-Tn, Thomsen-Friedenreich (TF), (2,3)-S-TF, (2,6)-S-TF, Globo H, GD2, GD3, GM2, GM3, N-glycolyl-GM3, Lea, sLea, Lex, sLex, or any combination thereof. In some embodiments, the photocatalytic thiol-ene reaction conjugates at least two of the same carbohydrate antigen or more than one type of carbohydrate antigen to the carrier protein, thereby producing a multi-valent glycoconjugate immunogen (e.g., comprising 2, 3, 4, 5, 6, 7, 8, 9, 10, 11, 12, 13, 14, 15, or more of the same or different types of carbohydrate antigens conjugated to the carrier protein). In some embodiments, the carbohydrate antigen is or comprises a viral polysaccharide antigen, or a bacterial capsular polysaccharide (CPS) (e.g., a Pneumococcal and/or Streptococcal polysaccharide serotype, meningococcal CPS; influenza (such as influenza type a or b) CPS).

In some embodiments, the alkenyl carbohydrate antigen is linked to the terminal alkene via a linker (e.g., a linker as described herein).

In some embodiments, the carrier protein comprises one or more cysteine residues having the one or more free thiol groups. In some embodiments, the carrier protein comprises a T cell epitope, and/or induces a cell-mediated immune response in the subject.

In some embodiments, the carrier protein comprises a B cell epitope, and/or induces a humoral immune response in the subject. In some embodiments, the carrier protein comprises both a B cell epitope and a T cell epitope, and/or induces both a humoral and a cell-mediated immune response in the subject. In some embodiments, the carrier protein is, is from, or comprises: Tetanus Toxoid (TT), Diphtheria Toxoid (DT), cross-reacting material 197 (CRM197), Meningococcal Outer Membrane Protein Complex (OMPC), *H. influenzae* Protein D (HiD), a virus-like particle (VLP), a cytokine, an immunogenic peptide such as Tetanus Toxin 831-844 (SEQ ID NO: 1 or 2), albumin (such as bovine serum albumin or human serum albumin), or an immunogenic fragment thereof. In some embodiments, the carrier protein is a protein having one or more disulfide bridges, and wherein: (i) the one or more disulfide bridges remain unaffected following said photocatalytic thiol-ene reaction; or (ii) the carrier protein is pre-treated with a reducing agent to expose one or more additional free thiol groups for conjugation to the carbohydrate antigen.

In some embodiments, the total number of carbohydrate antigens comprised in the glycoconjugate immunogen is equal to the number of free thiol groups available on the carrier protein prior to conjugation. In some embodiments, the glycoconjugate immunogen induces a cell-mediated immune response to the carbohydrate antigen upon administration to the subject.

In some embodiments, the methods described herein further comprise: (d) purifying the glycoconjugate immunogen.

In some aspects, the present description relates to a method for producing a glycoconjugate vaccine, the method comprising formulating the glycoconjugate immunogen prepared by a method described herein with a pharmaceutically acceptable excipient, and/or an adjuvant (e.g., an inorganic compound, a mineral oil, a microbial derivative, a plant derivative, a cytokine, squalene, alum, aluminum hydroxide, aluminum phosphate, calcium phosphate hydroxide, a toll-like receptor agonist, an immunostimulatory polynucleotide (e.g., CPG), an immunostimulatory lipid, Freund's adjuvant, RIBI's adjuvant, QS-21, muramyl dipeptide, or any combination thereof).

In some aspects, the present description relates to a synthetic glycoconjugate immunogen comprising one or more carbohydrate antigens and an immunogenic carrier protein having one or more solvent-accessible cysteine residues, wherein the one or more carbohydrate antigens are linked to the immunogenic carrier protein at the one or more solvent-accessible cysteine residues, and wherein conjugation of the one or more carbohydrate antigens to the immunogenic carrier protein increases the immunogenicity of the one or more carbohydrate antigens upon administration to a subject, as compared to administration of the unconjugated carbohydrate antigen. In some embodiments, the one or more carbohydrate antigens are linked to the one or more solvent-accessible cysteine residues via a linker as described herein and the one or more carbohydrate antigens is/are as described herein. In some embodiments, the synthetic glycoconjugate immunogen is a multi-valent glycoconjugate immunogen as described herein, and uses a carrier protein as described herein. In some embodiments, the total number of carbohydrate antigens comprised in the glycoconjugate immunogen is equal to the number of solvent-accessible cysteine residues on the carrier protein. In some embodiments, the synthetic glycoconjugate immunogen induces a cell-mediated immune response to the carbohydrate antigen upon administration to the subject. In some embodiments, the synthetic glycoconjugate immunogen is prepared by a method described herein.

In some aspects, the present description relates to a glycoconjugate vaccine produced by a method as described herein, and/or comprising the synthetic glycoconjugate immunogen as described herein, and a pharmaceutically acceptable excipient, and/or an adjuvant. In some embodiments, the glycoconjugate vaccine is a prophylactic vaccine or a therapeutic vaccine.

In some aspects, the present description relates to a method of immunizing, vaccinating, or treating a subject comprising administering to the subject the glycoconjugate immunogen produced by a method as described herein, the glycoconjugate vaccine produced by a method as described herein, a synthetic glycoconjugate immunogen as described herein, or a glycoconjugate vaccine as described herein. In some embodiments, the present description relates to a synthetic glycoconjugate immunogen or a glycoconjugate vaccine as described herein, for use in immunizing, vaccinating, or treating a subject having a disease, or for detecting the presence of an antibody that specifically binds to the glycoconjugate, or for detecting said immunization, vaccination, or treatment (e.g., in a biological sample from a subject).

In some aspects, the present description relates to a synthetic glycoconjugate immunogen comprising one or more sugar antigens covalently linked to one or more free thiol groups of a carrier protein via a linker, wherein the synthetic glycoconjugate immunogen has the structure:

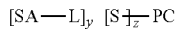

wherein
y is at least 1;
SA is selected from the group consisting of sugar antigens or immunogenic portions thereof, and when y is more than 1, SA are identical or different;
$[S]_z$—PC is a carrier protein having one or more sulfur atoms originating from the one or more free thiol groups;
z is at least 1 and is at least equal to y; and
L is a linker selected from the group consisting of linkers having the structure:

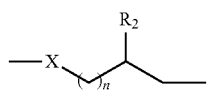

wherein:
X is O, S, $NR_1$, or $CH_2$;
$R_1$ is —H, —COH, —$COCH_3$, or —COEt;
n is 1, 2, 3, 4, or 5; and
$R_2$ is H or Me; and
when y is more than 1, L are identical or different;
or a stereoisomer thereof.

In some aspects, the present description relates to a synthetic glycoconjugate immunogen comprising one or more sugar antigens covalently linked to one or more free thiol groups of a carrier protein via a linker, wherein the synthetic glycoconjugate immunogen has the structure:

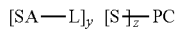

wherein
y is at least 1;
SA is selected from the group consisting of sugar antigens or immunogenic portions thereof, and when y is more than 1, SA are identical or different;
$[S]_z$—PC is a carrier protein having one or more sulfur atoms originating from the one or more free thiol groups;
z is at least 1 and is at least equal to y; and
L is a linker selected from the group consisting of linkers having the structure:

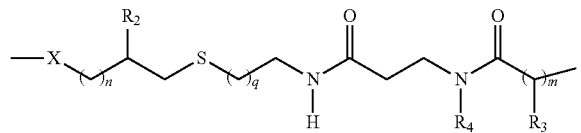

wherein:
X is S, $NR_1$, $CH_2$ or O;
$R_1$ is —H, —COH, —COMe, or —COEt;
n is 1, 2, 3, 4, or 5;
$R_2$ is H or Me;
q is 1, 2, 3, 4, or 5;
$R_3$ and $R_4$ are each a hydrogen atom and m is 1, 2, 3, 4 or 5, or $R_3$ and $R_4$ form together a radical —CO—$CH_2$— or a radical —CO—$CH_2$—$CH_2$— with the carbonyl linked to the nitrogen atom, and m is 1; and
when y is more than 1, L are identical or different;
or a stereoisomer thereof.

In some aspects, the present description relates to a synthetic glycoconjugate immunogen comprising one or more sugar antigens covalently linked to one or more free thiol groups of a carrier protein via a linker, wherein the synthetic glycoconjugate immunogen has the structure:

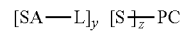

wherein
y is at least 1;
SA is selected from the group consisting of sugar antigens or immunogenic portions thereof, and when y is more than 1, SA are identical or different;
$[S]_z$—PC is a carrier protein having one or more sulfur atoms originating from the one or more free thiol groups;
z is at least 1 and is at least equal to y; and
L is a linker selected from the group consisting of linkers having the structure:

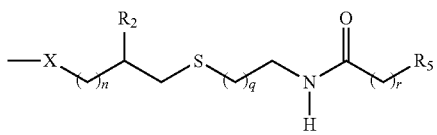

wherein
X is S, $NR_1$, $CH_2$ or O;
$R_1$ is —H, —COH, —COMe, or —COEt;
n is 1, 2, 3, 4, or 5;
$R_2$ is H or Me;
q is 1, 2, 3, 4, or 5;
r is 1, 2, 3, 4 or 5;

$R_5$ is S—PC, a covalent bond, or a radical of structure:

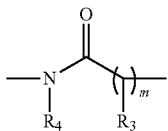

wherein $R_3$ and $R_4$ are each a hydrogen atom and m is 1, 2, 3, 4 or 5, or $R_3$ and $R_4$ form together a radical —CO—CH$_2$— or a radical —CO—CH$_2$—CH$_2$— with the carbonyl linked to the nitrogen atom, and m is 1; and when y is more than 1, L are identical or different;

or a stereoisomer thereof.

In some embodiments, the present description relates to the synthetic glycoconjugate immunogen as defined above, wherein the linker has the structure:

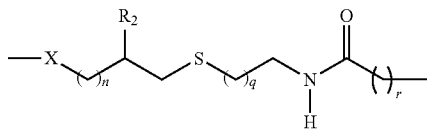

wherein
X is S, NR$_1$, CH$_2$ or O;
$R_1$ is —H, —COH, —COMe, or —COEt;
n is 1, 2, 3, 4, or 5;
$R_2$ is H or Me;
q is 1, 2, 3, 4, or 5; and
r is 1, 2, 3, 4 or 5.

In some embodiments, the present description relates to the synthetic glycoconjugate immunogen as defined above, wherein the linker has the structure:

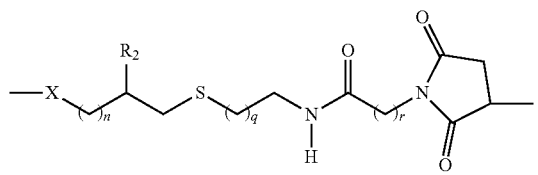

wherein
X is S, NR$_1$, CH$_2$ or O;
$R_1$ is —H, —COH, —COMe, or —COEt;
n is 1, 2, 3, 4, or 5;
$R_2$ is H or Me;
q is 1, 2, 3, 4, or 5; and
r is 1 or 2.

In some embodiments, the present description relates to the synthetic glycoconjugate immunogen as defined above, wherein the linker has the structure:

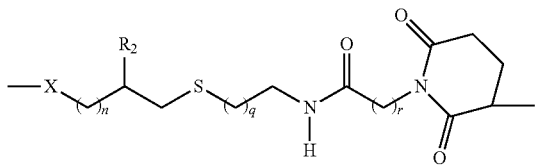

wherein
X is S, NR$_1$, CH$_2$ or O;
$R_1$ is —H, —COH, —COMe, or —COEt;
n is 1, 2, 3, 4, or 5;
$R_2$ is H or Me;
q is 1, 2, 3, 4, or 5; and
r is 1 or 2.

In some embodiments, the present description relates to the synthetic glycoconjugate immunogen as designed above, wherein y is an integer varying from 1 to 50, 1 to 40, 1 to 30, 1 to 20, 1 to 10, 1 to 5, or 1 to 3.

In some aspects, the present description relates to a synthetic glycoconjugate immunogen comprising one or more sugar antigens covalently linked to one or more free thiol groups of a carrier protein via a linker, wherein each linker has the structure:

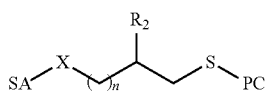

wherein: SA is a sugar antigen or a portion thereof; S—PC is a carrier protein; X is O, S, NR$_1$, or CH$_2$; $R_1$ is —H, —COH, —COCH$_3$, or —COEt; n is 1, 2, 3, 4, or 5; and $R_2$ is H or Me; or a stereoisomer thereof.

In some aspects, the present description relates to a synthetic glycoconjugate immunogen comprising one or more sugar antigens covalently linked to one or more free thiol groups of a carrier protein via a linker, wherein each linker has the structure:

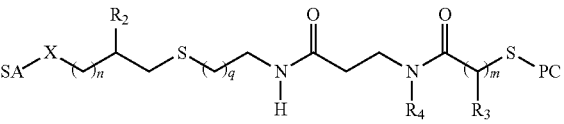

wherein: SA is a sugar antigen or a portion thereof; S—PC is a carrier protein; X is S, NR$_1$, CH$_2$ or O; $R_1$ is —H, —COH, —COMe, or —COEt; n is 1, 2, 3, 4, or 5; $R_2$ is H or Me; q is 1, 2, 3, 4, or 5; $R_3$ and $R_4$ are each a hydrogen atom and m is 1, 2, 3, 4 or 5, or $R_3$ and $R_4$ form together a radical —CO—CH$_2$— or a radical —CO—CH$_2$—CH$_2$— with the carbonyl linked to the nitrogen atom, and m is 1; or a stereoisomer thereof.

In some embodiments, the sugar antigen is a carbohydrate antigen as described herein, the carrier protein is as described herein, the synthetic glycoconjugate immunogen is a multi-valent glycoconjugate immunogen as described herein.

In some aspects, the present description relates to a vaccine comprising the synthetic glycoconjugate immunogen as described herein, and a pharmaceutically acceptable excipient and/or an adjuvant as described herein.

In some aspects, the present description relates to the use of the glycoconjugate immunogen prepared by a method as described herein, or a synthetic glycoconjugate immunogen as described herein, for the manufacture of a vaccine.

In some aspects, the present description relates to the use of the glycoconjugate immunogen prepared by a method as described herein, a glycoconjugate vaccine produced by a method as described herein, a synthetic glycoconjugate immunogen as described herein, or a vaccine as described herein, for the treatment of a subject having a disease associated with increased expression of said one or more carbohydrate or sugar antigens.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed in order to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "protein" (e.g., in the expression "carrier protein") means any peptide-linked chain of amino acids, which may or may not comprise any type of modification (e.g., chemical or post-translational modifications such as acetylation, phosphorylation, glycosylation, sulfation, sumoylation, prenylation, ubiquitination, etc.), so long as the modifications do not destroy the immunogenicity of the glycoconjugate immunogens and glycoconjugate vaccines described herein. For further clarity, the terms "protein" and "carrier protein" as used herein encompass both peptides and polypeptides.

As used herein, the term "administration" may comprise administration routes such as parenteral (e.g., subcutaneously, intradermally, intramuscularly, or intravenously), oral, transdermal, intranasal, etc., so long as the route of administration results in the generation of an immune response in the subject.

As used herein, "subject" generally refers to a mammal, including primates, and particularly to a human.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 2 shows a proposed "click chemistry" approach for conjugating a carbohydrate antigen (B cell epitope) directly to an available thiol group of an immunogenic carrier protein (e.g., T cell epitope such as Tetanus Toxoid).

FIG. 3 shows an example of a "precision glycoconjugate" prepared by a photocatalytic thiol-ene reaction to conjugate Tn or TF antigens to six native "free" cysteine residues on the carrier protein Tetanus Toxoid.

FIG. 7A-7D shows the $^1$H-NMR (FIG. 7A) and $^{13}$C-NMR (FIG. 7B) spectra, as well as mass spectrometry results (FIGS. 7C and 7D) for allyl 2-acetamido-2-deoxy-α-D-galactopyranoside (allyl Tn).

FIG. 11A-11D shows the $^1$H-NMR (FIG. 11A) and $^{13}$C-NMR (FIG. 11B) spectra, as well as mass spectrometry results (FIGS. 11C and 11D) for allyl (β-D-galactopyranosyl)-(1→3)-2-acetamido-2-deoxy-α-D-galactopyranoside (allyl TF).

FIG. 34 shows the chemical structures of the dTT831-844-Cys-βAla and the Cys-dTT831-844-βAla with a cysteine residue at the C- and N-terminal, respectively together with their tabulated LC-MS data.

FIG. 37 shows the photolytic AAPH-catalyzed thiol-ene reaction of the O-Allyl Tn on the C-terminal peptide dTT831-844-Cys-βAla.

FIG. 40 shows the LC-MS profile of the O-Allyl Tn on the N-terminal peptide.

SEQUENCE LISTING

Figure 1:
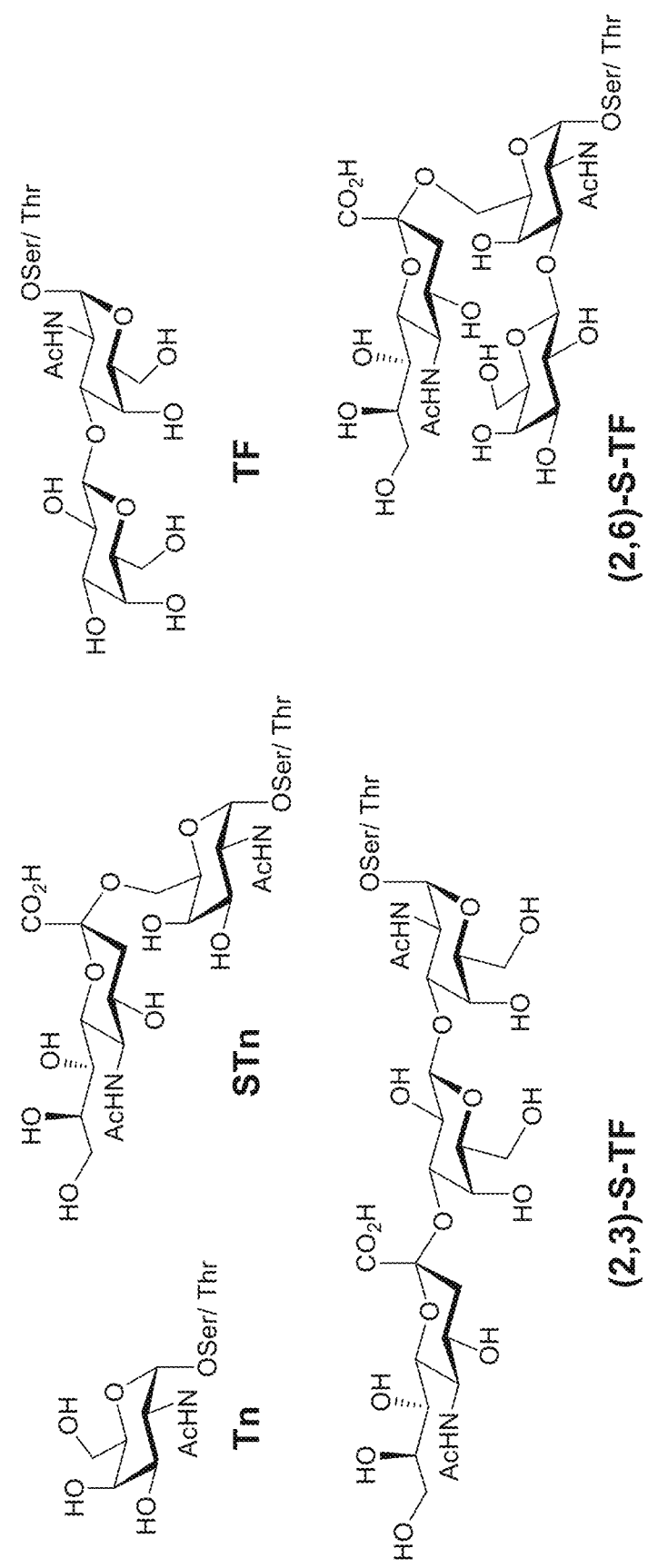
FIG. 1 shows examples of typical chemical structures of key tumor-associated carbohydrate antigens (TACAs) from human glycoproteins (MUCs).

This application contains a Sequence Listing in computer readable form created Mar. 19, 2019 having a size of about 4 KB. The computer readable form is incorporated herein by reference.

DETAILED DESCRIPTION

The present description relates to glycoconjugate immunogens (e.g., for use as vaccines, in diagnostics, or for generating diagnostic or therapeutic tools such as specific anti-glycoconjugate antibodies). The glycoconjugate immunogens described herein generally comprise carbohydrate antigens coupled to immunogenic carrier proteins. More particularly, the carrier proteins comprise one or more free thiol groups (e.g., corresponding to the side chains of cysteine residues) and the carbohydrate antigens are conjugated to the carrier proteins at one or more of these free thiol groups. The present description also relates to improved methods for synthesizing glycoconjugate immunogens/vaccines involving directly conjugating carbohydrate antigens to free thiol groups of carrier proteins, for example using "click-chemistry" approaches (e.g., photocatalytic thiol-ene reactions). The improved conjugation methods described herein may be performed under conditions sufficiently mild (e.g., use of only water-soluble reagents, the absence of organic solvents, use concentrations of organic solvents sufficiently low (e.g., <5%) to avoid carrier protein denaturation, and/or at relatively neutral pH) to avoid destroying the activity, antigenicity, and/or structure (e.g., cleavage of native disulfide bridges and/or denaturation) of a carrier protein, without affecting the specificity of the conjugation. Furthermore, photocatalytic thiol-ene reactions described herein may be performed under ultraviolet light in the presence of a catalyst (e.g., 355 nm or 365 nm), or under short-wave ultraviolet light (e.g., at 254 nm) in the absence of a catalyst, further simplifying the process.

Because of the greater precision offered by the conjugation methods described herein, the glycoconjugate immunogens/vaccines described herein may have greater homogeneity (in terms of their carbohydrate distributions), reproducibility, and may be easier to characterize as compared to glycoconjugates that rely on random coupling to other amino acid side chains (e.g., amines from lysine, or acid from glutamate/aspartate residues). Such characteristics may facilitate regulatory approval and/or commercialization of glycoconjugate vaccines, both of which have historically proven difficult based on traditional approaches.

In some aspects, the present description relates to a method for producing a glycoconjugate immunogen (e.g., for administration to a subject). As used here, the term "subject" generally refers to a living being (e.g., animal or human) that is able to mount an immune response to a glycoconjugate immunogen as described herein, preferably leading to the production of antibodies that specifically bind to the glycoconjugate immunogen. In some embodiments, a subject described herein may be a patient to be treated therapeutically (e.g., via vaccination with a glycoconjugate immunogen described herein) or may be employed as a means for generating tools (e.g., antibodies) for research, diagnostic, and/or therapeutic purposes. The method for producing a glycoconjugate immunogen generally comprises providing a carbohydrate antigen having (e.g., chemically modified to comprise) a thiol-specific functional group; providing a carrier protein having one or more free thiol groups (e.g., one or more solvent-accessible cysteine residues, and/or cysteines not involved in disulfide bridges); and reacting the carbohydrate antigen with the carrier protein, thereby coupling of the carbohydrate antigen to the carrier protein at one or more predictable (non-random) attachment points corresponding to the positions of the free thiol groups of the carrier protein. In some embodiments, the method may further comprise purifying or isolating the glycoconjugate immunogen, which may then be formulated as a vaccine (e.g., comprising an adjuvant).

As used herein, the term "glycoconjugate" refers to a carbohydrate antigen (e.g., an antigenic monosaccharide, di-saccharide, oligo-saccharide, or polysaccharide) coupled to a carrier protein in order to enhance the immunogenicity of carbohydrate antigen in a subject of interest. The expressions "carbohydrate antigen" and "sugar antigen" carry the same meaning as used herein. The term "immunogen" refers to an agent that is capable of being specifically bound by components of the immune system (e.g., by an antibody and/or lymphocytes), and generating a humoral and/or cell-mediated immune response in a subject of interest. As used herein, the term "immunogen" in an expression such as "glycoconjugate immunogen" refers to the ability (i.e., physical characteristic or property) of the glycoconjugate without limiting the glycoconjugate itself to a particular use (e.g., as an immunogen for generating an immune response in a subject). For example, in some embodiments, a glycoconjugate immunogen described herein may be employed in diagnostic assays or methods (e.g., in vitro methods) to detect the presence or absence of an antibody that binds to the glycoconjugate immunogen in a biological sample (e.g., from a subject). In some embodiments, the glycoconjugate immunogens described herein may be used for screening, identifying, or evaluating antibodies that bind specifically to the glycoconjugate immunogen (e.g., monoclonal antibodies that are diagnostically or therapeutically applicable).

In some aspects, the present description relates to the use of a "click chemistry-type" approach for directly conjugating carbohydrate antigens to free thiol groups of carrier proteins. More specifically, as shown in FIG. 2, photocatalytic thiol-ene reactions are preferred in which carbohydrate antigens ($R_2$) are modified to contain a terminal alkene functionality (alkenyl carbohydrate antigen) suitable for the direct covalent attachment to the cysteine thiol groups (—SH) of carrier proteins ($R_1$) using a photocatalytic thiol reaction. Referring to FIG. 3, a carbohydrate antigen comprising a B-cell epitope (such as the tumor-associated carbohydrate antigens Tn and TF) may be photochemically conjugated via a thiol-ene reaction to an immunogenic carrier protein such as tetanus toxoid (TT), which is known to have six free thiol groups owing to its six available cysteine residues (excluding four cysteine residues involved in disulfide bridges). Conjugation methods described herein, in the case of the tetanus toxoid carrier protein shown in FIG. 3, preferably result in precisely six carbohydrate antigens being conjugated at predictable (non-random) attachment points. The methods described herein are applicable to any mono-, oligo-, and polysaccharides, natural or synthetic, that can be made to end with an alkene group (terminal alkene).

In some embodiments, the carbohydrate antigens described herein may be chemically modified to be linked (directly or indirectly via a linker or spacer) to a terminal alkene (e.g., via a glycosidic bond or a bond obtained by reductive amination, such as between an allyl amine and a reducing sugar, preferably using $NaBH_4$ and/or $NaBH_3CN$), wherein the terminal alkene group of the alkenyl carbohydrate antigen is conjugatable to a free thiol of a carrier protein (e.g., one or more solvent-accessible cysteine residues, and/or cysteines not involved in disulfide bridges) via a thiol-ene reaction (e.g., a photocatalytic thiol-ene reaction). The terminal alkene group of the alkenyl carbohydrate antigen may be a monosubstituted alkene, a vinyl group, or an allyl group. In preferred embodiments, the alkenyl carbohydrate antigen is water-soluble, enabling its use in aqueous-based thiol-ene reactions described herein.

As used herein, the "glycosidic bond" may comprise one or more of an S-glycosidic bond, an N-glycosidic bond, an O-glycosidic bond, or a C-glycosidic bond, or a bond obtained by reductive amination of a reducing sugar (e.g., using $NaBH_4$ or preferably $NaBH_3CN$). In some embodiments, the glycosidic bond may be one that is not cleavable by an endogenous enzyme (e.g., a glycohydrolase) of the subject to be administered. Such an uncleavable glycosidic bond may result in a glycoconjugate immunogen having a longer half-life following administration to the subject, which may in turn generate a more favorable immune response for therapeutic and/or antibody-generation purposes. In some embodiments, the glycosidic bond may be an S-glycosidic bond, an N-glycosidic bond, or a C-glycosidic bond, or a bond obtained by reductive amination, such as between an allyl amine and a reducing sugar.

In some embodiments, the use of a "linker" or "spacer" is preferred and such terms are used herein to refer to a chemical linkage that provides sufficient physical separation of the carbohydrate antigen from the carrier protein to which it is conjugated to allow the carbohydrate antigen to be recognized by the immune system of a subject (e.g., as opposed to being masked by the carrier protein). In some embodiments, the linker may comprise a chain of at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 contiguous residues selected from C, S, N, and O.

As used herein, the term "conjugatable" refers to the ability or capability of at least two molecules (e.g., a carbohydrate antigen and a carrier protein) to be covalently bonded to one another via a chemical reaction, regardless of whether the molecules are actually covalently bonded to one another. In contrast, the term "conjugated" refers to at least two molecules (e.g., a carbohydrate antigen and a carrier protein) which are covalently bonded to one another.

In some embodiments, different types of carbohydrate antigens may be made to end with a terminal alkene group that is directly conjugatable to a thiol group via a thiol-ene reaction. For example, carbohydrate antigens having a terminal alkene group may be synthesized by adapting the approaches described herein in Examples 2-7 for the synthesis of the allyl Tn and allyl TF reactants.

In some embodiments, the carbohydrate antigens having a terminal alkene group may be conjugated to free thiol groups of carrier proteins using photocatalytic thiol-ene reactions, for example, by adapting the approaches described herein in Examples 8 and 9 for the synthesis of the Tn-TT and the TF-TT conjugates. For example, one or more alkenyl carbohydrate antigens dissolved in an aqueous solvent (e.g., a buffer such as PBS), is mixed with a carrier protein also dissolved in an aqueous solvent (e.g., a buffer such as PBS) in a vessel (e.g., quartz cell) suitable for ultraviolet light irradiation. The mixture is then irradiated under short-wave, medium-wave or long-wave ultraviolet light (e.g., having a peak wavelength at about 254 nm, at about 355 nm, or at about 365 nm), in the presence or absence of a catalyst (e.g., a photoinitiator or activator). As use herein the context of the thiol-ene reactions, the terms "catalyst," "photoinitiator," and "activator" may be used interchangeably to refer to substances that accelerate conjugation of a carbohydrate antigen to a carrier protein at the one or more free thiol groups via a photocatalytic thiol-ene reaction.

In some embodiments, the catalyst may be a water-soluble photoinitiator such as a water-soluble free radical-generating azo compound; 2,2'-azobis[2-(2-imidazolin-2-yl)propane] dihydrochloride (Vazo 44 or VA-044); 2,2'-azobis(2-amidinopropane) dihydrochloride (AAPH); metals or metal ions having photoinitiator activity; or any derivative thereof having photoinitiator activity in a photocatalytic thiol-ene reaction described herein. In some embodiments, the catalyst may be a water-soluble photoinitiator such as a water-soluble peroxide such as tert-butyl hydroperoxide or benzoylperoxide, or ammonium persulfate, or other suitable catalysts.

In some embodiments, the catalyst may be a water-insoluble photoinitiator such as a water-insoluble free radical-generating azo compound; 2,2-dimethoxy-2-phenylacetophenone (DMPA), azobisisobutyronitrile (AIBN), 2,2'-azobis(2-methylpropionitrile), 4,4'-azobis(4-cyanopentanoic acid) (ACVA), 1,1'-Azobis(cyanocyclohexane) (ACHN), diazenedicarboxylic acid bis (N,N-dimethylamide) (TMAD); azodicarboxylic acid dipiperidide (ADD), or any derivative thereof having photoinitiator activity in a photocatalytic thiol-ene reaction described herein.

In some embodiments, the photocatalytic thiol-ene reactions described herein may comprise controlling the ratio of molar equivalents of the alkenyl carbohydrate antigen (i.e., carbohydrate antigen comprising a terminal alkene) per free thiol group of the carrier protein, for example, to reduce, minimize, or avoid sugar polymerization. In some embodiments, the photocatalytic thiol-ene reactions described herein may comprise reacting between 1 to 300, 1 to 250, 1 to 200, 1 to 100, or 1 to 10, 1 to 5, or 1 to 2 molar equivalents of the carbohydrate antigen per free thiol group of the carrier protein.

In some embodiments, the photocatalytic thiol-ene reactions described herein are performed for sufficient time to achieve at least a 2, 3, 4, 5, 10, 15, 20, 25, 30, 35, 40, 45, or 50-fold reduction in total free thiol concentration in the carrier protein (e.g., as determined by Ellman test). In some embodiments, the photocatalytic thiol-ene reactions described herein are performed for 10 to 300, 10 to 270, 10 to 240, 10 to 210, 10 to 180, 10 to 150, 10 to 120, 10 to 90, 10 to 60, or 10 to 30 minutes.

In some embodiments, the photocatalytic thiol-ene reactions described herein may be performed at a pH between about 3.0, 3.1, 3.2, 3.3, 3.4, 3.5, 3.6, 3.7, 3.8, 3.9, or 4.0, and about 4.5, 4.6, 4.7, 4.8, 4.9, 5.0, 5.5, 6.0, 6.5, 7.0, 7.5, 8.0, 8.5, 9.0, 9.5, or 10. In some embodiments, the photocatalytic thiol-ene reactions described herein may be performed at a pH that avoids carrier protein denaturation. In some embodiments, the photocatalytic thiol-ene reactions described herein may be performed at a pH of between 4 and 5, preferably at pH 4.4 (e.g., in an acetate buffer).

In some embodiments, the use of a water-soluble photoinitiator (over a photoinitiator requiring an organic solvent) may be advantageous, as the thiol-ene conjugation reactions described herein may be performed only using aqueous reagents and aqueous solvents, since organic solvents may contribute to denaturation of the carrier protein, as well as undesired/unpredictable conjugation to non-free cysteine residues (e.g., cysteines involved in intramolecular and/or intermolecular disulfide bonds), as described in Dondoni et al., 2009 and Dondoni et al., 2012.

In alternative embodiments, a water-insoluble photoinitiator may be employed together with an organic solvent, as needed, for dissolution thereof. Preferably, the presence or concentration of the organic solvent shall not contribute to denaturation of the carrier protein, as well as undesired/unpredictable conjugation to non-free cysteine residues (e.g., cysteines involved in intramolecular and/or intermolecular disulfide bonds). For example, such a photoinitiator may be one such as 2,2-dimethoxy-2-phenylacetophenone (DMPA).

Figure 4:
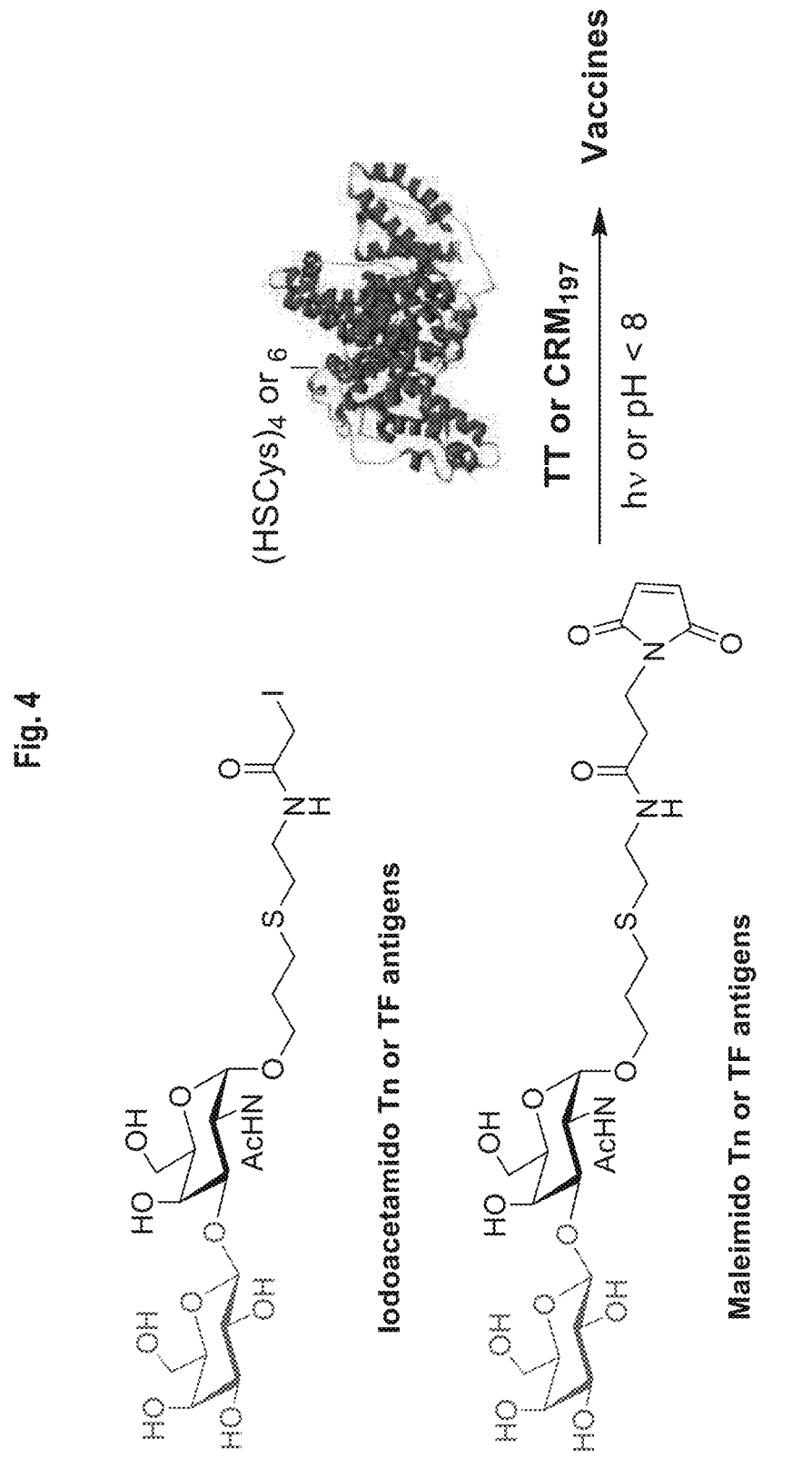
FIG. 4 shows an example of a "precision glycoconjugate" prepared by using Tn or TF antigens linked to thiol-specific iodoacetamido or maleimido groups, which are then conjugated to "free" cysteine residues on a carrier protein via a reaction a pH below 8 (iodoacetamido or maleimido groups) or a thiol-ene reaction (maleimido group).

In alternate embodiments to the thiol-ene approach described herein, the carbohydrate antigens described herein may be modified to have one or more thiol-specific functional groups such as iodoacetamides, maleimides, benzylic halides, or bromomethylketones, which react by S-alkylation of thiols to generate stable thioether products (e.g., carried out at relatively low pHs such as below 9, 8, 7.5, or 7, and above 5, 5.5, or 6, which may avoid unwanted, random carbohydrate antigen conjugations to lysine residues). Examples of carbohydrate antigens that have been modified to comprise thiol-specific functional groups (e.g., iodoacetamido and maleimido groups) are shown in FIG. 4. In some embodiments, the maleimido groups qualify as terminal alkenes that are conjugatable to thiol groups of carrier proteins via a thiol-ene reaction.

In some embodiments, the carbohydrate antigens described herein may comprise one or more B cell epitopes, and/or may induce a humoral immune response, and/or may comprise a T cell epitope, and/or induce a cell-mediated immune response in a subject upon administration. In some embodiments, glycoconjugate immunogens described herein may induce at least a cell-mediated immune response (e.g., in addition to a humoral response) to the carbohydrate antigen upon administration to a subject.

In some embodiments, the carbohydrate antigens described herein may be or comprise, for example, a tumor associated carbohydrate antigen (TACA). Glycoproteins and glycolipids of the outer cell membranes of cancer cells overexpress particular O-glycans. These glycoproteins constitute a family of proteins collectively known as mucins (MUCs) with MUC1 representing the most widely investigated. MUCs on normal cells are heavily O-glycosylated due to active glycosyltransferases which give rise to complex glycosylation patterns. In cancer cells, down-regulation of key glycosyltransferases trigger the accumulation of shorter glycans, giving rise to much more limited O-glycosylation on mucins. The consequence of these altered glycosylation patterns between normal and cancerous cells is the over accumulation of TACAs, which are otherwise cryptic (masked) by the complex glycosylation on normal tissues. The most common TACAs include the Tn antigen (a monosaccharide having the structure N-acetylgalactosamine (GalNAc)), the TF antigen (Thomsen-Friedenreich antigen, a disaccharide having the structure Galβ1-3GalNAcα1), and their cognate sialylated analogs, respectively. Overexpression of both the Tn and TF antigens on the cell surface of several types of tumor cells contributes to cancer cell adhesion and severe metastasis to sites containing receptor lectins (lungs, liver, lymph nodes, etc.). Accordingly, in some embodiments, the TACA described herein is, is from, or comprises: Tn antigen, STn antigen, Thomsen-Friedenreich (TF) antigen, (2,3)-S-TF, (2,6)-S-TF, Globo H, GD2, GD3, GM2, GM3, N-glycolyl-GM3, Lea, sLea, Lex, sLex, or any combination thereof. The structures of some common TACAs are shown in FIG. 1. As used herein, the expression "is from", when used in the context of carbohydrate antigens, refers to carbohydrate variants derived from a known carbohydrate antigen, wherein the variant retains at least the antigenicity of the known carbohydrate antigen. For persons skilled in art, the synthesis of alkenyl-ending TACAs can be performed by both chemical as well as by chemoenzymatic processes, as described in Danishefsky et al., 2015.

In some embodiments, the carbohydrate antigens described herein may be or comprise carbohydrate antigens associated with infectious agents, such as, but not limited to, bacteria and/or viruses, or associated with infections, such as, but not limited to bacterial infections and/or viral infections. In some embodiments, the carbohydrate antigens described herein may be or comprise, for example, a viral polysaccharide antigen, or a bacterial capsular polysaccharide (CPS). In some embodiments, the bacterial CPS is, is from, or comprises a Pneumococcal and/or Streptococcal polysaccharide serotype, meningococcal CPS, or influenza (such as influenza type a and b) CPS.

In some embodiments, the conjugation methods described herein may conjugate the same or more than one type of carbohydrate antigen to the carrier protein, thereby producing a multi-valent glycoconjugate immunogen. In some embodiments, the multi-valent glycoconjugate immunogens described herein may comprise 2, 3, 4, 5, 6, 7, 8, 9, 10, 11, 12, 13, 14, 15, or more of the same or different types of carbohydrate antigens conjugated to a carrier protein. In some embodiments, the multi-valent glycoconjugate immunogens described herein may comprise more than one carbohydrate antigen that is conjugated to a single free thiol group on the carrier protein (e.g., via branched linker). In some embodiments, the multi-valent glycoconjugate immunogens described herein may comprise a plurality (e.g., at least 3, 4, 5, 6, 7 8, 9. 10, 11, 12, 13, 14, 15, or more) of carbohydrate antigens that are conjugated to a single free thiol group on the carrier protein as a dendrimer (e.g., via linkers having extensive branching). In some embodiments, the carrier proteins described herein comprise one or more free thiol groups. As used herein, "free thiol" or "free thiol group" refers to carrier proteins having one or more sulf-hydryl groups that are available for chemical modification and/or conjugation (e.g., to a carbohydrate antigen as described herein). In some embodiments, the free thiol concentration of a given carrier protein may be measured for example using the Ellman test using a cysteine standard curve, as described in the present Examples. The free thiol concentration of a given carrier protein may be expressed as fold reduction in free thiol concentration. In some embodiments, the glycoconjugates described herein may have at least a 50, 45, 40, 35, 30, 25, 20, 15, 10, 5, 4, 3, or 2-fold decrease in free thiol concentration following a conjugation method described herein (e.g., as measured by Ellman test).

In some embodiments, the carrier proteins described herein may be engineered to add one or more further cysteine residues, for example at the amino terminus, the carboxy terminus, or any solvent-accessible position of the carrier protein therebetween (as opposed to at positions that are not solvent accessible or "buried" within the three-dimensional structure of the protein carrier). In some embodiments, free thiol groups of protein carriers described herein may be defined as cysteines that are readily conjugatable to an alkenyl carbohydrate antigen by a photocatalytic thiol-ene reaction, when the reaction is performed under conditions sufficiently mild to not destroy the immunogenicity, structure, or activity of the carrier protein. In some embodiments, the term "activity" as used herein in relation to a carrier protein refers to the ability of the carrier protein to preserve the immunogenicity of the carbohydrate antigen (e.g., to an antibody that is known to specifically bind to the carbohydrate antigen).

In some embodiments, the free thiol group may refer to one or more solvent-accessible cysteine residues of the carrier protein, and/or cysteines that are not involved in disulfide bridges, which in some cases may be important to maintain the structure of the carrier protein. In some embodiments, the carrier protein may be a protein having one or more disulfide bridges, and wherein the one or more disulfide bridges remain unaffected (i.e., intact) following conjugation to the carbohydrate antigen. In some embodiments, the carrier proteins described herein do not comprise free thiol-groups at their N and/or C-termini. Alternatively, in some embodiments, the carrier proteins described herein may comprise, or be engineered to comprise, a free thiol-group at their N and/or C-termini. In some embodiments, the carrier protein may be a protein having one or more disulfide bridges, and wherein the carrier protein may be pre-treated with a reducing agent (e.g., dithiothreitol (DTT), 2-mercaptoethanol, tris(2-carboxyethyl)phosphine (TCEP), or 2-mercaptoethylamine-HCl) to expose one or more additional free thiol groups for conjugation to the carbohydrate antigen. Such pre-treatments may be useful for example when the denatured (reduced) carrier protein has higher immunogenicity in a subject than the native (unreduced) carrier protein.

In some embodiments, the carrier protein, prior to or together with performing the photocatalytic thiol-ene reaction, may be pre-treated with a reducing agent (e.g., as described herein). This pre-treatment may expose additional free thiol groups available for conjugation. In some embodiments, the carrier protein, prior to or together with performing the photocatalytic thiol-ene reaction, may be pre-treated with a thiolating agent (e.g., 2-imminothiolane, N-hydroxy-succinimide dithiopropionate (DPS)). This pre-treatment may be employed to increase the number free thiol groups available for conjugation. In some embodiments, the carrier protein, prior to or together with performing the photocatalytic thiol-ene reaction, may be pre-treated with a thiolating agent, and subsequently pre-treated with a reducing agent.

In some embodiments, it may be advantageous to avoid having too many multiple carbohydrate antigens conjugated to adjacent positions on the carrier proteins. In some embodiments, the carrier protein may preferably lack a cysteine-rich domain (e.g., a segment of at least 4, 5, 6, 7, 8, 9, or 10 consecutive amino acids comprising at least 50% of cysteine residues).

In some embodiments, the carrier protein may comprise 1, 2, 3, 4, 5, 6, 7, 8, 9, 10, 11, 12, 13, 14, 15, 16, 17 18, 19, 20, 21, 22, 23, 24, 25, 26, 27, 28, 29, or 30 total cysteine residues. In some embodiments, the carrier protein may comprise 1, 2, 3, 4, 5, 6, 7, 8, 9, 10, 11, 12, 13, 14, 15, 16, 17 18, 19, 20, 21, 22, 23, 24, 25, 26, 27, 28, 29, or 30 total free cysteine residues.

In some embodiments, the total number of carbohydrate antigens comprised in the glycoconjugate immunogens described herein is equal to the number of free thiol groups available on the carrier protein prior to conjugation. In some embodiments, the glycoconjugate immunogens described herein may comprise 1, 2, 3, 4, 5, 6, 7, 8, 9, 10, 11, 12, 13, 14, 15, 16, 17 18, 19, 20, 21, 22, 23, 24, 25, 26, 27, 28, 29, or 30 carbohydrate antigens per carrier protein. In some embodiments, the present description relates to a composition comprising glycoconjugate immunogens having about or at least 70%, 75%, 80%, 85%, 90%, or 95% homogeneity in terms of carbohydrate conjugation species (e.g., at least 90% of glycoconjugate immunogen species/molecules in the composition have the same number of carbohydrate antigens conjugated to the carrier protein).

In some embodiments, the carrier proteins described herein are proteins (e.g., peptides or polypeptides) that are preferably immunogenic to a subject that is to be administered to the glycoconjugate immunogen. Preferably, conjugation of the carbohydrate antigen to the carrier protein increases the immunogenicity of the carbohydrate antigen upon administration to the subject, as compared to administration of the unconjugated carbohydrate antigen (i.e., the carbohydrate antigen administered to the subject alone).

In some embodiments, the carrier proteins may comprise a T cell epitope, and/or induce a cell-mediated immune response in the subject upon administration.

In some embodiments, the carrier protein is a protein that is exogenous to the subject to be administered, which preferably has no (close) ortholog in the subject. In the context of human vaccine production, a carrier protein described herein refers to a "carrier protein suitable for human use" or simply "suitable carrier protein", which means a carrier protein that is antigenically distinct from human proteins such that the carrier protein would not be considered as a "self-antigen" in humans. The use of carrier proteins that are too antigenically similar to corresponding human proteins may result in the carrier protein being considered as a "self-antigen", which may not be ideal in human vaccines. For example, glycoconjugate immunogens consisting of TF antigen randomly conjugated to the ε-amino groups of lysine residues of bovine serum albumin (BSA) have been previously described and characterized (e.g., Demian et al., 2014; Rittenhouse-Diakun et al., 1998; Heimburg et al., 2006; Tati et al., 2017). However, not only was the level of carbohydrate on the 59 lysine residues of BSA random and inefficient (no more than 4 to 6 TF antigens were conjugated per BSA molecule), BSA would not be suitable as a carrier protein in human vaccines because it is too antigenically similar to human albumin. In some embodiments, the carrier protein is not albumin (e.g., bovine serum albumin).

Preferably, the carrier protein described herein may be a protein that has already received regulatory (e.g., FDA) approval for administration to human subjects (e.g., in approved vaccines). In some embodiments, the carrier protein is, is from, or comprises Tetanus Toxoid (TT), Diphtheria Toxoid (DT), cross-reacting material 197 (CRM197), Meningococcal Outer Membrane Protein Complex (OMPC), *H. influenzae* Protein D (HiD), a cytokine, or an immunogenic fragment (or variant) thereof.

In some embodiments, the carrier protein may be TT which contains 10 cysteine residues, 4 of which being engaged in disulfide bridges, giving rise to a glycoconjugate immunogen having 6 conjugated carbohydrate antigens. In some embodiments, the carrier protein may be CRM197 which contains 4 cysteine residues, giving rise to a glycoconjugate immunogen having 4 conjugated carbohydrate antigens.

In some embodiments, the carrier proteins may by engineered to introduce additional cysteine residues in order to introduce additional free thiol groups for conjugation to carbohydrate antigens. In some embodiments, the cysteine residues may be engineered at solvent exposed portions of the carrier protein.

In some aspects, the present description relates to a method for producing a glycoconjugate vaccine or an immune response-triggering composition. The method may comprise formulating the glycoconjugate immunogen described herein with a pharmaceutically acceptable excipient, and/or an adjuvant. In some embodiments, the adjuvant is or comprises: an inorganic compound, a mineral oil, a microbial derivative, a plant derivative, a cytokine, squalene, alum, aluminum hydroxide, aluminum phosphate, calcium phosphate hydroxide, a toll-like receptor agonist, an immunostimulatory polynucleotide (e.g., CPG), an immunostimulatory lipid, Freund's adjuvant, RIBI's adjuvant, QS-21, muramyl dipeptide, TiterMax™, Steviune™, Stimune™, or any combination thereof.

In some aspects, the present description relates to a synthetic glycoconjugate immunogen comprising one or more carbohydrate antigens and an immunogenic carrier protein having one or more solvent-accessible cysteine residues, wherein the one or more carbohydrate antigens are linked to the immunogenic carrier protein at the one or more solvent-accessible cysteine residues. The conjugation of the one or more carbohydrate antigens to the immunogenic carrier protein increases the immunogenicity of the one or more carbohydrate antigens upon administration to a subject, as compared to administration of the unconjugated carbohydrate antigen. As use herein, the term "synthetic" refers to a compound that is not a product of nature, which is produced by human intervention.

In some embodiments, glycoconjugate immunogens described herein may comprise more than one species of carbohydrate antigen (e.g., more than one type of TACA) conjugated to the same carrier protein. For example, glycoconjugate immunogens described herein may comprise at least 2, 3, 4, 5, 6, 7, 8, 9, 10, 11, 12, 13, 14, 15 or more types or species of carbohydrate antigen (e.g., TACA). In some embodiments, glycoconjugate immunogens described herein may comprise any combination of TACAs selected from Tn, S-Tn, Thomsen-Friedenreich (TF), (2,3)-S-TF, (2,6)-S-TF, Globo H, GD2, GD3, GM2, GM3, N-glycolyl-GM3, Lea, sLea, Lex, and sLex. In some embodiments, ratio in the combination of each TACAs may vary with the targeted tumor and may comprise between 1 to 20 molar ratios. In this way, the glycoconjugate immunogens described herein may be tailored, for example, to specific forms of cancer that are associated with increased expression of particular combinations of multiple TACAs.

In some aspects, the present description relates to a glycoconjugate vaccine which is produced by a method described herein, and/or which comprises a synthetic glycoconjugate immunogen described herein, and further comprises a pharmaceutically acceptable excipient, and/or an adjuvant. As used herein, the term "vaccine" refers to a composition comprising a glycoconjugate immunogen described herein that is administered a subject to provide a therapeutic benefit to the subject. In some embodiments, the glycoconjugate vaccines described herein may be a prophylactic vaccine or a therapeutic vaccine.

Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, ocular) or via a parenteral route (e.g., intradermal, intramuscular, subcutaneous). Vaccine compositions can be administered alone, or can be co-administered or sequentially administered with other treatments or therapies. Forms of administration may include suspensions and preparations for parenteral, subcutaneous, intradermal or intramuscular administration (e.g., injectable administration) such as sterile suspensions or emulsions. Vaccines may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

In some aspects, the present description relates to a method of immunizing, vaccinating, or treating a subject comprising administering to the subject a glycoconjugate immunogen or a glycoconjugate vaccine described herein.

In some aspects, the present description relates to a carbohydrate antigen chemically modified to be linked to a sulfhydryl-specific (thiol specific) functional group. In some embodiments, the carbohydrate antigen is chemically modified to be linked to a terminal alkene (e.g., via a glycosidic bond), wherein the terminal alkene group is conjugatable to a free thiol of a carrier protein via a thiol-ene reaction. In some embodiments, the carbohydrate antigen and the terminal alkene group are linked via a linker as described herein. In some embodiments, the terminal alkene group may be a vinyl group or an allyl group.

In some aspects, the present description relates to a synthetic glycoconjugate immunogen comprising one or more sugar antigens covalently linked to one or more free thiol groups of a carrier protein via a linker, wherein each linker has the structure:

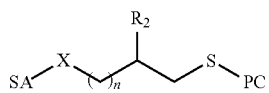

wherein: SA is a sugar antigen or a portion thereof; S—PC is a carrier protein; X is O, S, NR$_1$, or CH$_2$; R$_1$ is —H, —COH, —COCH$_3$, or —COEt; n is 1, 2, 3, 4, or 5; and R$_2$ is H or Me; or a stereoisomer (e.g., diastereomer) thereof.

In some aspects, the present description relates to a synthetic glycoconjugate immunogen comprising one or more sugar antigens covalently linked to one or more free thiol groups of a carrier protein via a linker, wherein each linker has the structure:

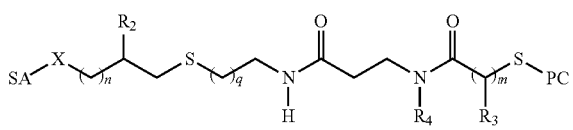

wherein: SA is a sugar antigen or a portion thereof; S—PC is a carrier protein; X is S, NR$_1$, CH$_2$ or O; R$_1$ is —H, —COH, —COMe, or —COEt; n is 1, 2, 3, 4, or 5; R$_2$ is H or Me; q is 1, 2, 3, 4, or 5; R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; or a stereoisomer (e.g., diastereomer) thereof. In some embodiments, when X is O, the sugar antigen does not comprise Tn or STn.

In some aspects, the present description relates to a synthetic glycoconjugate immunogen comprising one or more sugar antigens covalently linked to one or more free thiol groups of a carrier protein via a linker, wherein the synthetic glycoconjugate immunogen has the structure:

wherein
y is at least 1;
SA is selected from the group consisting of sugar antigens or immunogenic portions thereof, and when y is more than 1, SA are identical or different;
[S]$_z$—PC is a carrier protein having one or more sulfur atoms originating from the one or more free thiol groups;
z is at least 1 and is at least equal to y; and
L is a linker selected from the group consisting of linkers having the structure:

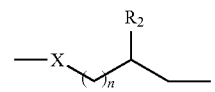

wherein:
X is O, S, NR$_1$, or CH$_2$;
R$_1$ is —H, —COH, —COCH$_3$, or —COEt;
n is 1, 2, 3, 4, or 5; and
R$_2$ is H or Me; and
when y is more than 1, L are identical or different;
or a stereoisomer thereof.

In some aspects, the present description relates to a synthetic glycoconjugate immunogen comprising one or more sugar antigens covalently linked to one or more free thiol groups of a carrier protein via a linker, wherein the synthetic glycoconjugate immunogen has the structure:

wherein
y is at least 1;
SA is selected from the group consisting of sugar antigens or immunogenic portions thereof, and when y is more than 1, SA are identical or different;
[S]$_z$—PC is a carrier protein having one or more sulfur atoms originating from the one or more free thiol groups;
z is at least 1 and is at least equal to y; and
L is a linker selected from the group consisting of linkers having the structure:

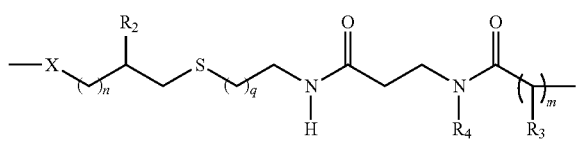

wherein:
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5;
R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; and
when y is more than 1, L are identical or different;
or a stereoisomer thereof.

In some aspects, the present description relates to a synthetic glycoconjugate immunogen comprising one or more sugar antigens covalently linked to one or more free thiol groups of a carrier protein via a linker, wherein the synthetic glycoconjugate immunogen has the structure:

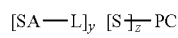

wherein
y is at least 1;
SA is selected from the group consisting of sugar antigens or immunogenic portions thereof, and when y is more than 1, SA are identical or different;
[S]$_z$—PC is a carrier protein having one or more sulfur atoms originating from the one or more free thiol groups;
z is at least 1 and is at least equal to y; and
L is a linker selected from the group consisting of linkers having the structure:

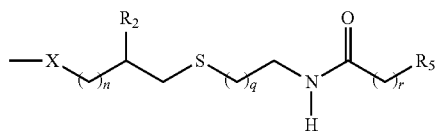

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5;
r is 1, 2, 3, 4 or 5;
R$_5$ is S—PC, a covalent bond or a radical of structure:

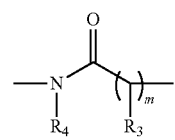

wherein R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; and
when y is more than 1, L are identical or different;
or a stereoisomer thereof.

In some embodiments, the present description relates to the synthetic glycoconjugate immunogen as defined above, wherein the linker has the structure:

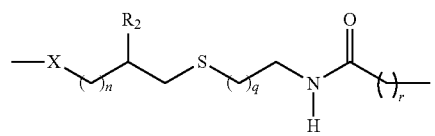

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5; and
r is 1, 2, 3, 4 or 5.

In some embodiments, the present description relates to the synthetic glycoconjugate immunogen as defined above, wherein the linker has the structure:

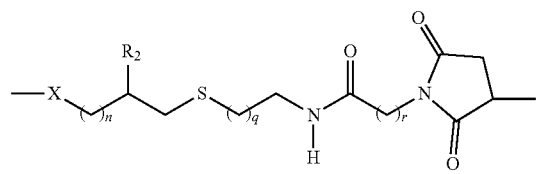

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5; and
r is 1 or 2.

In some embodiments, the present description relates to the synthetic glycoconjugate immunogen as defined above, wherein the linker has the structure:

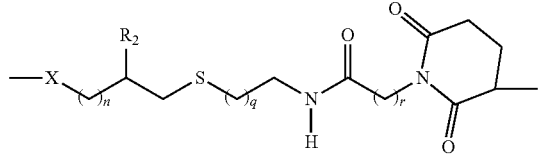

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5; and
r is 1 or 2.

In some embodiments, the present description relates to the synthetic glycoconjugate immunogen as described above, wherein y is an integer varying from 1 to 50, 1 to 40, 1 to 30, 1 to 20, or 1 to 10, 1 to 5, or 1 to 2.

In some embodiments, the sugar antigen may be a carbohydrate antigen as described herein, and/or the carrier protein may be a carrier protein as described herein. In some embodiments, the synthetic glycoconjugate immunogen may be a multi-valent glycoconjugate immunogen, for example, comprising 2, 3, 4, 5, 6, 7, 8, 9, 10, 11, 12, 13, 14, 15, or more of the same or different types of carbohydrate antigens conjugated to a carrier protein. In some embodiments, the glycoconjugate immunogen may induce a cell-mediated immune response to the carbohydrate antigen upon administration to a subject.

In some aspects, the present description relates to a vaccine comprising a synthetic glycoconjugate immunogen as described herein, and a pharmaceutically acceptable excipient and/or an adjuvant (e.g., an adjuvant as described herein).

In some aspects, the present description relates to the use of the glycoconjugate immunogen prepared by a method as described herein, or a synthetic glycoconjugate immunogen as described herein, for the manufacture of a vaccine.

In some aspects, the present description relates to the use of the glycoconjugate immunogen prepared by a method as described herein, the glycoconjugate vaccine produced by a method as described herein, a synthetic glycoconjugate immunogen as described herein, or a vaccine as described herein, for the treatment of a subject having a disease associated with increased expression of said one or more carbohydrate or sugar antigens.

In some aspects, the present description relates to the use of the glycoconjugate immunogen prepared by a method as described herein, the glycoconjugate vaccine produced by a method as described herein, a synthetic glycoconjugate immunogen as described herein, or a vaccine as described herein, for producing an antibody that specifically binds to the glycoconjugate immunogen.

In some aspects, the present description relates to the use of the glycoconjugate immunogen prepared by a method as described herein, the glycoconjugate vaccine produced by a method as described herein, a synthetic glycoconjugate immunogen as described herein, or a vaccine as described herein, for detecting an antibody that specifically binds to the glycoconjugate immunogen.

In some aspects, the present description relates to a method for producing a glycoconjugate, the method comprising: (a) providing a carbohydrate antigen covalently linked to a terminal alkene (alkenyl carbohydrate antigen), the terminal alkene being directly conjugatable to a thiol group via a thiol-ene reaction; (b) providing a conjugate material suitable for conjugation to the carbohydrate antigen via a thiol-ene reaction as described herein, said conjugate material having one or more free thiol groups; and (c) performing a photocatalytic thiol-ene reaction to directly conjugate the carbohydrate antigen to the conjugate material at the one or more free thiol groups, thereby producing the glycoconjugate. In some embodiments, the conjugate material is or comprises a polymer, a polypeptide, a carrier protein as defined herein, a solid support, a particle, or any other material having a free thiol group suitable for conjugation to the carbohydrate antigen via a thiol-ene reaction as described herein.

In some aspects, the present description relates to the use of a glycoconjugate produced by a method described herein, for detecting or screening for the presence of an antibody that specifically binds to a carbohydrate antigen or a tumor-circulating cell comprising a carbohydrate antigen, or for detecting the presence of antibodies resulting from an immunization or vaccination with a carbohydrate antigen. In some embodiments, the detection or screening may be performed via any suitable detection method, such as an immunosorbent assay, ELISA, microarray, or immunoblot analysis.

In some aspects, the present description relates a method of treating a subject comprising administering a glycoconjugate or glycoconjugate immunogen as defined herein or produced by a method as described herein, to generate an immune response in said subject to a carbohydrate antigen, and screening a biological sample from said subject for the presence of antibodies that specifically binds to the carbohydrate antigen.

Other objects, advantages and features of the present description will become more apparent upon reading of the following non-restrictive description of specific embodiments thereof, given by way of example only with reference to the accompanying drawings.

Items

1. A method for producing a glycoconjugate immunogen for administration to a subject, the method comprising: (a) providing a carbohydrate antigen covalently linked to a terminal alkene (alkenyl carbohydrate antigen), the terminal alkene being directly conjugatable to a thiol group via a thiol-ene reaction; (b) providing a carrier protein having one or more free thiol groups; and (c) performing a photocatalytic thiol-ene reaction to directly conjugate the carbohydrate antigen to the carrier protein at the one or more free thiol groups, thereby producing the glycoconjugate immunogen; wherein the carrier protein is immunogenic to the subject, and wherein conjugation of the carbohydrate antigen to the carrier protein increases the immunogenicity of the carbohydrate antigen upon administration to the subject, as compared to administration of the unconjugated carbohydrate antigen.
2. The method of item 1, wherein the alkenyl carbohydrate antigen is water-soluble.
3. The method of item 1 or 2, wherein said photocatalytic thiol-ene reaction is performed under reactions conditions that retain the carrier protein's activity, antigenicity, and/or structure.
4. The method of any one of items 1 to 3, wherein said photocatalytic thiol-ene reaction is performed in the absence of any organic solvent.
5. The method of any one of items 1 to 4, wherein said photocatalytic thiol-ene reaction is performed in the presence of a catalyst.
6. The method of item 5, wherein the catalyst is a water-soluble catalyst.
7. The method of any one of items 1 to 6, wherein said photocatalytic thiol-ene reaction comprises irradiation under short-wave ultraviolet light.
8. The method of item 7, wherein said photocatalytic thiol-ene reaction comprises irradiation at about 254 nm.
9. The method of any one of items 1 to 6, wherein said photocatalytic thiol-ene reaction comprises irradiation under long-wave ultraviolet light.
10. The method of item 9, wherein said photocatalytic thiol-ene reaction comprises irradiation at about 365 nm.
11. The method of any one of items 1 to 10, wherein said photocatalytic thiol-ene reaction comprises reacting between 1 to 10 molar equivalents of the alkenyl carbohydrate antigen per free thiol group of the carrier protein.
12. The method of any one of items 1 to 11, wherein said photocatalytic thiol-ene reaction is performed at a pH between about 3.0, 3.1, 3.2, 3.3, 3.4, 3.5, 3.6, 3.7, 3.8, 3.9, or 4.0, and about 4.5, 4.6, 4.7, 4.8, 4.9, 5.0, 5.5, 6.0, 6.5, 7.0, 7.5, 8.0, 8.5, 9.0, 9.5, or 10.

13. The method of any one of items 1 to 12, wherein said carbohydrate antigen, following conjugation to the carrier protein, is not cleavable from the carrier protein by an endogenous enzyme of the subject.
14. The method of any one of items 1 to 13, wherein said alkenyl carbohydrate antigen is covalently linked to the terminal alkene, and/or the carbohydrate antigen is conjugated to the carrier protein, via a glycosidic bond, such as is an O-glycosidic bond, an S-glycosidic bond, an N-glycosidic bond, or a C-glycosidic bond, or a bond obtained by reductive amination, such as between an allyl amine and a reducing sugar.
15. The method of any one of items 1 to 14, wherein the carbohydrate antigen comprises a B cell epitope, and/or induces a humoral immune response in the subject.
16. The method of any one of items 1 to 15, wherein the carbohydrate antigen is or comprises a tumor associated carbohydrate antigen (TACA).
17. The method of item 16, wherein the TACA is, is from, or comprises: Tn, S-Tn, Thomsen-Friedenreich (TF), (2,3)-S-TF, (2,6)-S-TF, Globo H, GD2, GD3, GM2, GM3, or any combination thereof.
18. The method of any one of items 1 to 17, wherein said photocatalytic thiol-ene reaction conjugates more than one type of carbohydrate antigen to the carrier protein, thereby producing a multi-valent glycoconjugate immunogen.
19. The method of item 18, wherein said multi-valent glycoconjugate immunogen comprises 2, 3, 4, 5, 6, 7, 8, 9, 10, 11, 12, 13, 14, 15, or more different types of carbohydrate antigens conjugated to the carrier protein.
20. The method of any one of items 1 to 19, wherein the carbohydrate antigen is or comprises a viral polysaccharide antigen, or a bacterial capsular polysaccharide (CPS).
21. The method of item 20, wherein the bacterial CPS is, is from, or comprises a Pneumococcal and/or Streptococcal polysaccharide serotype.
22. The method of any one of items 1 to 21, wherein the carbohydrate antigen in (a) is linked to the terminal alkene via a linker.
23. The method of any one of items 1 to 22, wherein the carrier protein comprises one or more cysteine residues having the one or more free thiol groups.
24. The method of any one of items 1 to 23, wherein the carrier protein comprises a human T cell epitope, and/or induces a cell-mediated immune response in the subject.
25. The method of any one of items 1 to 24, wherein the carrier protein is, is from, or comprises: Tetanus Toxoid (TT), Diphtheria Toxoid (DT), cross-reacting material 197 (CRM197), Meningococcal Outer Membrane Protein Complex (OMPC), H. Influenzae Protein D (HiD), a cytokine, or an immunogenic fragment thereof.
26. The method of any one of items 1 to 25, wherein the carrier protein is a protein having one or more disulfide bridges, and wherein: (i) the one or more disulfide bridges remain unaffected following said photocatalytic thiol-ene reaction; or (ii) the carrier protein is pre-treated with a reducing agent to expose one or more additional free thiol groups for conjugation to the carbohydrate antigen.
27. The method of any one of items 1 to 26, wherein the total number of carbohydrate antigens comprised in the glycoconjugate immunogen is equal to the number of free thiol groups available on the carrier protein prior to conjugation.
28. The method of any one of items 1 to 27, wherein the glycoconjugate immunogen induces a cell-mediated immune response to the carbohydrate antigen upon administration to the subject.
29. The method of any one of items 1 to 28, further comprising: (d) purifying the glycoconjugate immunogen.
30. A method for producing a glycoconjugate vaccine, the method comprising formulating the glycoconjugate immunogen prepared by the method of any one of items 1 to 29 with a pharmaceutically acceptable excipient, and/or an adjuvant.
31. The method of item 30, wherein the adjuvant is or comprises: an inorganic compound, a mineral oil, a microbial derivative, a plant derivative, a cytokine, squalene, alum, aluminum hydroxide, aluminum phosphate, calcium phosphate hydroxide, a toll-like receptor agonist, an immunostimulatory polynucleotide, an immunostimulatory lipid, Freund's adjuvant, RIBI's adjuvant, QS-21, muramyl dipeptide, or any combination thereof.
32. A synthetic glycoconjugate immunogen comprising one or more carbohydrate antigens and an immunogenic carrier protein having one or more solvent-accessible cysteine residues, wherein the one or more carbohydrate antigens are linked to the immunogenic carrier protein at the one or more solvent-accessible cysteine residues, and wherein conjugation of the one or more carbohydrate antigens to the immunogenic carrier protein increases the immunogenicity of the one or more carbohydrate antigens upon administration to a subject, as compared to administration of the unconjugated carbohydrate antigen.
33. The synthetic glycoconjugate immunogen of item 32, wherein the one or more carbohydrate antigens are linked to the one or more solvent-accessible cysteine residues via a linker.
34. The synthetic glycoconjugate immunogen of item 32, wherein the one or more carbohydrate antigen is linked to the linker via a bond as defined in item 13 or 14.
35. The synthetic glycoconjugate immunogen of any one of items 32 to 34, wherein the one or more carbohydrate antigens is/are as defined in item 2, 15, 16, 17, 20, or 21.
36. The synthetic glycoconjugate immunogen of any one of items 32 to 35, which is the multi-valent glycoconjugate immunogen as defined in item 18 or 19.
37. The synthetic glycoconjugate immunogen of any one of items 32 to 36, wherein the carrier protein is as defined in item 23, 24, 25, or 26.
38. The synthetic glycoconjugate immunogen of any one of items 32 to 37, wherein the total number of carbohydrate antigens comprised in the glycoconjugate immunogen is equal to the number of solvent-accessible cysteine residues on the carrier protein.
39. The synthetic glycoconjugate immunogen of any one of items 32 to 38, which induces a cell-mediated immune response to the carbohydrate antigen upon administration to the subject.
40. The synthetic glycoconjugate immunogen of any one of items 32 to 39, which is prepared by the method of any one of items 1 to 29.
41. A glycoconjugate vaccine produced by the method of item 30 or 31, and/or comprising the synthetic glycoconjugate immunogen of any one of items 32 to 40, and a pharmaceutically acceptable excipient, and/or an adjuvant.
42. The glycoconjugate vaccine of item 41, which is a prophylactic vaccine or a therapeutic vaccine.
43. A method of immunizing, vaccinating, or treating a subject comprising administering to the subject the glycoconjugate immunogen produced by the method of any one of items 1 to 29, the glycoconjugate vaccine produced by the method of item 30 or 31, the synthetic glycoconjugate immunogen of any one of items 32 to 40, or the glycoconjugate vaccine of item 41 or 42.

44. The synthetic glycoconjugate immunogen of any one of items 32 to 40, or the glycoconjugate vaccine of item 41 or 42, for use in immunizing, vaccinating, or treating a subject having a disease.

45. A synthetic glycoconjugate immunogen comprising one or more sugar antigens covalently linked to one or more free thiol groups of a carrier protein via a linker, wherein each linker has the structure:

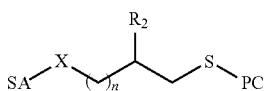

wherein:
SA is a sugar antigen or a portion thereof;
PC is a carrier protein;
X is O, S, NR$_1$, or CH$_2$;
R$_1$ is —H, —COH, —COCH$_3$, or —COEt;
n is 1, 2, 3, 4, or 5; and
R$_2$ is H or Me;
or a stereoisomer thereof.

46. A synthetic glycoconjugate immunogen comprising one or more sugar antigens covalently linked to one or more free thiol groups of a carrier protein via a linker, wherein each linker has the structure:

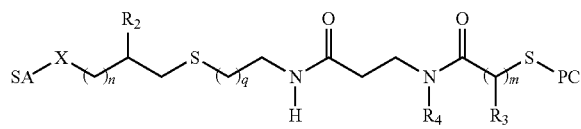

wherein:
SA is a sugar antigen or a portion thereof;
PC is a carrier protein;
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5;
R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1;
or a stereoisomer thereof.

47. The synthetic glycoconjugate immunogen of item 45 or 46, wherein said sugar antigen is the carbohydrate antigen as defined in item 15, 16, 17, 20, or 21.

48. The synthetic glycoconjugate immunogen of any one of items 45 to 47, wherein said carrier protein is the carrier protein as defined in item 23, 24, or 25.

49. The synthetic glycoconjugate immunogen of any one of items 45 to 49, which is a multi-valent glycoconjugate immunogen.

50. The synthetic glycoconjugate immunogen of item 49, wherein said multi-valent glycoconjugate immunogen comprises 2, 3, 4, 5, 6, 7, 8, 9, 10, 11, 12, 13, 14, 15, or more different types of carbohydrate antigens conjugated to the carrier protein.

51. The synthetic glycoconjugate immunogen of any one of items 45 to 50, wherein the glycoconjugate immunogen induces a cell-mediated immune response to the carbohydrate antigen upon administration to a subject.

52. A vaccine comprising the synthetic glycoconjugate immunogen of any one of items 45 to 51, and a pharmaceutically acceptable excipient and/or an adjuvant.

53. The vaccine of item 52, wherein the adjuvant is as defined in item 31.

54. Use of the glycoconjugate immunogen prepared by the method of any one of items 1 to 29, or the synthetic glycoconjugate immunogen as defined in any one of item 32 to 40 and 45 to 51, for the manufacture of a vaccine.

55. Use of the glycoconjugate immunogen prepared by the method of any one of items 1 to 29, the glycoconjugate vaccine produced by the method of item 30 or 31, the synthetic glycoconjugate immunogen as defined in any one of item 32 to 40 and 45 to 51, or the vaccine of item 52 or 53, for the treatment of a subject having a disease associated with increased expression of said one or more carbohydrate or sugar antigens.

Further Items

1. A method for producing a glycoconjugate immunogen, the method comprising:
   (a) providing a carbohydrate antigen covalently linked to a terminal alkene (alkenyl carbohydrate antigen), the terminal alkene being directly conjugatable to a thiol group via a thiol-ene reaction;
   (b) providing a carrier protein having one or more free thiol groups; and
   (c) performing a photocatalytic thiol-ene reaction to directly conjugate the carbohydrate antigen to the carrier protein at the one or more free thiol groups, thereby producing the glycoconjugate immunogen;
wherein the carrier protein is immunogenic when administered to a subject, and wherein conjugation of the carbohydrate antigen to the carrier protein increases the immunogenicity of the carbohydrate antigen upon administration to the subject, as compared to administration of the unconjugated carbohydrate antigen.

2. The method of item 1, wherein the alkenyl carbohydrate antigen is water-soluble.

3. The method of item 1 or 2, wherein said photocatalytic thiol-ene reaction is performed under reaction conditions that avoid carrier protein denaturation, and/or that retain the carrier protein's activity, antigenicity, and/or structure.

4. The method of any one of items 1 to 3, wherein said photocatalytic thiol-ene reaction is performed in the absence of any organic solvent, or wherein said photocatalytic thiol-ene reaction is performed in the presence of an organic solvent at a concentration sufficiently low to avoid carrier protein denaturation.

5. The method of any one of items 1 to 4, wherein said photocatalytic thiol-ene reaction is performed in the presence of a catalyst.

6. The method of item 5, wherein the catalyst is:
   (a) a water-soluble catalyst, such as a water-soluble free radical-generating azo compound; 2,2'-azobis[2-(2-imidazolin-2-yl)propane]dihydrochloride (Vazo 44 or VA-044); 2,2'-azobis(2-amidinopropane) dihydrochloride (AAPH); metals or metal ions having photoinitiator activity; a peroxide; tert-butyl hydroperoxide; benzoylperoxide; ammonium persulfate; or any derivative thereof having photoinitiator activity; or
   (b) a water-insoluble catalyst, such as a water-insoluble free radical-generating azo compound, 2,2-dimethoxy-2-phenylacetophenone (DMPA), azobisisobutyronitrile (AIBN), 2,2'-azobis(2-methylpropionitrile), 4,4'-Azobis(4-cyanopentanoic acid) (ACVA), 1,1'-azobis(cyanocyclohexane) (ACHN), diazenedicarboxylic acid bis (N,N-dimethylamide) (TMAD); azodicarboxylic acid dipiperidide (ADD), or any derivative thereof having photoinitiator activity.

7. The method of any one of items 1 to 6, wherein said photocatalytic thiol-ene reaction comprises irradiation under short-wave ultraviolet light.

8. The method of item 7, wherein said photocatalytic thiol-ene reaction comprises irradiation at about 254 nm.

9. The method of any one of items 1 to 6, wherein said photocatalytic thiol-ene reaction comprises irradiation under long-wave ultraviolet light.

10. The method of item 9, wherein said photocatalytic thiol-ene reaction comprises irradiation at about 355 nm or 365 nm.

11. The method of any one of items 1 to 10, wherein said photocatalytic thiol-ene reaction comprises reacting between 1 to 200 molar equivalents of the alkenyl carbohydrate antigen per free thiol group of the carrier protein; and/or wherein said photocatalytic thiol-ene reaction is performed for 10 to 300, 10 to 270, 10 to 240, 10 to 210, 10 to 180, 10 to 150, 10 to 120, 10 to 90, 10 to 60, or 10 to 30 minutes, and/or for a sufficient time to achieve at least a 5, 10, 15, 20, 25, 30, 35, 40, 45, or 50-fold reduction in total free thiol concentration in the carrier protein.

12. The method of any one of items 1 to 11, wherein said photocatalytic thiol-ene reaction is performed at a pH between about 3.0, 3.1, 3.2, 3.3, 3.4, 3.5, 3.6, 3.7, 3.8, 3.9, or 4.0, and about 4.5, 4.6, 4.7, 4.8, 4.9, 5.0, 5.5, 6.0, 6.5, 7.0, 7.5, 8.0, 8.5, 9.0, 9.5, or 10, and/or at a pH that avoids carrier protein denaturation.

13. The method of any one of items 1 to 12, wherein said carbohydrate antigen, following conjugation to the carrier protein, is not cleavable from the carrier protein by an endogenous enzyme of the subject.

14. The method of any one of items 1 to 13, wherein said alkenyl carbohydrate antigen is covalently linked to the terminal alkene, and/or the carbohydrate antigen is conjugated to the carrier protein, via a glycosidic bond, such as is an O-glycosidic bond, an S-glycosidic bond, an N-glycosidic bond, or a C-glycosidic bond, or a bond obtained by reductive amination, such as between an allyl amine and a reducing sugar.

15. The method of any one of items 1 to 14, wherein the carbohydrate antigen comprises a B cell epitope, and/or induces a humoral immune response in the subject; and/or comprises T cell epitope, and/or induces a cell-mediated immune response in the subject.

16. The method of any one of items 1 to 15, wherein the carbohydrate antigen is or comprises a tumor associated carbohydrate antigen (TACA).

17. The method of item 16, wherein the TACA is, is from, or comprises: Tn, S-Tn, Thomsen-Friedenreich (TF), (2,3)-S-TF, (2,6)-S-TF, Globo H, GD2, GD3, GM2, GM3, N-glycolyl-GM3, Lea, sLea, Lex, sLex, or any combination thereof.

18. The method of any one of items 1 to 17, wherein said photocatalytic thiol-ene reaction conjugates at least two of the same carbohydrate antigen or more than one type of carbohydrate antigen to the carrier protein, thereby producing a multi-valent glycoconjugate immunogen.

19. The method of item 18, wherein said multi-valent glycoconjugate immunogen comprises 2, 3, 4, 5, 6, 7, 8, 9, 10, 11, 12, 13, 14, 15, or more of the same or different types of carbohydrate antigens conjugated to the carrier protein.

20. The method of any one of items 1 to 19, wherein the carbohydrate antigen is or comprises a viral polysaccharide antigen, or a bacterial capsular polysaccharide (CPS).

21. The method of item 20, wherein the bacterial CPS is, is from, or comprises a Pneumococcal and/or Streptococcal polysaccharide serotype, meningococcal CPS, or influenza (such as influenza type a or b) CPS.

22. The method of any one of items 1 to 21, wherein the carbohydrate antigen in (a) is linked to the terminal alkene via a linker.

23. The method of any one of items 1 to 22, wherein the carrier protein comprises one or more cysteine residues having the one or more free thiol groups, or optionally is engineered to add one or more further cysteine residues, for example at the amino terminus, the carboxy terminus, or a solvent-accessible position of the carrier protein.

24. The method of any one of items 1 to 23, wherein the carrier protein comprises a human T cell epitope, and/or induces a cell-mediated immune response in the subject.

25. The method of any one of items 1 to 24, wherein the carrier protein is, is from, or comprises: Tetanus Toxoid (TT), Diphtheria Toxoid (DT), cross-reacting material 197 (CRM197), Meningococcal Outer Membrane Protein Complex (OMPC), H. Influenzae Protein D (HiD), a cytokine, an immunogenic peptide such as Tetanus Toxin 831-844 (SEQ ID NO: 1 or 2), albumin (such as bovine serum albumin or human serum albumin), or an immunogenic fragment thereof.

26. The method of any one of items 1 to 25, wherein:
   (i) the carrier protein, prior to or together with performing the photocatalytic thiol-ene reaction, is pre-treated with a reducing agent, such as dithiothreitol (DTT), tris(2-carboxyethyl)phosphine (TCEP), 2-mercaptoethylamine-HCl, or 2-mercaptoethanol;
   (ii) the carrier protein, prior to or together with performing the photocatalytic thiol-ene reaction, is pre-treated with a thiolating agent, such as 2-iminothiolane or N-hydroxysuccinimide dithiopropionate (DPS);
   (iii) the carrier protein, prior to or together with performing the photocatalytic thiol-ene reaction, is pre-treated with a thiolating agent, such as 2-iminothiolane or N-hydroxysuccinimide dithiopropionate (DPS), and subsequently pre-treated with a reducing agent;
   (iv) the carrier protein is a protein having one or more disulfide bridges, and wherein the one or more disulfide bridges remain unaffected following said photocatalytic thiol-ene reaction;
   (v) the carrier protein is a protein having one or more disulfide bridges, and wherein the carrier protein is pre-treated with a reducing agent to expose one or more additional free thiol groups for conjugation to the carbohydrate antigen; or
   (iv) the carrier protein is a protein having one or more disulfide bridges, and wherein the carrier protein is pre-treated with a thiolating agent (such as 2-iminothiolane or N-hydroxysuccinimide dithiopropionate (DPS)) to expose one or more additional free thiol groups for conjugation to the carbohydrate antigen, and subsequently pre-treated with a reducing agent.

27. The method of any one of items 1 to 26, wherein the total number of carbohydrate antigens comprised in the glycoconjugate immunogen is equal to the number of free thiol groups available on the carrier protein prior to conjugation.

28. The method of any one of items 1 to 27, wherein the glycoconjugate immunogen induces a cell-mediated immune response to the carbohydrate antigen upon administration to the subject.

29. The method of any one of items 1 to 28, further comprising: (d) purifying the glycoconjugate immunogen.

30. A method for producing a glycoconjugate vaccine or an adaptive immune response-triggering composition, the method comprising formulating the glycoconjugate immunogen prepared by the method of any one of items 1 to 29 with a pharmaceutically acceptable excipient, and/or an adjuvant.

31. The method of item 30, wherein the adjuvant is or comprises: an inorganic compound, a mineral oil, a microbial derivative, a plant derivative, a cytokine, squalene, alum, aluminum hydroxide, aluminum phosphate, calcium phosphate hydroxide, a toll-like receptor agonist, an immunostimulatory polynucleotide (such as CPG), an immunostimulatory lipid, Freund's adjuvant, RIBI's adjuvant, QS-21, muramyl dipeptide, TiterMax, Steviune, Stimune, or any combination thereof.

32. A synthetic glycoconjugate immunogen comprising one or more carbohydrate antigens and an immunogenic carrier protein having one or more solvent-accessible cysteine residues, wherein the one or more carbohydrate antigens are linked to the immunogenic carrier protein at the one or more solvent-accessible cysteine residues, and wherein conjugation of the one or more carbohydrate antigens to the immunogenic carrier protein increases the immunogenicity of the one or more carbohydrate antigens upon administration to a subject, as compared to administration of the unconjugated carbohydrate antigen.

33. The synthetic glycoconjugate immunogen of item 32, wherein the one or more carbohydrate antigens are linked to the one or more solvent-accessible cysteine residues via a linker.

34. The synthetic glycoconjugate immunogen of item 32, wherein the one or more carbohydrate antigen is linked to the linker via a bond as defined in item 13 or 14.

35. The synthetic glycoconjugate immunogen of any one of items 32 to 34, wherein the one or more carbohydrate antigens is/are as defined in item 2, 15, 16, 17, 20, or 21.

36. The synthetic glycoconjugate immunogen of any one of items 32 to 35, which is the multi-valent glycoconjugate immunogen as defined in item 18 or 19.

37. The synthetic glycoconjugate immunogen of any one of items 32 to 36, wherein the carrier protein is as defined in item 23, 24, 25, or 26.

38. The synthetic glycoconjugate immunogen of any one of items 32 to 37, wherein the total number of carbohydrate antigens comprised in the glycoconjugate immunogen is equal to the number of solvent-accessible cysteine residues on the carrier protein.

39. The synthetic glycoconjugate immunogen of any one of items 32 to 38, which induces a cell-mediated immune response to the carbohydrate antigen upon administration to the subject.

40. The synthetic glycoconjugate immunogen of any one of items 32 to 39, which is prepared by the method of any one of items 1 to 29.

41. A glycoconjugate vaccine produced by the method of item 30 or 31, and/or comprising the synthetic glycoconjugate immunogen of any one of items 32 to 40, and a pharmaceutically acceptable excipient, and/or an adjuvant.

42. The glycoconjugate vaccine of item 41, which is a prophylactic vaccine or a therapeutic vaccine.

43. A method of immunizing, vaccinating, or treating a subject comprising administering to the subject the glycoconjugate immunogen produced by the method of any one of items 1 to 29, the glycoconjugate vaccine produced by the method of item 30 or 31, the synthetic glycoconjugate immunogen of any one of items 32 to 40, or the glycoconjugate vaccine of item 41 or 42.

44. The synthetic glycoconjugate immunogen of any one of items 32 to 40, or the glycoconjugate vaccine of item 41 or 42, for use in immunizing, vaccinating, or treating a subject having a disease, or for detecting the presence of an antibody that specifically binds to the glycoconjugate or for detecting said immunization, vaccination, or treatment (e.g., in a biological sample from the subject).

45. A synthetic glycoconjugate immunogen comprising one or more sugar antigens covalently linked to one or more free thiol groups of a carrier protein via a linker, wherein each linker has the structure:

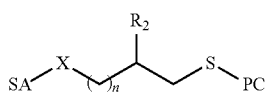

wherein:
SA is a sugar antigen or a portion thereof;
S—PC is a carrier protein;
X is O, S, NR$_1$, or CH$_2$;
R$_1$ is —H, —COH, —COCH$_3$, or —COEt;
n is 1, 2, 3, 4, or 5; and
R$_2$ is H or Me;
or a stereoisomer thereof.

46. A synthetic glycoconjugate immunogen comprising one or more sugar antigens covalently linked to one or more free thiol groups of a carrier protein via a linker, wherein each linker has the structure:

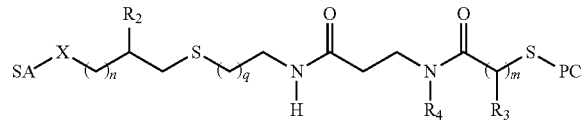

wherein:
SA is a sugar antigen or a portion thereof;
S—PC is a carrier protein;
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5;
R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1;
or a stereoisomer thereof.

47. A synthetic glycoconjugate immunogen comprising one or more sugar antigens covalently linked to one or more free thiol groups of a carrier protein via a linker, wherein the synthetic glycoconjugate immunogen has the structure:

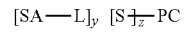

wherein
y is at least 1;
SA is selected from the group consisting of one or more sugar antigens or immunogenic portions thereof, and when y is more than 1, SA are identical or different;

[S]$_z$—PC is a carrier protein having one or more sulfur atoms originating from the one or more free thiol groups;
z is at least 1 and is at least equal to y; and
L is a linker selected from the group consisting of linkers having the structure:

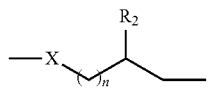

wherein:
X is O, S, NR$_1$, or CH$_2$;
R$_1$ is —H, —COH, —COCH$_3$, or —COEt;
n is 1, 2, 3, 4, or 5; and
R$_2$ is H or Me; and
when y is more than 1, L are identical or different;
or a stereoisomer thereof.

48. A synthetic glycoconjugate immunogen comprising one or more sugar antigens covalently linked to one or more free thiol groups of a carrier protein via a linker, wherein the synthetic glycoconjugate immunogen has the structure:

wherein
y is at least 1;
SA is selected from the group consisting of sugar antigens or immunogenic portions thereof, and when y is more than 1, SA are identical or different;
[S]$_z$—PC is a carrier protein having one or more sulfur atoms originating from z free thiol groups;
z is at least equal to y; and
L is a linker selected from the group consisting of linkers having the structure:

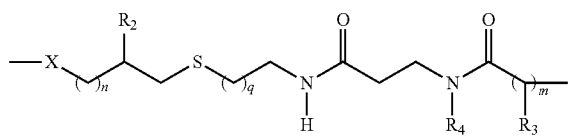

wherein:
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5;
R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; and
when y is more than 1, L are identical or different;
or a stereoisomer thereof.

49. A synthetic glycoconjugate immunogen comprising one or more sugar antigens covalently linked to one or more free thiol groups of a carrier protein via a linker, wherein the synthetic glycoconjugate immunogen has the structure:

wherein
y is at least 1;
SA is selected from the group consisting of sugar antigens or immunogenic portions thereof, and when y is more than 1, SA are identical or different;
[S]$_z$—PC is a carrier protein having one or more sulfur atoms originating from z free thiol groups;
z is at least equal to y; and
L is a linker selected from the group consisting of linkers having the structure:

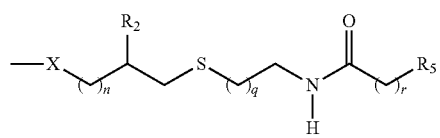

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5;
r is 1, 2, 3, 4 or 5;
R$_5$ is S—PC, a covalent bond, or a radical of structure:

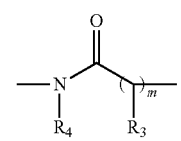

wherein R$_3$ and R$_4$ are each a hydrogen atom and m is 1, 2, 3, 4 or 5, or R$_3$ and R$_4$ form together a radical —CO—CH$_2$— or a radical —CO—CH$_2$—CH$_2$— with the carbonyl linked to the nitrogen atom, and m is 1; and
when y is more than 1, L are identical or different;
or a stereoisomer thereof.

50. The synthetic glycoconjugate immunogen of item 49, wherein the linker has the structure:

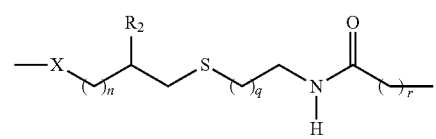

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5; and
r is 1, 2, 3, 4 or 5.

51. The synthetic glycoconjugate immunogen of item 49, wherein the linker has the structure:

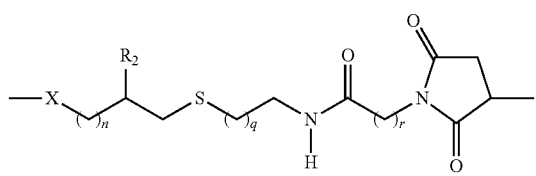

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5; and
r is 1 or 2.

52. The synthetic glycoconjugate immunogen of item 49, wherein the linker has the structure:

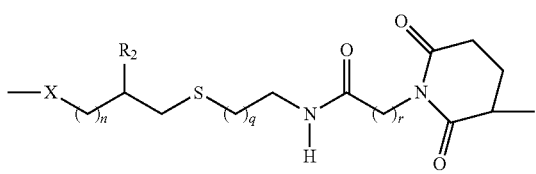

wherein
X is S, NR$_1$, CH$_2$ or O;
R$_1$ is —H, —COH, —COMe, or —COEt;
n is 1, 2, 3, 4, or 5;
R$_2$ is H or Me;
q is 1, 2, 3, 4, or 5; and
r is 1 or 2.

53. The synthetic glycoconjugate immunogen of any one of items 47 to 52, wherein y is an integer varying from 1 to 50, 1 to 40, 1 to 30, 1 to 20, or 1 to 10.

54. The synthetic glycoconjugate immunogen of any one of items 45 to 53, wherein said sugar antigen is the carbohydrate antigen as defined in item 15, 16, 17, 20, or 21.

55. The synthetic glycoconjugate immunogen of any one of items 45 to 54, wherein said carrier protein is the carrier protein as defined in item 23, 24, or 25.

56. The synthetic glycoconjugate immunogen of any one of items 45 to 55, which is a multi-valent glycoconjugate immunogen.

57. The synthetic glycoconjugate immunogen of item 56, wherein said multi-valent glycoconjugate immunogen comprises 2, 3, 4, 5, 6, 7, 8, 9, 10, 11, 12, 13, 14, 15, or more of the same or different types of carbohydrate antigens conjugated to the carrier protein.

58. The synthetic glycoconjugate immunogen of any one of items 45 to 57, wherein the glycoconjugate immunogen induces a cell-mediated immune response to the carbohydrate antigen upon administration to a subject.

59. A vaccine comprising the synthetic glycoconjugate immunogen of any one of items 45 to 58, and a pharmaceutically acceptable excipient and/or an adjuvant.

60. The vaccine of item 59, wherein the adjuvant is as defined in item 31.

61. Use of the glycoconjugate immunogen prepared by the method of any one of items 1 to 29, or the synthetic glycoconjugate immunogen as defined in any one of item 32 to 40 and 45 to 58, for the manufacture of a vaccine.

62. Use of the glycoconjugate immunogen prepared by the method of any one of items 1 to 29, the glycoconjugate vaccine produced by the method of item 30 or 31, the synthetic glycoconjugate immunogen as defined in any one of item 32 to 40 and 45 to 58, or the vaccine of item 59 or 60, for the treatment of a subject having a disease associated with increased expression of said one or more carbohydrate or sugar antigens.

63. Use of the glycoconjugate immunogen prepared by the method of any one of items 1 to 29, the glycoconjugate vaccine produced by the method of item 30 or 31, the synthetic glycoconjugate immunogen as defined in any one of item 32 to 40 and 45 to 58, or the vaccine of item 59 or 60, for producing an antibody that specifically binds to the glycoconjugate immunogen.

64. Use of the glycoconjugate immunogen prepared by the method of any one of items 1 to 29, the glycoconjugate vaccine produced by the method of item 30 or 31, the synthetic glycoconjugate immunogen as defined in any one of item 32 to 40 and 45 to 58, for detecting an antibody that specifically binds to the glycoconjugate immunogen.

65. A method for producing a glycoconjugate, the method comprising:
(a) providing a carbohydrate antigen covalently linked to a terminal alkene (alkenyl carbohydrate antigen), the terminal alkene being directly conjugatable to a thiol group via a thiol-ene reaction;
(b) providing a conjugate material suitable for conjugation to the carbohydrate antigen via a thiol-ene reaction as described herein, said conjugate material having one or more free thiol groups; and
(c) performing a photocatalytic thiol-ene reaction to directly conjugate the carbohydrate antigen to the conjugate material at the one or more free thiol groups, thereby producing the glycoconjugate.

66. The method of item 65, wherein the conjugate material is or comprises a polymer, a polypeptide, a carrier protein as defined in any one of preceding items, a solid support, a particle, or any other material having a free thiol group suitable for conjugation to the carbohydrate antigen via a thiol-ene reaction as described herein.

67. The method of item 65 or 66, further comprising one or more features a defined in any one of items 1 to 64.

68. Use of a glycoconjugate produced by the method of any one of items 65 to 67, for detecting or screening for the presence of an antibody that specifically binds to a carbohydrate antigen or a tumor-circulating cell comprising a carbohydrate antigen, or for detecting the presence of antibodies resulting from an immunization or vaccination with a carbohydrate antigen.

69. The use of item 68, wherein the detection or screening is performed via any suitable detection method such as an immunosorbent assay, ELISA, microarray, or immunoblot analysis.

70. A method of treating a subject comprising administering a glycoconjugate or glycoconjugate immunogen as defined in any preceding items or produced by a method as defined by any preceding items, to generate an immune response in said subject to a carbohydrate antigen, and screening a biological sample from said subject for the presence of antibodies that specifically binds to the carbohydrate antigen.

71. The method of items 70, further comprising one or more features as described in preceding items.

EXAMPLES

Example 1: General Methods

Reactions were carried out under argon atmosphere using commercially available HPLC grade. Commercially available reagents (Sigma Aldrich) were used without further purification. N-Acetyl-D-galactosamine and N-acetyl-neuraminic acid were provided from Rose Scientific Ltd. Alberta, Canada. The Fmoc-β-Ala-Wang resin and Fmoc amino acid were available commercially from Peptide Technologies Ltd, Pierrefonds, Qc, Canada. Progress of reactions was monitored by thin-layer chromatography using silica gel 60 $F_{254}$ coated plates (E. Merck). The conjugation by the click thiol-ene photoreaction was done in a quartz cuvette (10×10 mm path length, Fisher Scientific Canada, Cat. No. 14-958-130) place between two hand held UV 365 nm lamps (UV-AC Hand Lamp, Dual 254/365 nm UV; 115V-60 Hz, 0.16 amps, VWR Canada, Cat. No. 89131-492). Flash chromatography was performed using ZEOprep™ silica gel 60 (40-63 µm) from Canadian Life Science. Detection was carried out under UV light or by spraying with 20% ethanolic sulfuric acid or molybdate or $KMnO_4$ solution followed by heating. NMR spectra were recorded on Bruker ULTRASHIELD™ 300 MHz and Bruker Avance™ III HD 600 MHz spectrometers. Proton and carbon chemical shifts (δ) are reported in ppm relative to the chemical shift of residual $CHCl_3$, which was set at 7.26 ppm ($^1H$) and 77.16 ppm ($^{13}C$). Coupling constants (J) are reported in Hertz (Hz), and the following abbreviations are used for peak multiplicities: singlet (s), doublet (d), doublet of doublets (dd), doublet of doublet with equal coupling constants ($t_{ap}$), triplet (t), multiplet (m). Analysis and assignments were made using COSY (Correlated SpectroscopY) and HSQC (Heteronuclear Single Quantum Coherence) experiments. High-resolution mass spectra (HRMS) were measured with a LC-MS-TOF (Liquid Chromatography Mass Spectrometry Time Of Flight) instrument from Agilent technologies in positive and/or negative electrospray mode by the analytical platform of UQAM. Either protonated ions $(M+H)^+$ or sodium adducts $(M+Na)^+$ were used for empirical formula confirmation. The native TT and TT-conjugate were dialyzed using 2000 KDa benzoylated dialysis tubing (Sigma-Aldrich (Ontario, Canada). The thiol contents of both native and conjugated TT were determined by the Ellman test at 412 nm (Ellman, G. L. Arch. Biochem. Biophys. 1959, 82, 70-77). The total sugar content of the TT-conjugate was determined by the colorimetric DuBois test measured at 492 nm (Dubois, M.; Gilles, K. A.; Hamilton, J. K.; Rebers, P. A.; Smith, F. Colorimetric Method for Determination of Sugars and Related Substances. Anal. Chem., 1956, 28, 350-356) using a UV/VIS Ultrospec 100 prot spectrophotometer (Biochrom, USA). Dynamic Light Scattering (DLS), particle size distributions were measured in PBS using a Zetasizer Nano S90 from Malvern. The mouse monoclonal IgG3 antibody JAA-F11 was produced as previously described in Rittenhouse-Diakun et al., 1998.

General Solid Phase Peptide Synthesis (SPPS) Procedure

The procedure of Solid-Phase Peptide Synthase (SPPS) was followed under literature procedure (Papadopoulos et al., 2012) and stared with Fmoc-β-Ala-Wang resin (650 mg, 0.34 mmol, 1.0 equiv.; 100-200 mesh, loading=0.52 mmol/g). The reactions were conducted by rotation agitation in Econo-Pac disposable columns 1.5×14 cm (20 mL) (Bio-Rad Laboratories, ON, Canada). The resin was swollen in $CH_2Cl_2$ during 1 h, then filtered and reconditioned in DMF during i 1. The Fmoc-protecting group of the commercial resin or of amino acids were removed with a solution of 20% piperidine in DMF (5 mL, 2×5 min then 1×10 min). The solvents and reagents were removed by filtration, and the resin was washed with DMF, $CH_2Cl_2$ and MeOH (3× with each solvent). The presence of free amino groups was verified by a Kaiser test or TNBS test. The free amines on the resin were treated with a solution de preactivated Fmoc amino acid: 3 equiv of amino acid, 3 equiv of HBTU (N,N,N',N'-Tetramethyl-O-(1H-benzotriazol-1-yl)uronium hexafluorophosphate) and a catalytic amount of HOBt (1-hydroxybenzotriazole) in DMF at 4° C. (10 min). DIPEA (Diisopropylamine, 9 equiv) was then added into the mixture and stirred at room temperature for 1 h 30 min. Completion of the coupling was determined using Kaiser or a TNBS colorimetric test. After filtration, the resin was washed and the Fmoc removal procedure was again repeated. At the end of the synthetic sequences, the last free amine was capping by acetylation ($Ac_2O$/DIPEA/DMF 1:1:8, 1 h). After filtration, the solutions were drained off, the resin was dried under vacuum and the cleavage was carried out using trifluoroacetic acid/water/ethanedithiol/triisopropylsilane (94.0/2.5/2.5/1.0) for 3 h. The resulting peptide was precipitated with methyl tert-butyl ether and isolated from the resin bead by centrifugation (20 min, 2000 rpm, 3×). The precipitates were dried carefully with a stream of air jet. The crud peptide was solubilised in $H_2O$ to separated from resin. The solution was then lyophilized to afford desire peptide.

dTT831-844-Cys-βAla.

From Fmoc-β-Ala-Wang resin (650 mg, 0.34 mmol, 1.0 equiv.; 100-200 mesh, loading=0.52 mmol/g), the desire peptide dTT831-844-Cys-βAla was isolated as white power (62 mg, 0.034 mmol, 10%). ESI$^+$-LC-MS: [M+2H]$^{+2}$ calcd for $C_{83}H_{135}O_{24}N_{19}S$, 906.9819. found, 906.9849. CAN/$H_2O$ 5 to 95% 5.42 min.

Cys-dTT831-844-βAla.

From Fmoc-β-Ala-Wang resin (650 mg, 0.34 mmol, 1.0 equiv.; 100-200 mesh, loading=0.52 mmol/g), the desire peptide Cys-dTT831-844-βAla was isolated as white power (62 mg, 0.034 mmol, 10%). ESI$^+$-LC-MS: [M+2H]$^{+2}$ calcd for $C_{83}H_{135}O_{24}N_{19}S$, 906.9819. found, 906.9844. CAN/$H_2O$ 5 to 95% 5.32 min Example 2: Allyl 2-acetamido-3,6-di-O-pivaloyl-2-deoxy-α-D-glucopyranoside (Compound 2)

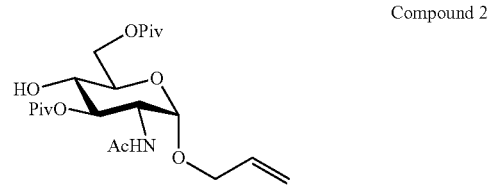

Compound 2

Figure 5:
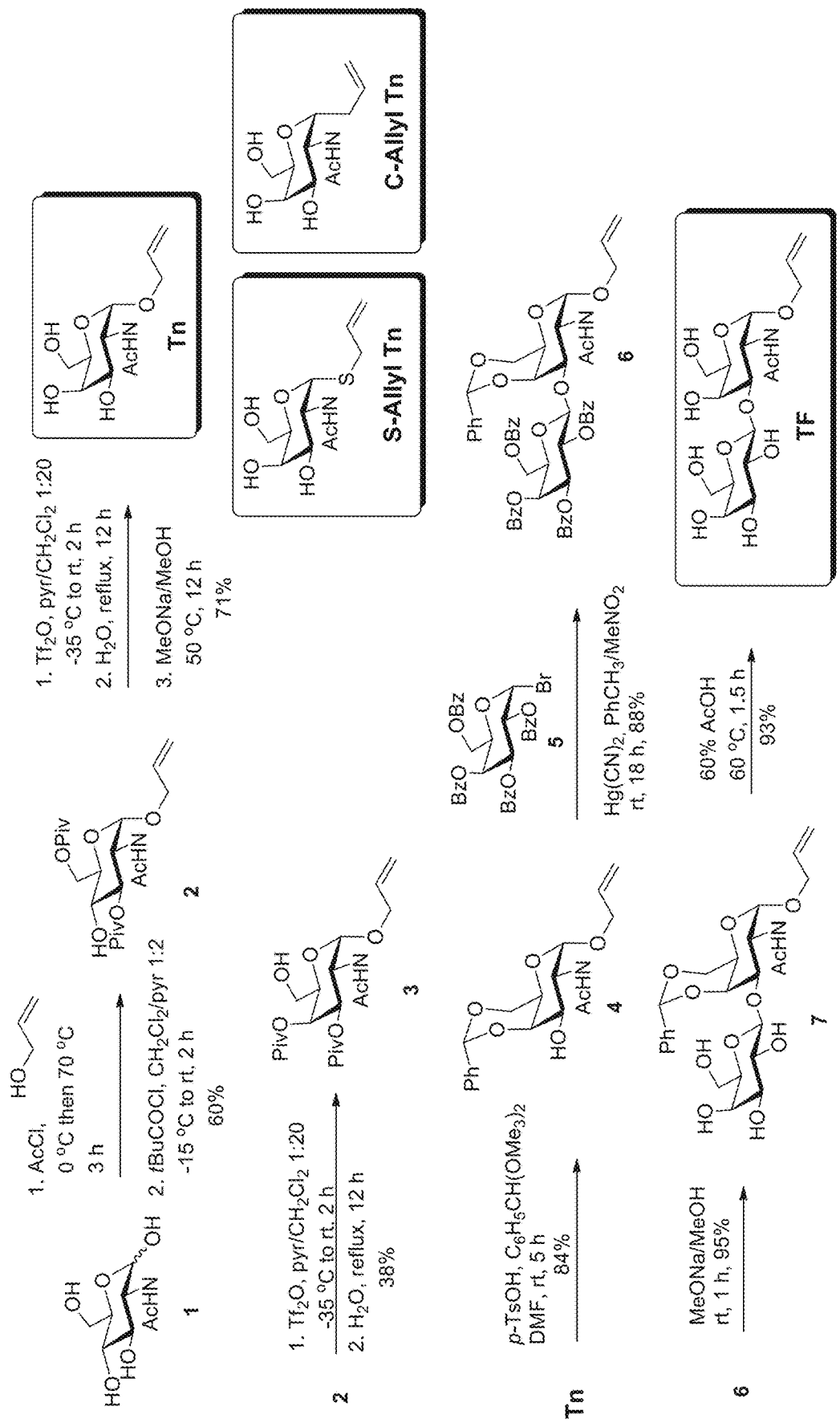
FIG. 5 shows reaction schemes for the syntheses of allyl Tn antigen and allyl TF antigen ready for conjugation to carrier proteins, as described in Examples 2-6.
Figures 6A, 6B:
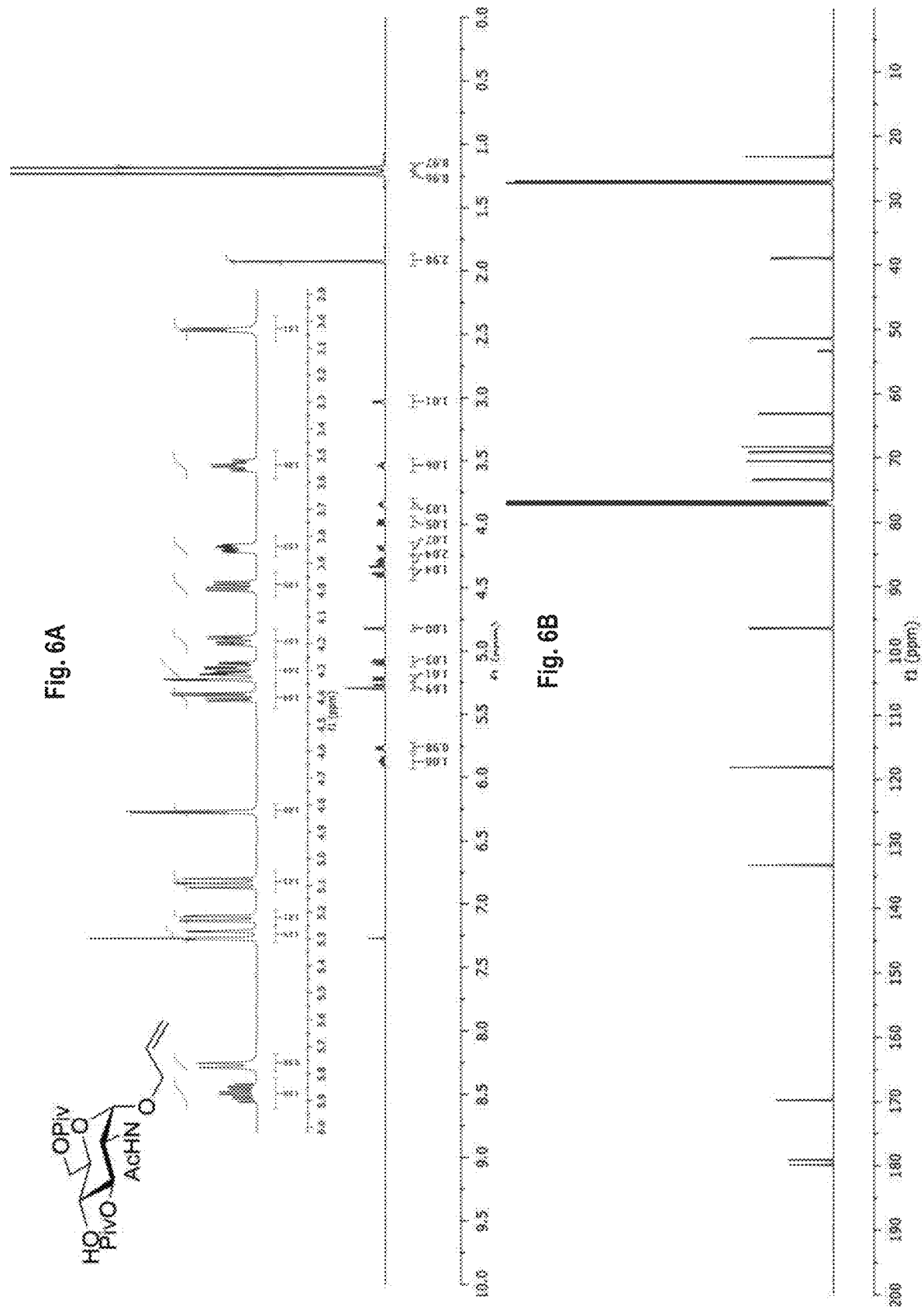
FIG. 6A-6D shows the $^1$H-NMR (FIG. 6A) and $^{13}$C-NMR (FIG. 6B) spectra, as well as mass spectrometry results (FIGS. 6C and 6D) for allyl 2-acetamido-3,6-di-O-pivaloyl-2-deoxy-α-D-glucopyranoside (Compound 2).
Figure 6C:
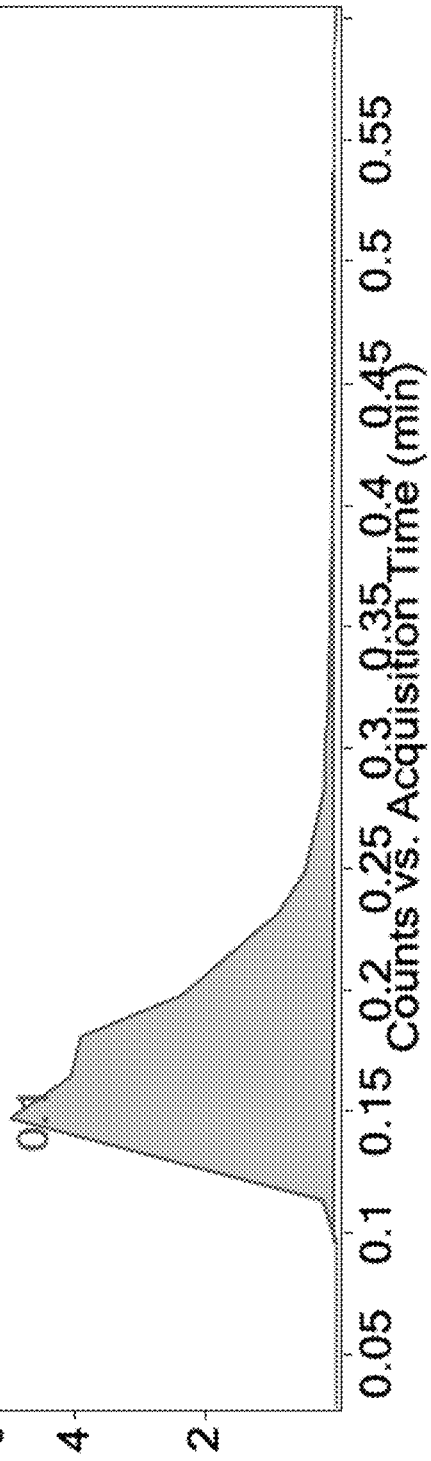
Figure 6D:
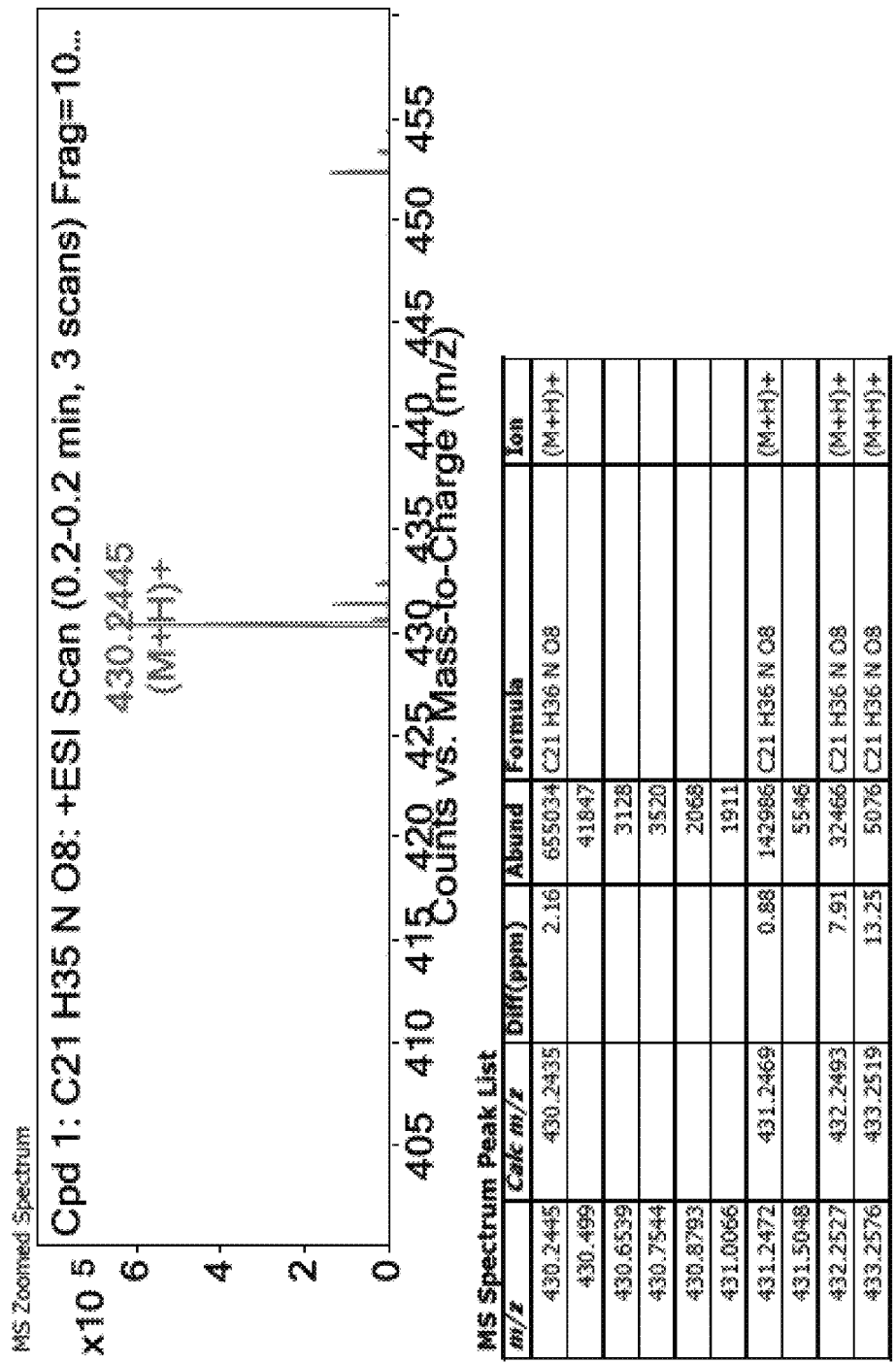

Referring to FIG. 5, Acetyl chloride (2.76 mL, 38.80 mmol, 3.43 equiv.) was added dropwise to allylic alcohol (20.8 mL) at 0° C. under argon atmosphere. At room temperature, N-acetyl-D-glucosamine (Compound 1) (2.50 g, 11.3 mmol, 1.00 eq.) was added. The reaction mixture was stirred at 70° C. for 3 hours, then quenched by adding solid $NaHCO_3$ until pH 7. The suspension was filtered through out a pad of Celite, washing several times with MeOH. The solvent was removed under reduced pressure, and the crude allyl 2-acetamido-2-deoxy-D-glucosamine was precipitated by trituration with $Et_2O$/Ethanol. The solvent was then removed under reduced pressure several times after trituration. To a suspension of crude allyl 2-acetamido-2-deoxy-α-D-glucopyranoside intermediate, in the mixture of dry dichloromethane-pyridine (45 mL, v/v, 1:2) under nitrogen atmosphere at −15° C., pivaloyl chloride (3.90 mL, 31.64 mmol, 2.80 equiv.) was then added dropwise. The reaction mixture was stirred for 2 hours warned to room temperature to give the desired α-anomer (Compound 2) (Rf=0.32) together with some β-anomer (Rf=0.18); hexanes/EtOAc 1:1). The mixture was diluted then with $CH_2Cl_2$ and the organic phase was successively washed with HCl (1M) several times, saturated aqueous solution of $KHSO_4$, saturated solution of $NaHCO_3$, and brine. The organic phase was dried over $Na_2SO_4$, filtered and evaporated under reduced pressure. The yellowish oil was purified by flash chromatography on silica gel (Hexane-EtOAc 6:4 to 1:1) to afford the desired compound allyl 2-acetamido-3,6-di-O-pivaloyl-2-deoxy-α-D-glucopyranoside (Compound 2) as white solid (4.85 g, 6.78 mmol, 60%). Rf=0.32; hexanes/EtOAc 1:1; FIGS. 6A & 6B: $^1H$ NMR ($CDCl_3$, 600 MHz): δ 5.87 (dddd, 1H, $J_{H,H}$=16.8, 10.5, 6.2, 5.3 Hz, $OCH_2CH=CH_2$), 5.77 (d, 1H, $J_{NH,H2}$=9.7 Hz, NH), 5.31-5.25 (m, 1H, $OCH_2CH=CH_2$), 5.22 (dd, 1H, $J_{H,H}$=10.4, 1.3 Hz, $OCH_2CH=CH_2$), 5.09 (dd, 1H, $J_{3,4}$=10.7, $J_{2,3}$=9.3 Hz, H-3), 4.83 (d, 1H, $J_{1,2}$=3.7 Hz, H-1), 4.39 (m, 1H, H-6a), 4.35-4.25 (m, 2H, H-6b and H-2), 4.19 (m, 1H, $OCH_2$), 4.02-3.93 (m, 1H, $OCH_2$), 3.85 (m, 1H, H-5), 3.59-3.48 (m, 1H, H-4), 3.03 (d, 1H, $J_{4,OH}$=5.1 Hz, OH-4), 1.93 (s, 3H, $NHCOCH_3$), 1.23 (s, 9H, tert-Butyl) and 1.19 ppm (s, 9H, tert-Butyl); $^{13}C$ NMR ($CDCl_3$, 150 MHz): δ 179.8, 179.1 (tert-BuCO), 169.7 (NHCO), 133.2 ($OCH_2CH=CH_2$), 118.1 ($OCH_2CH=CH_2$), 96.4 (C-1), 73.4 (C-3), 70.5 (C-5), 69.1 (C-4). 68.2 ($OCH_2$), 63.1 (C-6), 51.4 (C-2), 39.0, 38.9 (2×$C(CH_3)_3$), 27.2, 27.0 (2×$C(CH_3)_3$) and 23.2 ppm ($CH_3$). FIGS. 6C & 6D: ESI$^+$-HRMS: [M+H]$^+$ calcd for $C_{21}H_{36}O_8N$, 430.2435. found, 430.2445. The β-anomer was isolated as white solid (971 mg, 2.26 mmol, 20%). Rf=0.18; hexanes/EtOAc 1:1; $^1H$ NMR ($CDCl_3$, 300 MHz): δ 6.00 (d, 1H, $J_{NH,H2}$=9.3 Hz, NH), 5.95-5.75 (m, 1H, $OCH_2CH=CH_2$), 5.35-5.03 (m, 3H, $OCH_2CH=CH_2$ and H-3), 4.55 (d, 1H, $J_{1,2}$=8.4 Hz, H-1), 4.47-425 (m, 3H, H-6a, 6b and $OCH_2$), 4.14-3.90 (m, 2H, $OCH_2$ and H-2), 3.65-3.43 (m, 2H, H-5 and H-4), 3.23 (sb, 1H, OH-4), 1.92 (s, 3H, $NHCOCH_3$), 1.23 (s, 9H, tert-Butyl) and 1.20 ppm (s, 9H, tert-Butyl).

Example 3: Allyl 2-acetamido-2-deoxy-α-D-galactopyranoside (Allyl Tn)

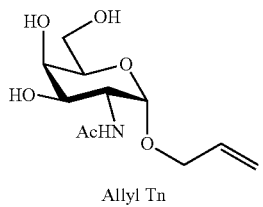

Allyl Tn

Figure 7C:
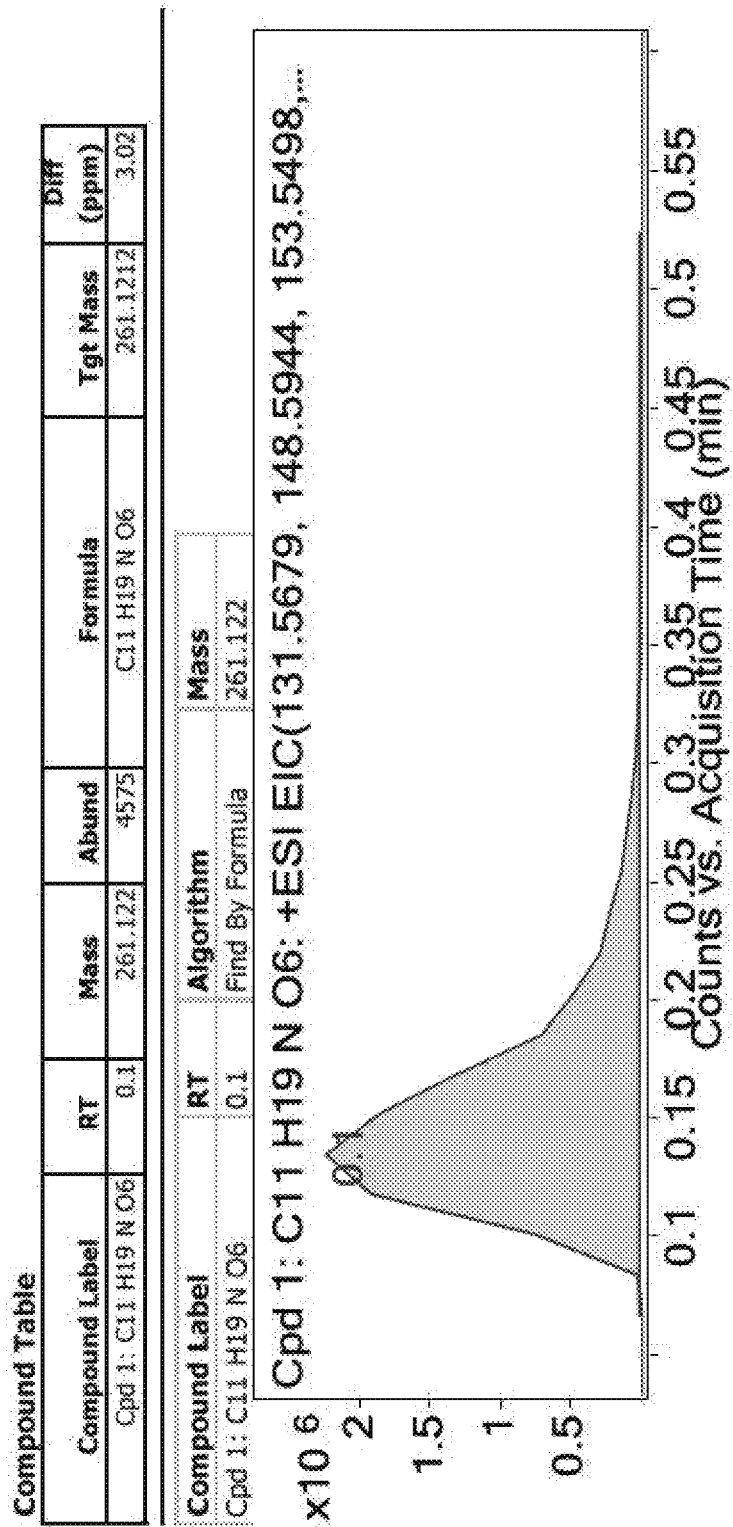
Figure 7D:
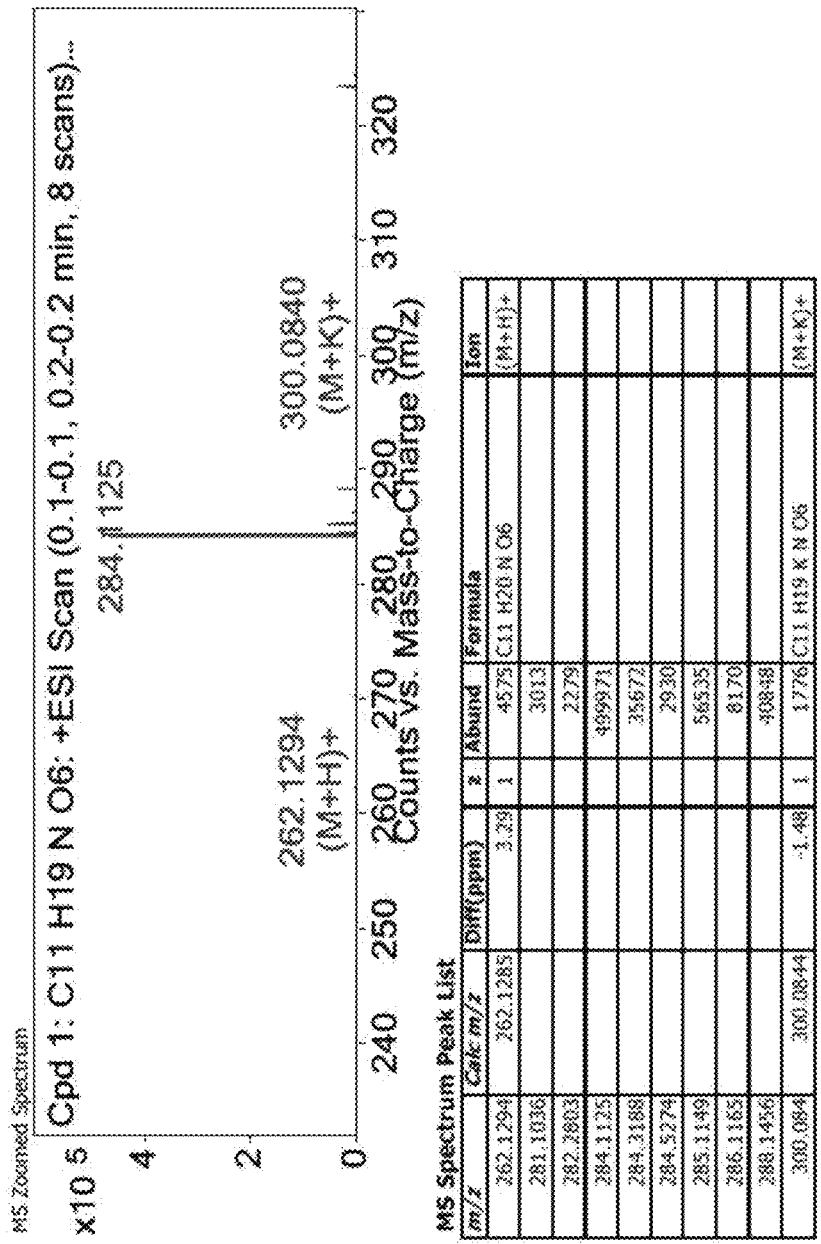

Referring to FIG. 5, di-O-pivaloyl compound (Compound 2) (5.50 g, 12.80 mmol, 1.0 equiv.) in a mixture of dry dichloromethane-pyridine (126 mL, v/v 20:1) was cooled to −35° C. under argon atmosphere. Trifluoromethanesulfonic anhydride (2.58 mL, 15.36 mmol, 1.2 equiv.) was then added and the mixture was stirred at this temperature. The temperature was warned to room temperature for 2 hours. Water (12 mL) was then added into the solution. The mixture was heated, and stirred at reflux 50° C.) overnight (12 hours). After reaching room temperature, the reaction mixture was diluted with dichloromethane and washed with 1M aqueous HCl several times. The organic layer was washed with $H_2O$, saturated $NaHCO_3$, and brine. The organic layer was dried over $Na_2SO_4$, filtered and evaporated under reduced pressure. The crude product was treated under Zemplén condition (1M sodium methoxide solution in methanol, 40 mL, pH 9). The solution was stirred at 50° C. overnight. After cooling to room temperature, the solution was neutralized by addition on ion-exchange resin (Amberlite® IR 120H$^+$), filtered, washed with MeOH, and the solvent was removed under reduced pressure. Allyl $T_N$ was isolated by precipitation in MeOH/EtOAc/Hexanes as white solid after lyophilisation (2.36 g, 9.10 mmol, 71%). Rf=0.32; EtOAc/MeOH 4:1; FIGS. 7A & 7B: $^1H$ NMR ($CD_3OD$, 600 MHz): δ 5.99-5.88 (m, 1H, $OCH_2CH=CH_2$), 5.31 (dd, 1H, $J_{trans}$=17.3, $J_{gem}$=1.3 Hz, $OCH_2CH=CH_2$), 5.17 (dd, 1H, $J_{cis}$=10.5 Hz, $OCH_2CH=CH_2$), 4.86 (d, 1H, $J_{1,2}$=3.8 Hz, H-1), 4.27 (dd, 1H, $J_{2,3}$=11.0 Hz, H-2), 4.20 (m, 1H, $OCH_2$), 4.00 (m, 1H, $OCH_2$), 3.89 (dd, $J_{3,4}$=$J_{4,5}$=2.6 Hz, H-4), 3.85-3.77 (m, 2H, H-3 and H-5), 3.72 (m, 2H, H-6a and H-6b) and 1.99 ppm (s, 3H, $CH_3$); $^{13}C$ NMR ($CD_3OD$, 150 MHz): δ 172.5 (NHCO), 134.2 ($OCH_2CH=CH_2$), 116.1 ($OCH_2CH=CH_2$), 96.6 (C-1), 71.2 (C-3), 69.0 (C-4), 68.3. (C-5). 67.8 ($OCH_2$), 61.4 (C-6), 50.2 (C-2) and 21.2 ppm ($CH_3$). FIGS. 7C & 7D: ESI$^+$-HRMS: [M+H]$^+$ calcd for $C_{11}H_{20}O_6N$, 262.1285. found, 262.1294.

Procedure B:

Allyl 2-acetamido-2-deoxy-α-D-galactopyranoside can also be directly prepared from N-acetylgalactosamine (GalNAc) according to literature procedure (Feng et al., 2004: To a solution of N-acetylgalactosamine (442 mg, 2 mmol, 1.0 equiv.) in allyl alcohol (8 mL) at room temperature was added $BF_3.Et_2O$ (250 μL, 2 mmol, 1.0 equiv.), and the mixture was stirred at 70° C. for 2 hours. The solution was cooled to room temperature and the solvent was removed under reduced pressure. The dry crude product was dissolved in minimum EtOH (5 mL). The desire allyl $T_N$ product was precipitated in diisopropyl ether and isolated as white solid (417 mg, 1.60 mmol, 80%).

The C-Allyl GalNAc analog (FIG. 5) [1-(2'-Acetamido-2'-deoxy-α-D-galactopyranosyl)-2-propene] has been prepared according to literature procedure (Cipolla, et al., 2000: 3-(2-Acetamido-3,4,6-tri-O-acetyl-2-deoxy-α-D-galactopyranosyl)-1-propene (Cui et al., 1998) (371 mg, 1.00 mmol, 1.0 equiv.) was treated under Zemplén condition (1M sodium methoxide solution in methanol, 5 mL, pH 8-9). The solution was stirred at room temperature for 1 h. The reaction mixture was neutralized by addition on ion-exchange resin (Amberlite® IR 120, H$^+$), filtered, washed with MeOH, and the solvent was removed under reduced pressure. C-Allyl $T_N$ was purified by chromatography on silica gel (EtOAc/MeOH 9:1 to 4:1) followed by crystallisation in EtOH as white solid (213 mg, 0.87 mmol, 87%). Rf=0.28; EtOH 4:1; mp 230° C. (Litt. 215-217° C., EtOAc/EtOH); According to literature NMR data: $^1H$ NMR ($CD_3OD$, 600 MHz): δ 5.81 (m, 1H, $^1CH_2CH=CH_2$), 5.08 (dd, 1H, $J_{trans}$=17.2, $J_{gem}$=1.7 Hz, $^1CH_2CH=CH_2$), 5.02 (dd, 1H, $J_{cis}$=10.2 Hz, $^1CH_2CH=CH_2$), 4.22 (dd, 1H, J=9.3, 5.0 Hz, H-2'), 4.14 (dt, 1H, J=10.0, 5.0 Hz, H-1'), 3.91 (dd, 1H, J=3.0 Hz, H-4'), 3.82-3.64 (m, 4H, H-3', H-5' and H-6'ab), 2.45 (m, 1H, H-la), 3.17 (m, 1H, H-1b) and 1.97 ppm (s, $CH_3$); $^{13}C$ NMR ($CD_3OD$, 150 MHz): δ 173.6 (NHCO), 136.2 ($^1CH_2CH=CH_2$), 117.1 ($^1CH_2CH=CH_2$), 72.9 (C-1'), 69.7 (C-4'), 69.5 (C-3' and C-5'), 61.8 (C-6'), 52.0 (C-2'), 32.4 ($^1CH_2$) and 22.5 ppm ($CH_3$). ESI$^+$-LCMS: [M+H]$^+$ calcd for $C_{11}H_{20}O_5N$, 246.1336. found, 246.1332. CAN/$H_2O$ 5 to 95% 1.4 min.

The S-Allyl GalNAc analog (FIG. 5) was prepared according to literature: Knapp et al., 2002.

Example 4: Allyl 2-acetamido-4,6-O-benzylidene-2-deoxy-α-D-galactopyranoside (Compound 4)

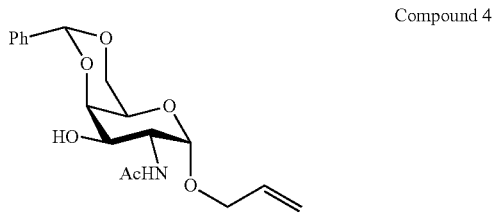

Compound 4

Figure 8A:
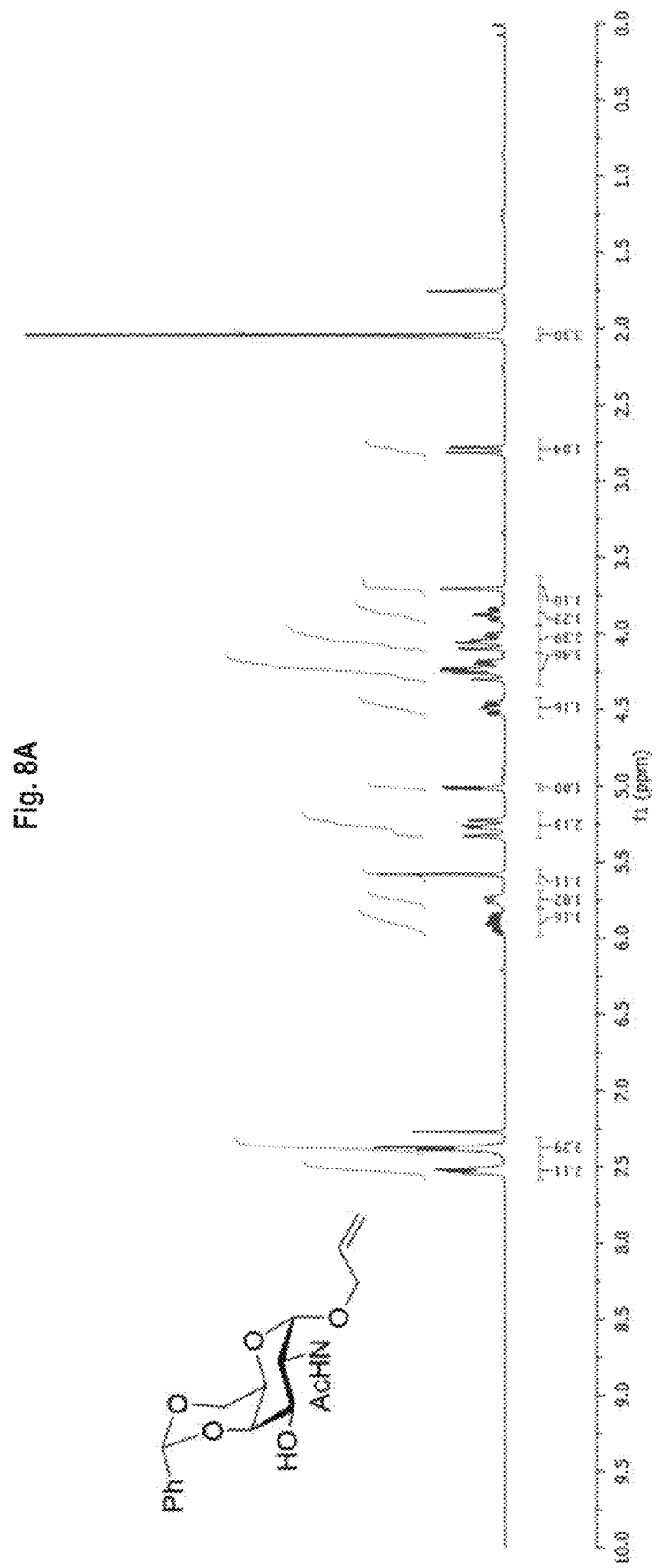
FIG. 8A-8C shows the $^1$H-NMR (FIG. 8A) spectra, as well as mass spectrometry results (FIGS. 8B & 8C) for allyl 2-acetamido-4,6-O-benzylidene-2-deoxy-α-D-galactopyranoside (Compound 4).
Figure 8B:
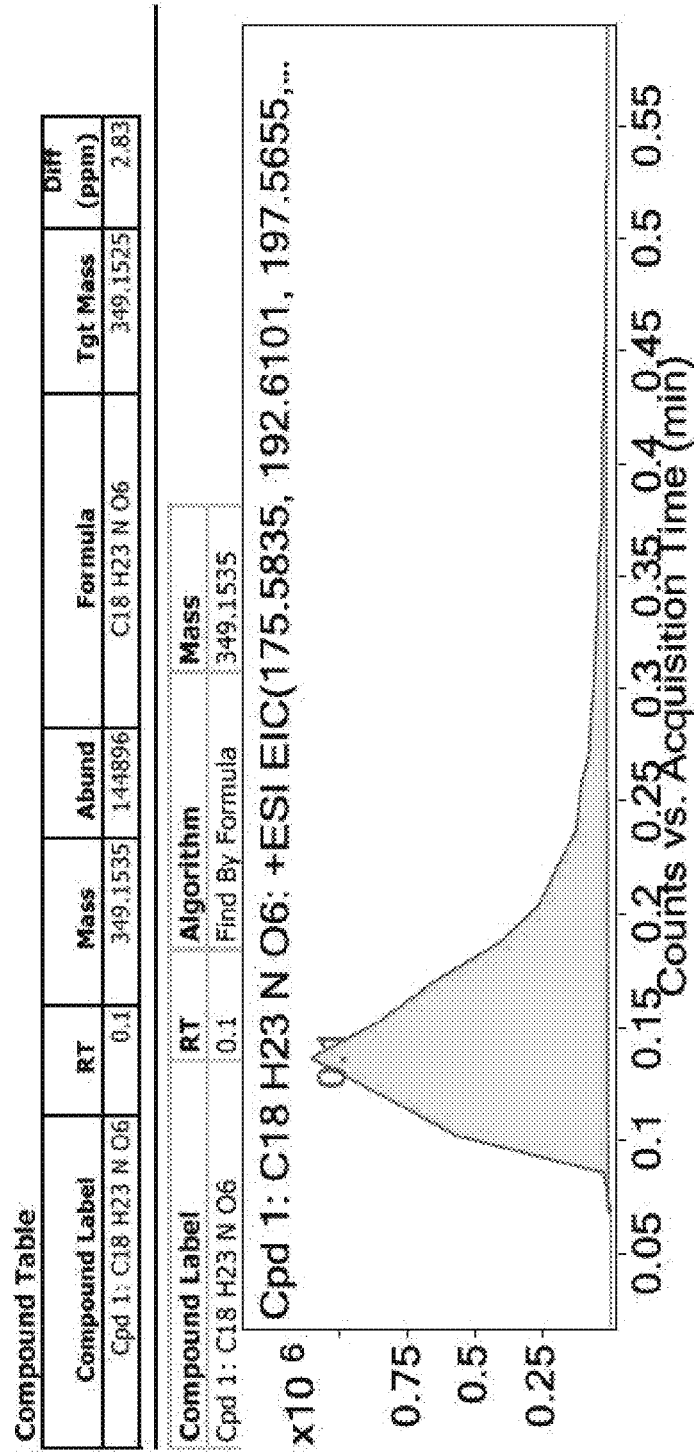
Figure 8C:
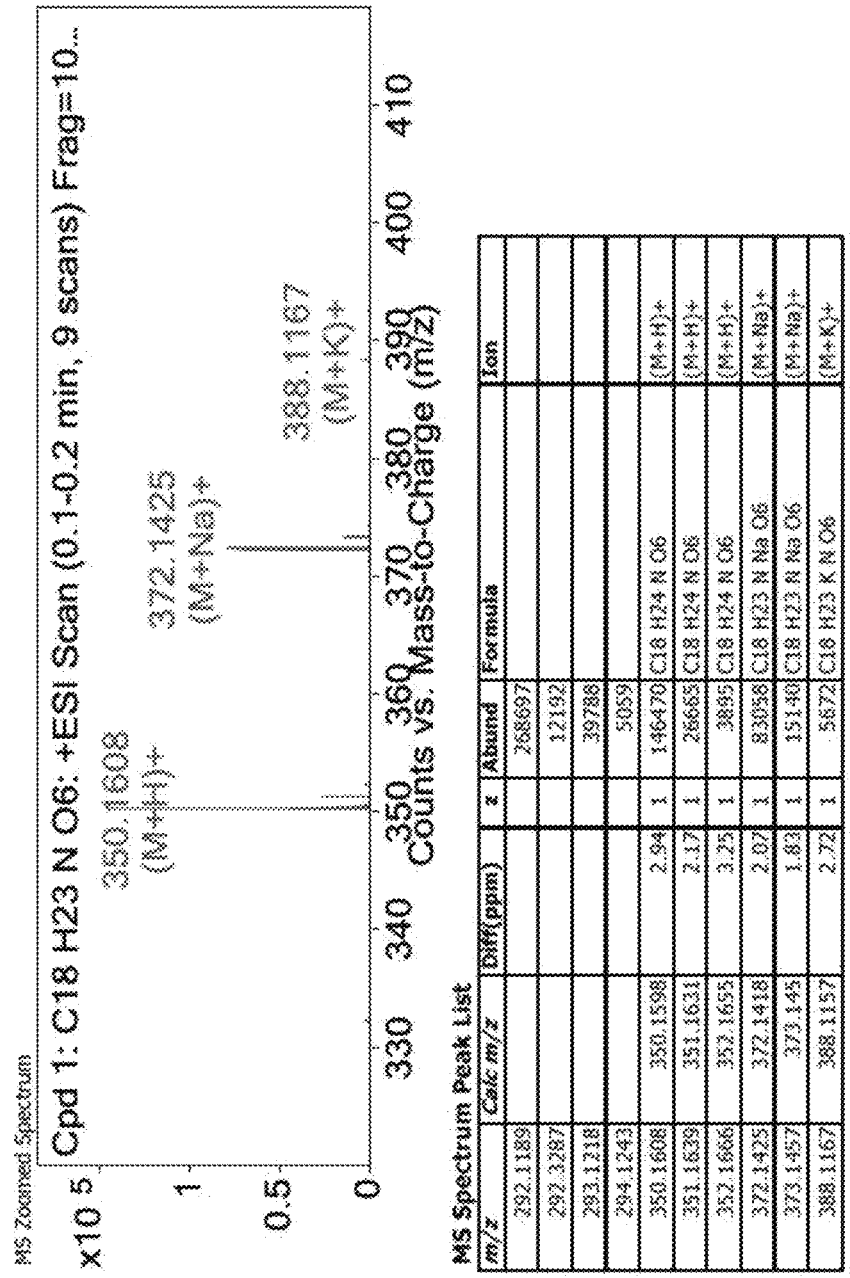

Referring to FIG. 5, to a solution of allyl GalNAc (Tn) (2.35 g, 9.0 mmol, 1.0 equiv.) and benzaldehyde dimethylacetal (6.75 mL, 45.0 mmol, 5.0 equiv.) in dry DMF (20 mL) was added a catalytic amount of p-toluenesulfonic acid monohydrate. The mixture was stirred at room temperature. After 5 hours, the mixture was diluted with $CHCl_3$ and washed with a saturated aqueous solution of $NaHCO_3$. The organic layer was separated and washed with water, dried over $Na_2SO_4$, and concentrated to afford white solid. The benzylidene acetal (4) was isolated by precipitation in EtOAc/Hexanes as white solid (2.64 g, 7.56, 84%). Rf=0.21; DCM/MeOH 9.0:0.5; FIG. 8A: $^1$H NMR ($CDCl_3$, 300 MHz): δ 7.59-7.46 (m, 2H, H-ar), 7.43-7.31 (m, 3H, H-ar), 5.91 (m, 1H, $OCH_2CH=CH_2$), 5.75 (d, 1H, $J_{NH,H2}$=9.0 Hz, NH), 5.58 (s, 1H, PhCH), 5.34-5.17 (m, 2H, $OCH_2CH=CH_2$), 5.01 (d, 1H, $J_{1,2}$=3.5 Hz, H-1), 4.56-4.42 (ddd, 1H, $J_{2,3}$=10.9 Hz, $J_{2,OH}$=9.1 Hz, H-2), 4.34 (dd, 1H, $J_{5,6a}$=1.5 Hz, $J_{6a,6b}$=12.5 Hz, H-6a), 4.19 (m, 2H, H-4 and $OCH_2$), 4.04 (m, 1H, dd, 1H, $J_{5,6b}$=1.6 Hz, $J_{6a,6b}$=12.5 Hz, H-6b), 4.01 (m, $OCH_2$), 3.86 (dd, 1H, $J_{3,4}$=10.9 Hz, H-3), 3.71 (sb, 1H, H-5), 2.80 (d, 1H, $J_{3,OH}$=10.7 Hz, OH-3) and 2.05 ppm (s, 3H, $CH_3$); FIGS. 8B & 8C: ESI$^+$-HRMS: [M+H]$^+$ calcd for $C_{18}H_{24}O_6N$, 350.1598. found, 350.1608.

Example 5: Allyl (2,3,4,6-tetra-O-benzoyl-β-D-galactopyranosyl)-(1→3)-2-acetamido-4,6-O-benzylidene-2-deoxy-α-D-galactopyranoside (Compound 6)

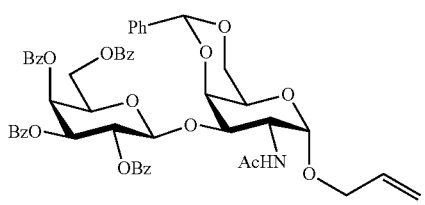

Compound 6

Figure 9A:
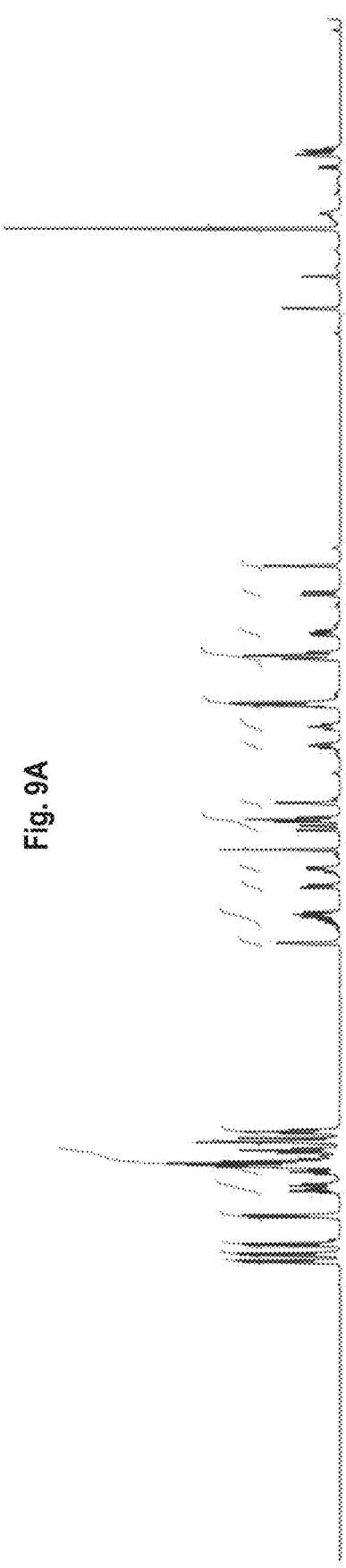
FIG. 9A-9D shows the $^1$H-NMR (FIG. 9A) and $^{13}$C-NMR (FIG. 9B) spectra, as well as mass spectrometry results (FIGS. 9C and 9D) for allyl (2,3,4,6-tetra-O-benzoyl-β-D-galactopyranosyl)-(1→3)-2-acetamido-4,6-O-benzylidene-2-deoxy-α-D-galactopyranoside (Compound 6)
Figure 9B:
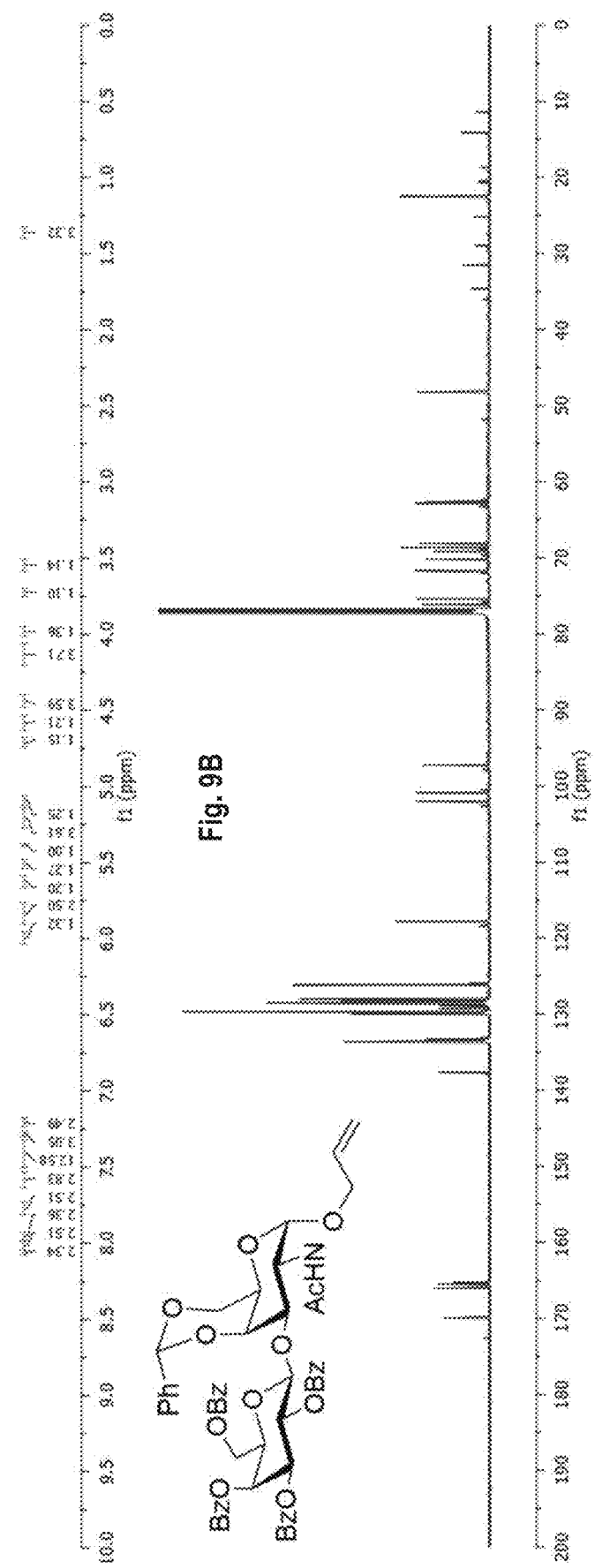
Figure 9C:
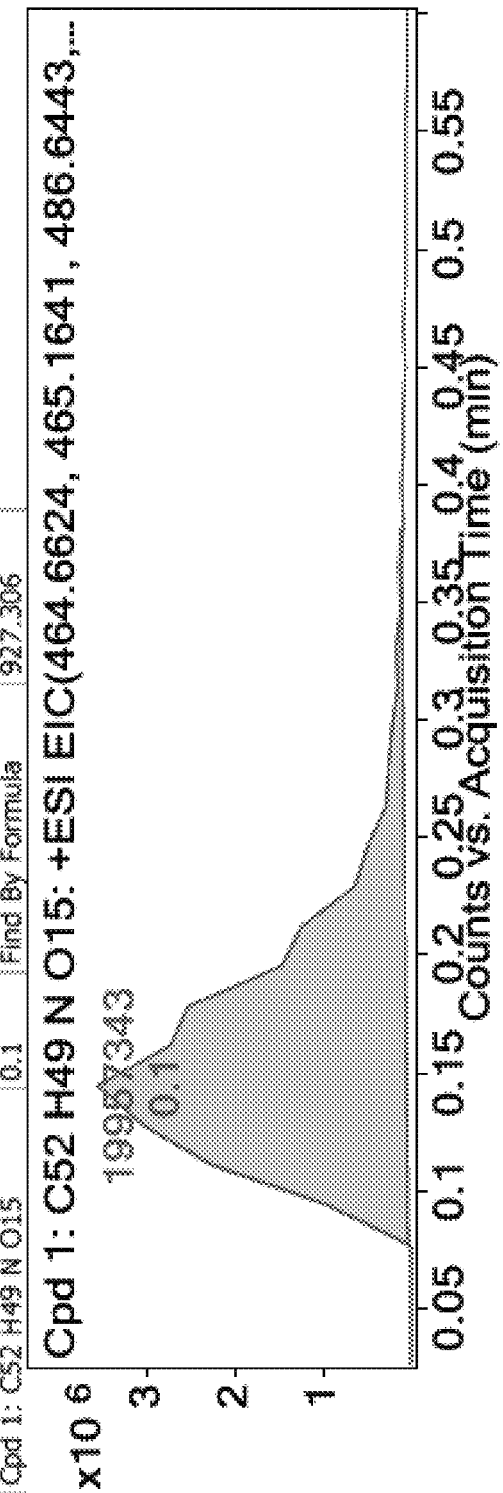
Figure 9D:
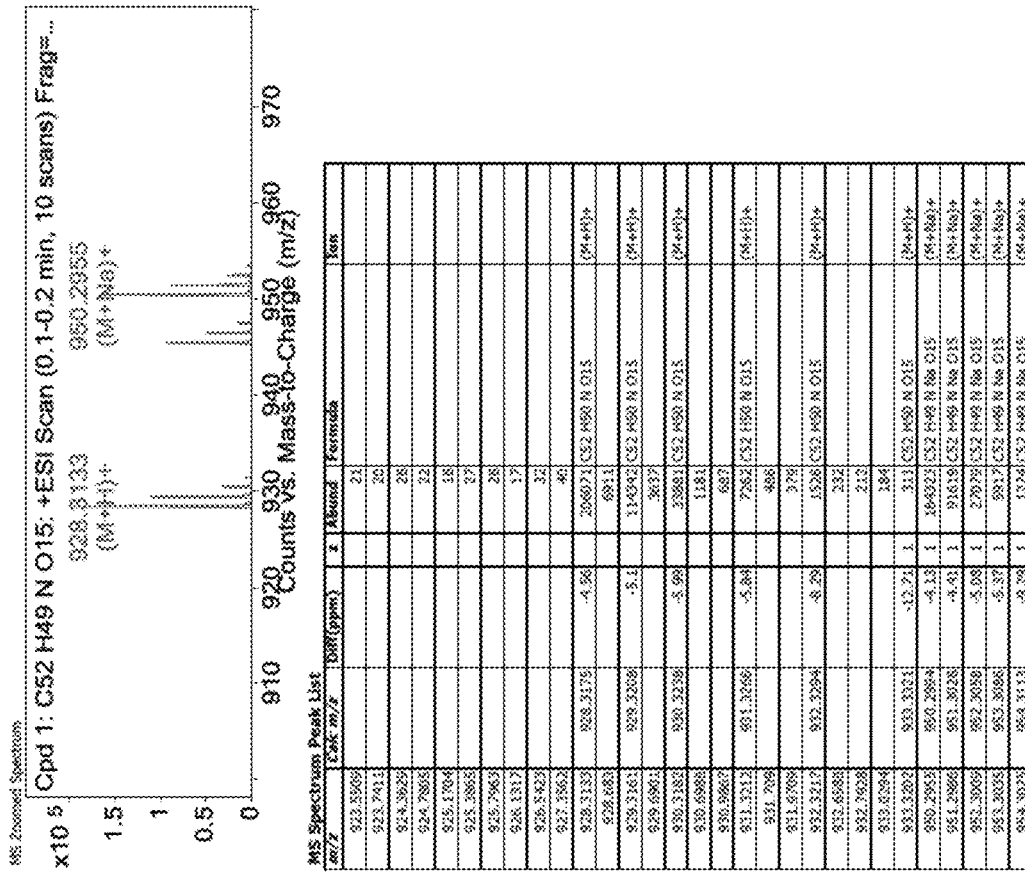

Referring to FIG. 5, Compound 4 (2.0 g, 5.72 mmol, 1.0 equiv.) and mercuric cyanide (2.17 g, 8.60 mmol, 1.5 equiv.) were dissolved in the mixture of anhydrous nitromethane-toluene (100 mL, 3:2, v/v) containing 4 Å molecular sieves under argon atmosphere. The mixture was stirred at room temperature for 30 min. 2,3,4,6-Tetra-O-benzoyl-α-D-galactopyranosyl bromide (Compound 5) (5.66 g, 8.58 mmol, 1.5 equiv.) was added into the mixture. The solution was stirred at 70° C. for five hours, then kept stirring at room temperature overnight (8 hours). After total consumption of the starting material (Compound 4) as indicated by TLC (DCM/MeOH 9.0:0.5), the solvent was removed under reduced pressure. The residue was dissolved in EtOAc followed by filtration through a celite pad. The filtrate was successively washed with 10% aqueous potassium iodide solution, saturated sodium hydrogen carbonate solution and water, then dried over $Na_2SO_4$. The solvent was evaporated under reduced pressure to afford a white foam. The crude product was purified by chromatography on silica gel using a gradient of 100% hexanes to hexanes/EtOAc 1:2 to afford the desired disaccharide (Compound 6) as white solid (4.98, 5.38 mmol, 94%). mp: 110-111° C., Rf=0.20; hexanes/EtOAc 1:2; FIGS. 9A & 9B: $^1$H NMR ($CDCl_3$, 600 MHz): δ 8.06-7.19 (m, 5H, H-ar), 5.98 (dd, 1H, $J_{3,4}$=3.3 Hz, $J_{4,5'}$=1.0 Hz, H-4$^{II}$), 5.85-5.78 (m, 2H, $OCH_2CH=CH_2$ and H-2$^{II}$), 5.60 (dd, 1H, $J_{2,3}$=10.2 Hz, $J_{3,4}$=3.4 Hz, H-3$^{II}$), 5.48 (sb, 1H, NH), 5.23 (m, 3H, $OCH_2CH=CH_2$ and H-1), 4.68 (dd, 1H, $J_{5',6a'}$=6.9 Hz, $J_{6a',6b}$=11.4 Hz, H-6a$^I$), 4.63-4.58 (m, 1H, H-2), 4.46-4.36 (m, 3H, H-4. H-5 and H-6b$^{II}$), 4.14-4.07 (m, 3H, H-6a, $OCH_2$ and H-3), 3.96 (m, 1H, $OCH_2$), 3.75 (m, 1H, H-6b), 3.51 (m, 1H, H-5) and 1.40 ppm (s, 3H, $CH_3$); $^{13}$C NMR ($CDC_{13}$, 150 MHz): δ 170.0 (NHCO), 166.0, 165.5, 165.4, 165.2 (CO), 137.6-126.2 (multi, 30 C-arom), 133.2 ($OCH_2CH=CH_2$), 117.8 ($OCH_2CH=CH_2$), 102.0 (C-1$^{II}$), 100.9 (CPhCH), 97.3 (C-1$^I$), 76.1 (C-3), 75.4 (C-4), 71.7 (C-3$^{II}$ and C-5$^{II}$), 70.2 (C-2$^{II}$), 69.1 (C-6), 68.6 ($OCH_2$), 68.1 (C-4$^{II}$), 62.9 (C-5), 62.6 (C-6$^I$), 48.2 (C-2) and 22.5 ppm ($CH_3$). FIGS. 9C & 9D: ESI$^+$-HRMS: [M+H]$^+$ calcd for $C_{52}H_{50}O_{15}N$, 928.3175; found, 928.3133.

Example 6: Allyl (β-D-galactopyranosyl)-(1→3)-2-acetamido-2-deoxy-α-D-galactopyranoside (Allyl TF)

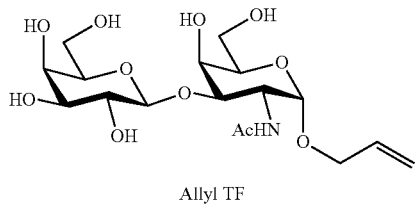

Allyl TF

Figure 10A:
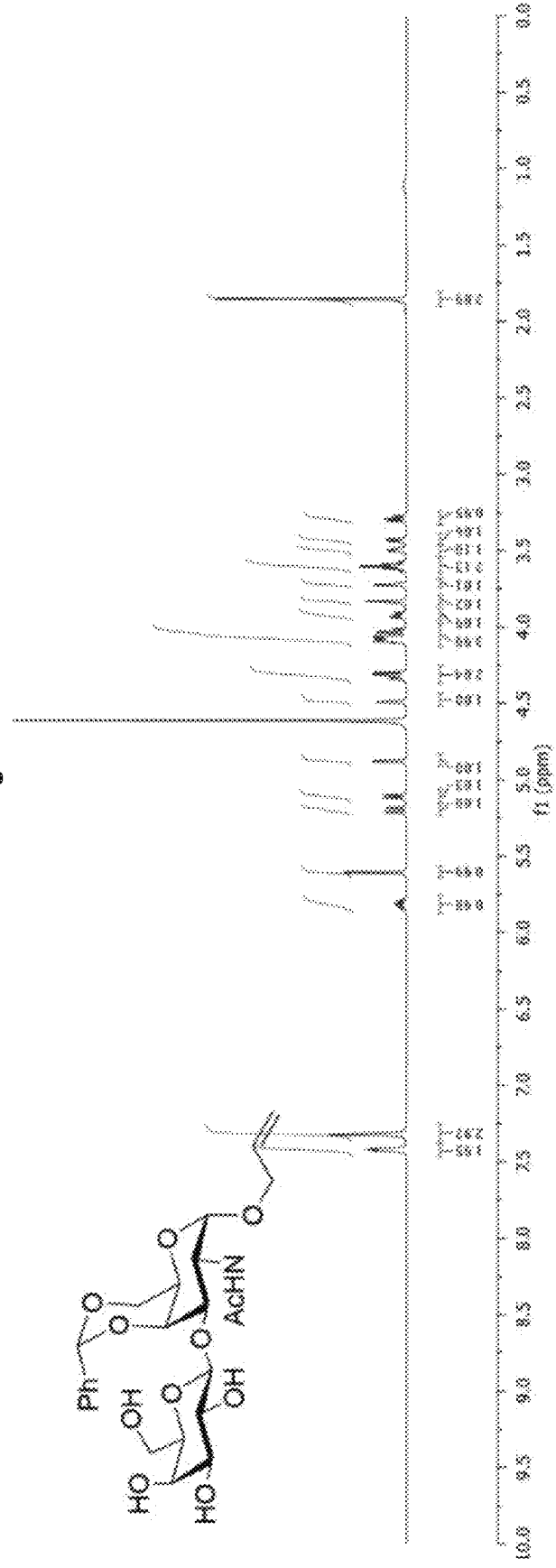
FIG. 10A-10D shows the $^1$H-NMR (FIG. 10A) and $^{13}$C-NMR (FIG. 10B) spectra, as well as mass spectrometry results (FIGS. 10C and 10D) for Compound 7.
Figure 10B:
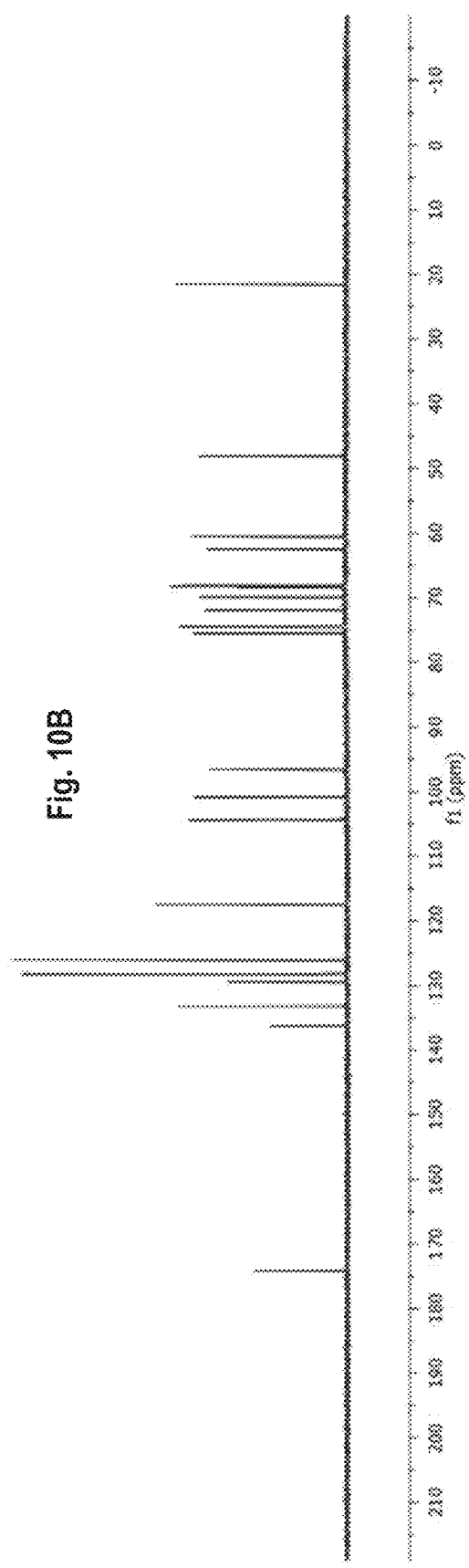
Figure 10C:
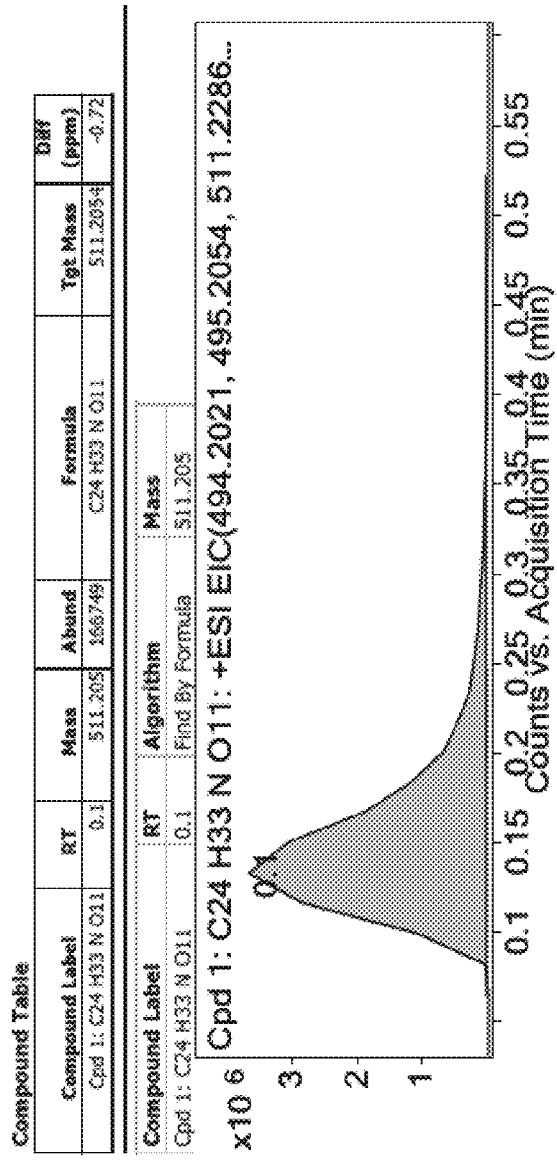
Figure 10D:
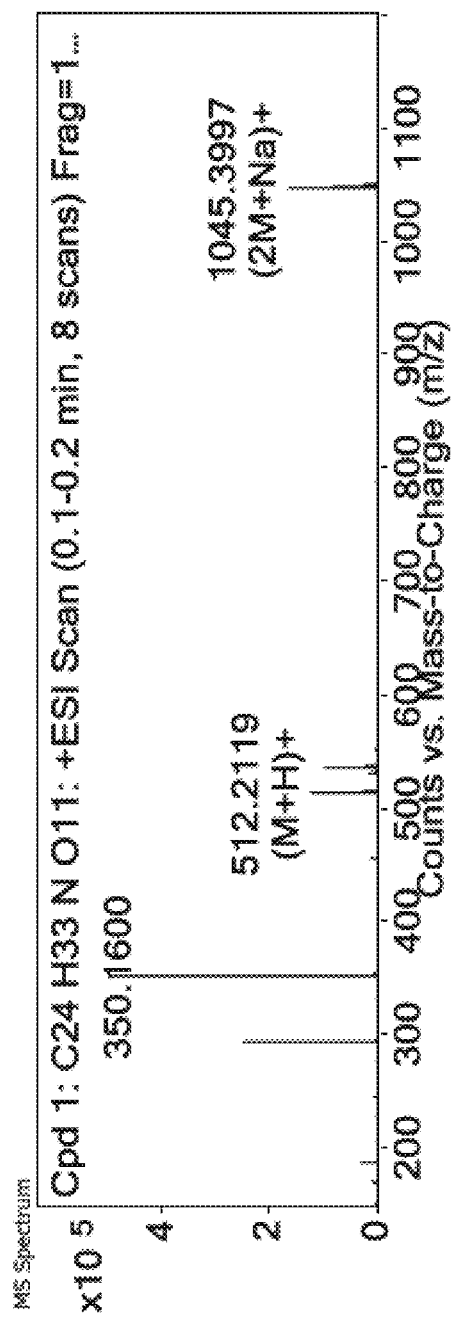

Referring to FIG. 5, a solution of compound 6 (1.12 g, 1.20 mmol, 1.0 equiv.) in 1M sodium methoxide in methanol (12 mL, pH 8-9) was stirred at room temperature until consumption of starting material. After 1 h 30 min, the solution was neutralized by the addition of ion-exchange resin (Amberlite IR 120, H$^+$), filtered, washed with MeOH, and the solution was suspended with silica gel, filtered, and the solvent removed under reduced pressure. The silica gel was washed with 100% EtOAc several times followed by washing with second solution (EtOAc/MeOH/$H_2O$ 1:1:0.1). The combined filtrate was evaporated under reduced pressure to afford the intermediate (Compound 7) as white solid. Rf=0.20; $CHCl_3$/MeOH/$H_2O$ 11:6:1; FIGS. 10A & 10B: $^1$H NMR ($D_2O$, 600 MHz): δ 7.47-7.39 (m, 2H, H-ar), 7.37-7.26 (m, 3H, H-ar), 5.82 (m, 1H, $OCH_2CH=CH_2$), 5.61 (s, 1H, PhCH), 5.20-5.09 (m, 2H, $OCH_2CH=CH_2$), 4.88 (d, 1H, $J_{1,2}$=3.4 Hz, H-1), 4.47 (dd, H-4), 4.37-4.25 (m, 2H, H-2 and H-$1^{II}$), 4.13-3.98 (m, 4H, H-3, H-6a, H-6b, $OCH_2$), 3.96-3.88 (m, 1H, H-5), 4.56-4.42 (ddd, 1H, $J_{2,3}$=10.9 Hz, $J_{2,OH}$=9.1 Hz, H-2), 4.34 (dd, 1H, $J_{5,6a}$=1.5 Hz, $J_{6a,6b}$=12.5 Hz, H-6a), 4.19 (m, 2H, H-4 and $OCH_2$), 4.04 (m, 1H, dd, 1H, $J_{5,6b}$=1.6 Hz, $J_{6a,6b}$=12.5 Hz, H-6b), 4.01 (m, $OCH_2$), 3.86 (dd, 1H, $J_{3,4}$=10.9 Hz, H-3), 3.71 (sb, 1H, H-5), 2.80 (d, 1H, $J_{3,OH}$=10.7 Hz, OH-3) and 2.05 ppm (s, 3H, $CH_3$); 3.83 (s, 1H, $OCH_2$), 3.72 (d, 1H, $J_{3',4'}$=$J_{4',5'}$=3.2 Hz, H-$4^{II}$), 3.65-3.55 (m, 2H, H-6a,b), 3.49, (m, 1H, H-$5^{II}$), 3.43 (dd, 1H, $J_{2',3'}$=10.0 Hz, $J_{3',4'}$=3.3 Hz, H-$3^{II}$), 3.33-3.24 (m, 1H, H-$2^{II}$) and 1.86 ppm (s, 3H, $CH_3$); $^{13}C$ NMR ($D_2O$, 150 MHz): δ 174.6 (NHCO), 136.8 (C-arom), 133.6 ($OCH_2CH{=}CH_2$), 129.9, 128.7, 126.5 (C-arom), 118.0 ($OCH_2CH{=}CH_2$), 104.9 (C-$1^{II}$), 101.3 (CHPh), 97.0 (C-1), 76.0 (C-4), 75.0 (C-3), 75.0 (C-$5^{II}$), 72.4 (C-$3^{II}$), 70.4 (C-$2^{II}$), 69.0 (C-6), 68.7 ($OCH_2CH{=}CH_2$), 68.6 (C-$4^{II}$), 63.0 (C-5), 61.0 (C-$6^{II}$), 48.6 (C-2) and 22.0 ppm ($CH_3$). Rf=0.38; EtOAc/MeOH/$H_2O$ 7:3:0.1; Rf=0.46; ACN/MeOH/$H_2O$ 7:2:1. FIGS. 10C & 10D: ESI$^+$-HRMS: $[M+H]^+$ calcd for $C_{24}H_{34}O_{11}N$, 512.2126. found, 512.2119.

Figure 11C:
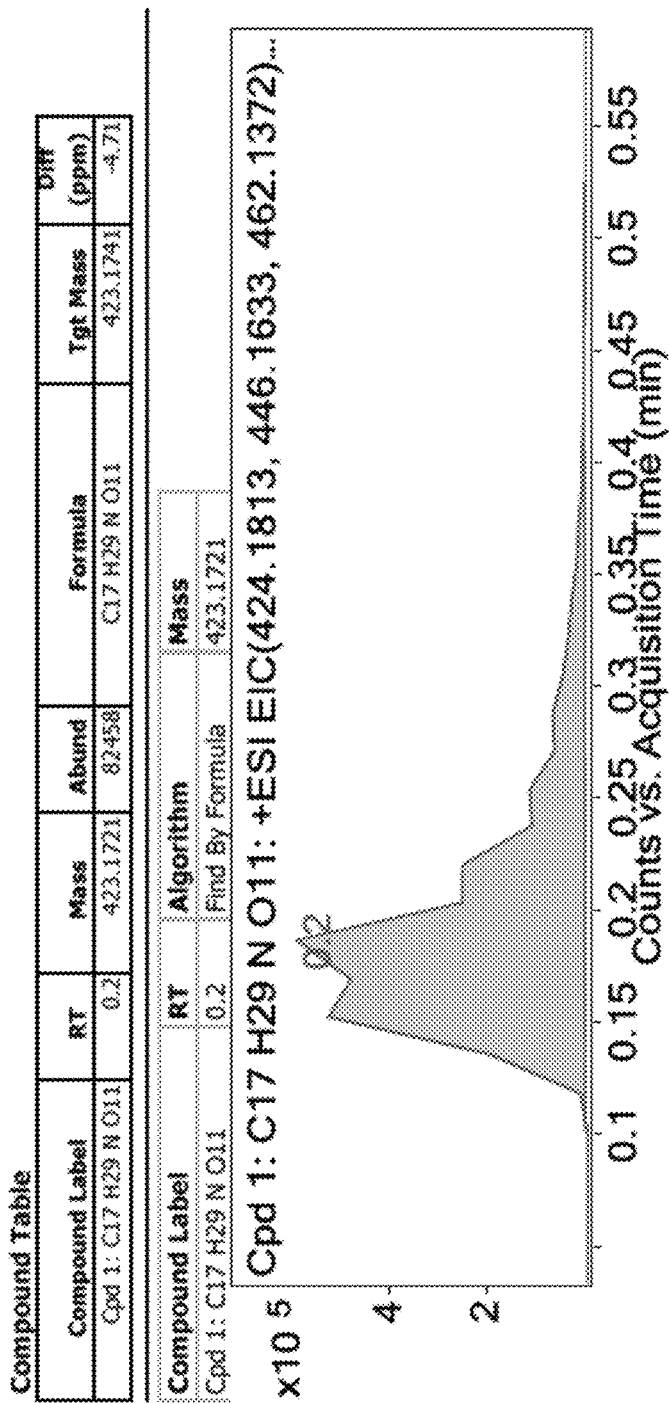
Figure 11D:
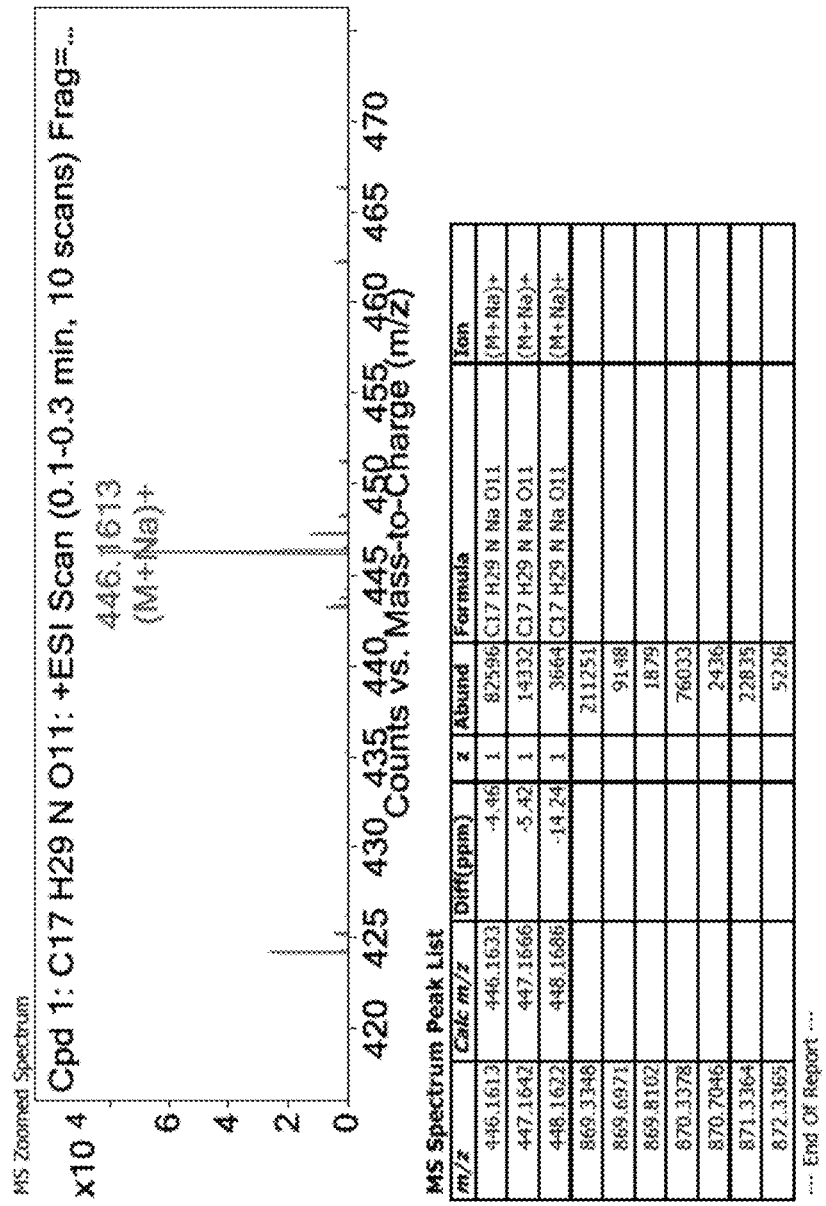

The white solid intermediate was then dissolved in 10 mL of 60% aqueous acetic acid and the resulting solution was stirred at 60° C. for 1.5 hours. The solvent was removed under reduced pressure, and the residue was lyophilized to afford the final allyl TF as white solid (427 mg, 1.0 mmol, 84%). mp=230-232° C.; Rf=0.53; $CHCl_3$/MeOH/$H_2O$ 11:6:1; FIGS. 11A & 11B: $^1H$ NMR ($D_2O$, 600 MHz): δ 5.80 (m, 1H, $OCH_2CH{=}CH_2$), 5.19 (dd, 1H, $J_{trans}$=17.3 Hz, $OCH_2CH{=}CH_2$), 5.09 (dd, 1H, $J_{cis}$=10.4 Hz, $OCH_2CH{=}CH_2$), 4.77 (d, 1H, $J_{1,2}$=3.7 Hz, H-1), 4.29 (d, 1H, $J_{1,2}$=3.7 Hz, H-1), 4.29 (d, 1H, $J_{1,2}$=7.8 Hz, H-$1^{II}$), 4.16 (dd, 1H, $J_{2,3}$=11.2 Hz, $J_{1,2}$=3.7 Hz, H-2), 4.08-4.01 (m, 2H, H-4 and $OCH_2$), 3.92-3.82 (m, 3H, H-3, H-5 and $OCH_2$), 3.73 (dd, 1H, H-$4^{II}$), 3.63-3.52 (m, 4H, H-6a,b and H-6'a,b), 3.47 (m, 2H, H-$3^{II}$ and H-$5^{II}$), 3.39 (dd, 1H, $J_{2',3'}$=10.0 Hz, $J_{1',2'}$=7.7 Hz, H-$2^{II}$) and 1.85 ppm (s, 3H, $CH_3$); $^{13}C$ NMR (150 MHz, $CDCl_3$): δ 174.6 (NHCO), 133.7 ($OCH_2CH{=}CH_2$), 117.9 ($OCH_2CH{=}CH_2$), 104.7 (C-$1^{II}$), 96.4 (C-1), 77.2 (C-3), 75.0 (C-$5^{II}$), 72.5 (C-$3^{II}$), 70.7 (C-5), 70.6 (C-$2^{II}$), 68.8 (C-4), 68.6 (C-$4^{II}$), 68.4 ($OCH_2$), 61.2 (C-$6^{II}$), 61.0 (C-6), 48.6 (C-2) and 22.0 ppm ($CH_3$). FIGS. 11C & 11D: ESI$^+$-HRMS: $[M+Na]^+$ calcd for $C_{17}H_{29}O_{11}NNa$, 446.1633. found, 446.1613.

Figure 12:
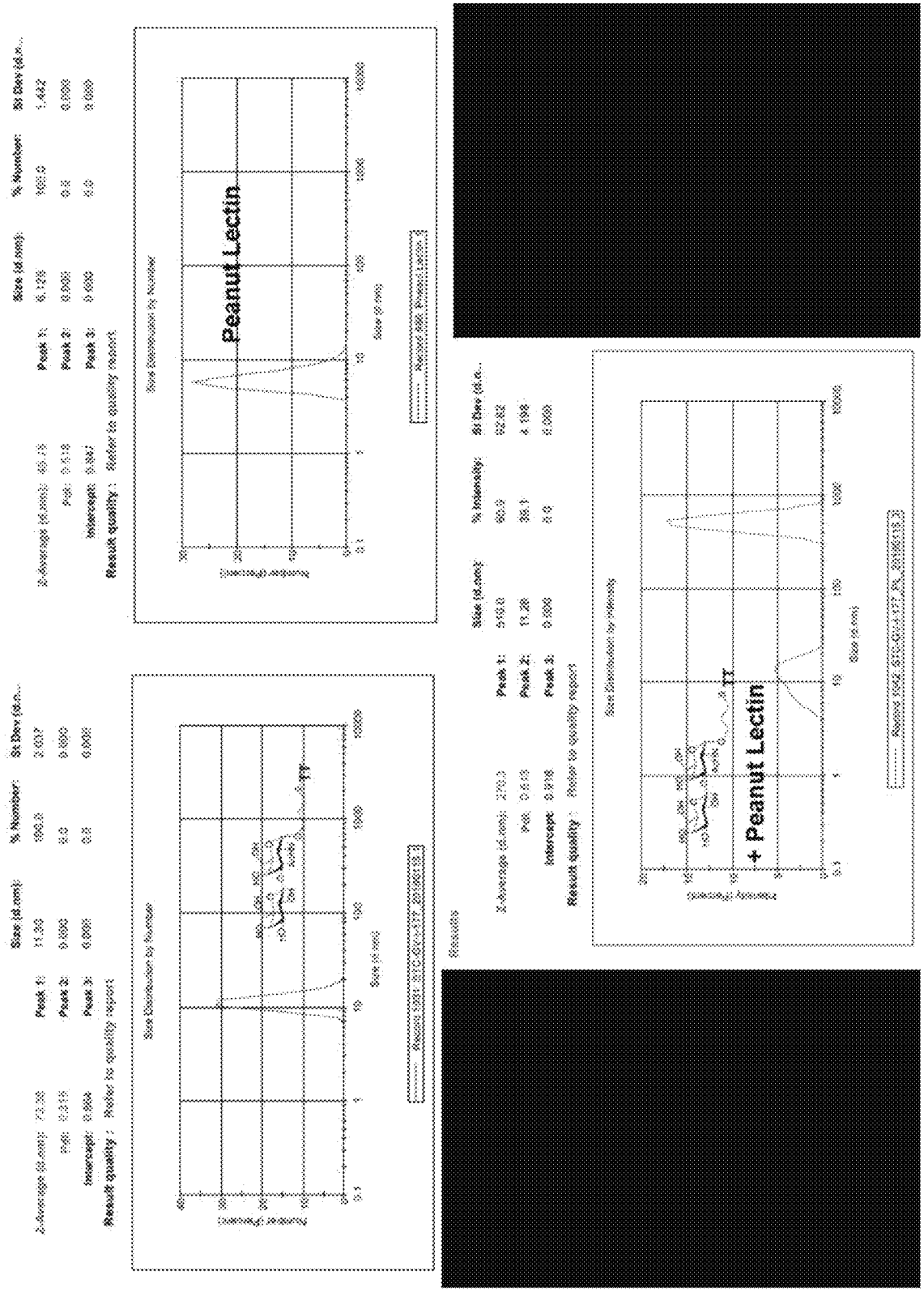
FIG. 12 shows the results of Dynamic Light Scattering (DLS) analyses of the TF-TT glycoconjugate alone (upper left panel), peanut lectin alone (upper right panel), or both combined (lower panel).

Example 7: Purification of Tetanus Toxoid Monomer

Tetanus toxoid (TT) monomer was obtained by gel filtration chromatography before conjugation. One milliliter of a liquid preparation containing 4.5 mg/ml protein (as determined by the modified Lowry protein assay) was loaded onto a XK16-100 column filled with Superdex®200 Prep Grade (GE Healthcare Life Sciences, Uppsala, Sweden) equilibrated in PBS (20 mM $NaHPO_4$ [pH 7.2], 150 mM NaCl) and eluted with the same buffer. The protein eluted from the column in two peaks: the earlier-eluting peak contained oligomerized toxoid, and the later-eluting peak, corresponding to a Mr of 150,000, contained TT monomer. Fractions corresponding to the later (monomer) peak were pooled, desalted against deionized water, concentrated using a Centricon® Plus-70 centrifugal filter device (30K Ultracel PL membrane; Millipore, Billerica, Mass.), and then lyophilized.

Example 8: Tn-Tetanus Toxoid Conjugate (Tn-TT Conjugate)

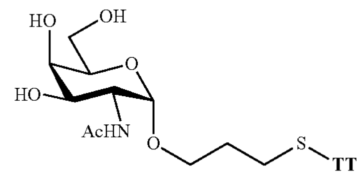

Tn-TT conjugate

Procedure A:

To a solution of allyl Tn (0.15 mg, 0.56 μmol, 18.0 equiv.) in 500 μL PBS was added 1.5 mL of PBS containing 4.7 mg (0.03 μmol) of tetanus toxoid in a quartz cell. The solution was irradiated at 254 nm for 7 hours after degazing under argon atmosphere. The solution was dialyzed for 24 hours against several washes of doubly distilled water, and lyophilized to give the Tn-TT-A conjugate as white solid (2.0 mg, 43%). Procedure B: Under the same thiol-ene click reaction, a catalytic amount of DMPA in acetonitrile (100 μL) was added into the solution of allyl Tn (3 mg, 10.8 μmol, 180.0 equiv.) containing Tetanus toxoid in PBS (2 mL, 4.5 mg/mL, 0.06 μmol). The solution was irradiated at 365 nm for 15 min. The solution was then dialyzed for 24 hours, and lyophilized to give Tn-TT-B conjugate as white solid (5.4 mg, 61%).

Example 9: TF-Tetanus Toxoid Conjugate (TF-TT Conjugate)

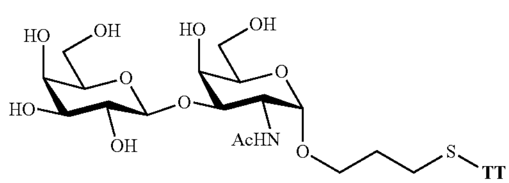

TF-TT conjugate

Procedure A:

To a solution of allyl TF (0.24 mg, 0.56 μmol, 18.0 equiv.) in 500 μL PBS was added 1.5 mL of PBS containing 4.7 mg (0.03 μmol) of tetanus toxoid in a quartz cell. The solution was irradiated at 254 nm for 7 hours after degazing under argon atmosphere. The solution was then dialyzed for 24 hours, and lyophilized to give TF-TT-A conjugate as white solid (2.1 mg, 45%). Procedure B: Under the same thiol-ene click reaction, a catalytic amount of DMPA in acetonitrile (100 μL) was added into the solution of allyl TF (5 mg, 10.8 μmol, 180.0 equiv.) with Tetanus toxoid in PBS (2 mL, 4.5 mg/mL, 0.06 μmol). The solution was irradiated at 365 nm for 15 min. The solution was then dialyzed for 24 hours, and lyophilized to give TF-TT-B conjugate as white solid (5.3 mg, 60%).

Example 10: Characterization of Tn-TT and TF-TT Conjugates

The tetanus toxoid (TT) alone and the vaccine conjugates (Tn-TT-A; Tn-TT-B; TF-TT-A; and TF-TT-B) were analyzed by SDS gel electrophoresis, colorimetric analyses for the presence of sugar content (Dubois test), thiol content by the Ellmann test, Dynamic Light Scattering (DLS) (FIG. 12), and reactivity with the known mouse monoclonal antibody JAA-F11 using double radial immunodiffusion. The SDS gel electrophoresis results clearly indicated the monomeric form of the conjugate that also stained positive for the presence of the carbohydrate antigens (Tn and TF). The colorimetric analyses (Dubois test) confirmed the presence of the carbohydrate antigens (10% by weight) and that there were no residual free thiol groups on the carrier protein following conjugation. The double radial immunodiffusion analyses revealed a precipitation band, clearly indicating the cross-reactivity of the new TF-TT conjugate with the anti-TF monoclonal antibody JAA-F11, thus confirming the presence of the immunogenic carbohydrate antigen (TF) on the TF-TT conjugate and that no precipitation band was observed with the carrier protein (tetanus toxoid) alone.

HPLC Analysis of the Conjugates.

HPLC analysis of the glycoconjugate preparations was done by size exclusion chromatography. The chromatographic separation was performed with three 8-by 300-mm Shodex OHpak gel filtration columns connected in series (two SB-804 and one SB-803) preceded by a SB-807G guard column (Showa Denko). The glycoconjugate immunogens were eluted with 0.1 M NaNO$_3$ at a flow rate of 0.4 mL/min using a Knauer Smartline system equipped with a differential refractometer (RI) detector model 2300 and a UV detector model 2600 at wavelength of 280 nm. The conjugate preparation (8-mg/mL solution in the mobile phase) was injected using a 504µA injection loop. In selected experiments, the fractions eluting at the void volume, which correspond to the conjugate fractions, were pooled, dialyzed against water Spectra/Por; Molecular weight cut-off (MWCO), 12,000 to 14,000 [Spectrum Laboratories]), and lyophilized. This corresponds to the 2:1 fractionated conjugate.

Figure 13:
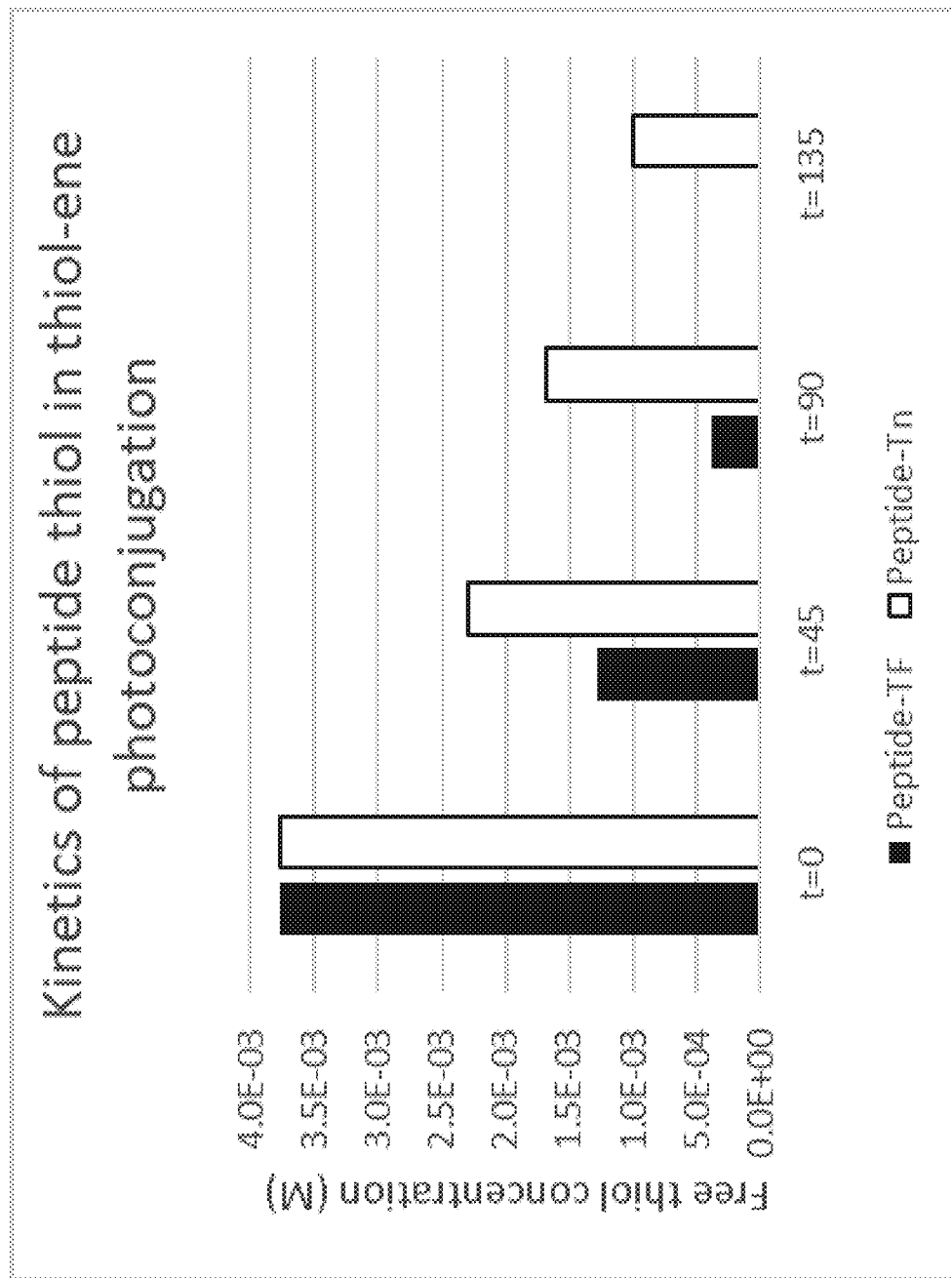
FIG. 13 shows the thiol concentration of the peptide dTT831-840 as a function of time in the photocatalytic thiol-ene conjugation reaction with O-Allyl-Tn and O-Allyl-TF.

Example 11: Effect of the Conjugation of O-Allyl-Sugars by the Thiol-Ene Photoreaction on the Free Thiol of Peptide dTT831-844-Cys-βAla The peptide dTT831-844-Cys-βAla (Tetanus Toxin (831-844); MW: 1813, SEQ ID NO: 2) was solubilized in water at a concentration of 3.7e-3 M and (500 uL) of peptide was stirred at room temperature with (6 uL, 0.1M, 3.0 equiv.) O-Allyl-Tn or O-Allyl-TF and water-soluble catalyst AAPH (2,2'-Azobis(2-methylpropionitrile, 23 uL, 0.025M, 3.0 equiv. in a quartz cuvette (10×10 mm path length, Fisher) placed between two hand held UV365 nm lamp (0.16 amps, VWR) at a distance of 2-5 cm from the cuvette. The UV was turned on immediately following the addition of AAPH. The solution was sampled at 0, 45, 90 and 135 minutes and free thiol concentration was measured by the Ellman test using a cysteine standard curve. FIG. 13 shows that the free thiol concentration is reduced in a time dependent manner as a result of the photo thiol-ene reaction.

Example 12: Effect of Cysteine Positioning/Accessibility in dTT831-844-Cys-βAla, and the Type of Activator Employed, on Conjugation of O-Allyl-Tn and Immunoreactivity of the Thiol-Ene Photoreaction Product The peptide dTT831-844 was synthesized with an N-terminal or C-terminal cysteine and solubilized in water at a concentration of 2 mM (1 mL) that was stirred at room temperature with 200 uL, 0.1 M, 10 equiv.) of O-Allyl-Tn and a catalytic amount (0.2 equiv.) of activator AAPH in a quartz cuvette (10×10 mm path length, Fisher) placed between two hand held UV365 nm lamp (0.16 amps, VWR) at a distance of 2-5 cm from the cuvette. The UV was turned on immediately following the addition of activator and allowed to react for 60 min. The free thiol concentration was measured by the Ellman test using a cysteine standard curve at time 0 and 60 min. The fold reduction in free thiol correspond to the thiol concentration at t=0/t=60.

Figure 14:
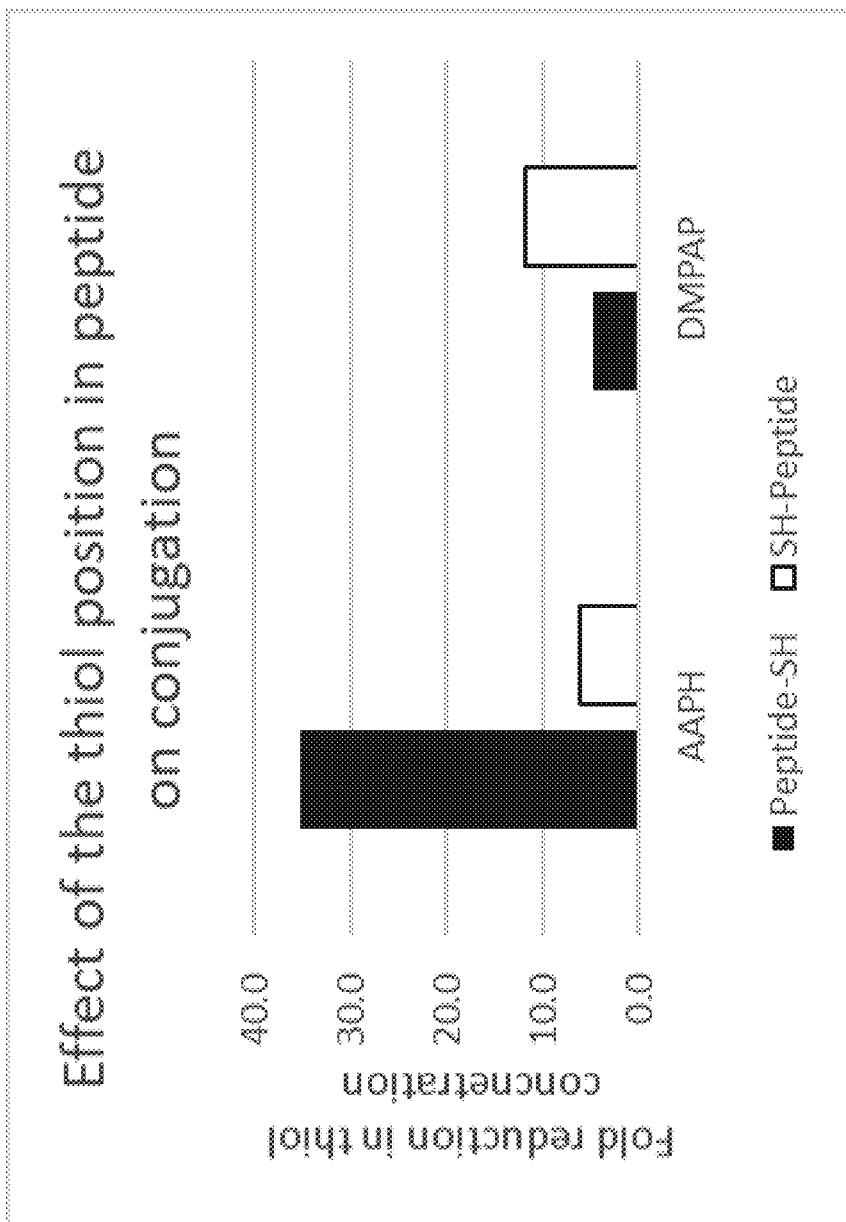
FIG. 14 shows the fold reduction of thiols of the peptide dTT831-840 in the photocatalytic thiol-ene conjugation reaction with O-Allyl-Tn as a function of the peptide's cysteine position and the presence of AAPH or DMPA.

The results are shown in FIG. 14, which presents the fold reduction in free thiol concentration for dTT831-844 peptides having an N-terminal ("SH-peptide") or C-terminal ("Peptide-SH") cysteine, and using either a water-soluble (AAPH) or water-insoluble activator (DMPA), in the thiol-ene photoreaction conjugation.

The immunoreactivity of the thiol-ene photoreaction product was measured by an Enzyme-linked lectin assay (ELLA). 1 µg of peptide in 100 µL PBS pH 7.4 was allowed to adsorb to 96-well plates (Maxisorp™, Nunc) for a minimum of 1 h at RT or overnight at 4° C. The wells were then washed twice with PBS-Tween™ 0.05% (PBS-T) and then filled with PBS-T+1% BSA blocking solution for 30 minutes. The wells were then washed 3 times with PBS-T and filled with 100 µL of a 1/100 dilution of the lectin *Vicia Villosa* (anti-Tn VVA) or Peanut agglutinin (anti-TF PNA) coupled to the horseradish peroxidase (VVA-hrp, PNA-hrp, EY LAbs). After an incubation of 1 h at RT with gentle shaking or 12 h at 4° C., the wells were washed 4 times with PBS-T and 100 µL of hrp substrate was added (Ultra TMB-ELISA, Thermo Scientific) to each well. The reaction was stopped by the addition of 100 µL of 0.5N sulfuric acid and the plate was read in a plate reader at OD 450 nm (Biotek EL808).

Figure 15:
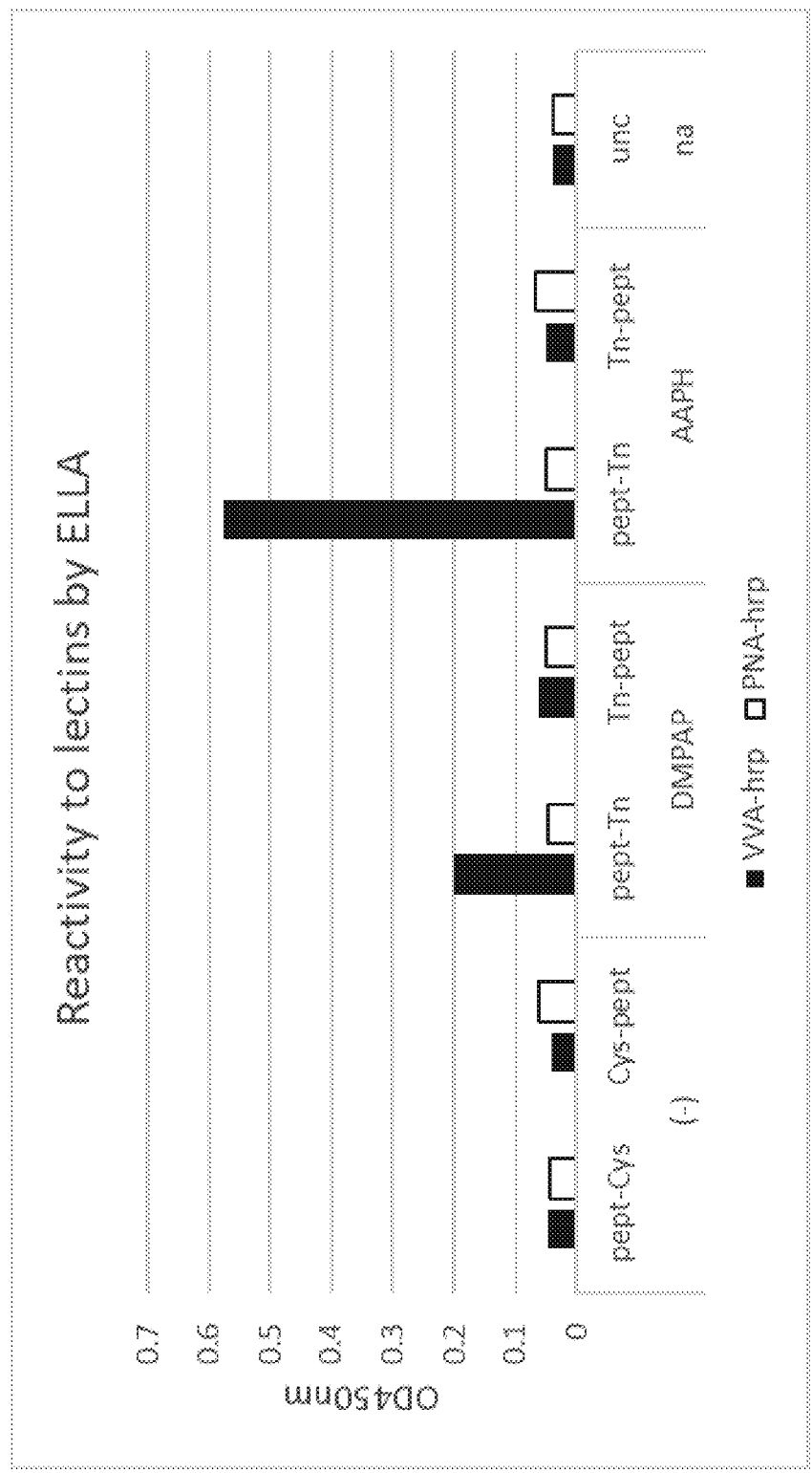
FIG. 15 shows the reactivity of lectins to peptide dTT831-840 conjugated to Tn by the photocatalytic thiol-ene conjugation reaction with O-Allyl-Tn as a function of the position of the peptide's cysteine and the presence of AAPH or DMPA.

The results are shown in FIG. 15, which presents lectin reactivity to the different Tn-peptides (i.e., unconjugated: "pep-Cys" and "Cys-pep"; Tn-conjugated: "Tn-pep" and "pep-Tn"; "unc": uncoated plate) using either a water-soluble (AAPH) or water-insoluble activator (DMPA). Interestingly, TT peptides with a C-terminal cysteine were specifically recognized by the anti-Tn lectin VVA, and the conjugation reaction was most effective with the water-soluble activator AAPH. None of the Tn glycoconjugates were recognized by the anti-TF lectin (peanut lectin, PNA) used as a negative control.

Figure 16:
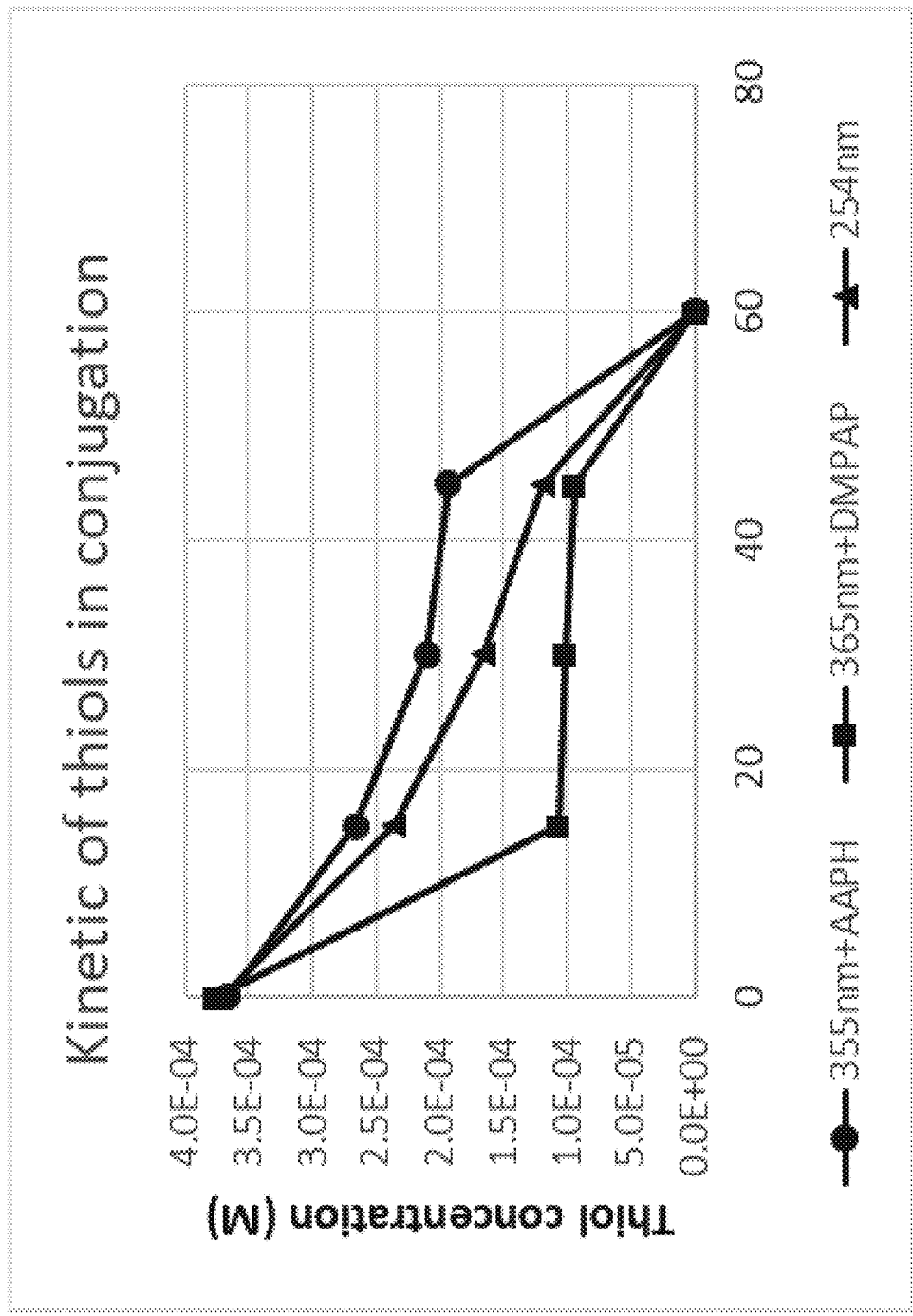
FIG. 16 shows the kinetics of thiol concentration of the peptide dTT831-840 in the photocatalytic thiol-ene conjugation reaction with O-Allyl-Tn at different wave lengths in the presence of AAPH or DMPA.

Example 13: Effect of Wavelength on Thiol-Ene Photoreaction Conjugation of Peptide dTT831-844-Cys-βAla to O-Allyl-Tn The peptide dTT831-844-Cys-βAla (MW: 1813, SEQ ID NO: 2) was stirred at room temperature with O-Allyl-Tn 0.55 mM in 1 mL water and AAPH (1.44 mg, 5.5 nmol, 10.0 equiv.) or (0.3 mg, 1.1 nmol, 2.0 equiv.) DMPA in a quartz cuvette (10×10 mm path length, Fisher) placed between two hand held UV lamps at either 365 nm or 355 nm (0.16 amps, VWR) at a distance of 2-5 cm from the cuvette. The UV was turned on immediately following the addition of AAPH and turned off to stop the reaction after (60 min). The peptide was also conjugated to O-Allyl-Tn in the absence of activator and at UV254 nm. The free thiol concentration was measured by the Ellman test using a cysteine standard curve. FIG. 16 shows the decrease in free thiol over time (minutes) for three different conjugation conditions ("355 nm+AAPH"; "365 nm+DMPA"; and "254 nm").

The immunoreactivity of the thiol-ene photoreaction product was measured by Enzyme-linked lectin assay (ELLA). The indicated quantity of peptide in 100 µL PBS pH 7.4 was allowed to adsorb to 96-well plates (Maxisorp, Nunc) for a minimum of 1 h at RT or overnight at 4° C. The wells were then washed twice with PBS-Tween™ 0.05% (PBS-T) and the wells filled with blocking solution for 30 minutes. The wells were then washed 3 times with PBS-T and filled with 100 μL of a 1/100 dilution of the lectin *Vicia Villosa* coupled to the horseradish peroxidase (VVA-hrp, EY LAbs). After an incubation of 1 h at RT with gentle shaking or 12 h at 4° C., the wells were washed 4 times with PBS-T and 100 μL of hrp substrate was added (Ultra TMB-ELISA, Thermo Scientific) to each well. The reaction was stopped by the addition of 100 μL of 0.5N sulfuric acid and the plate was read in a plate reader at 450 nm (Biotek EL808).

Figure 17:
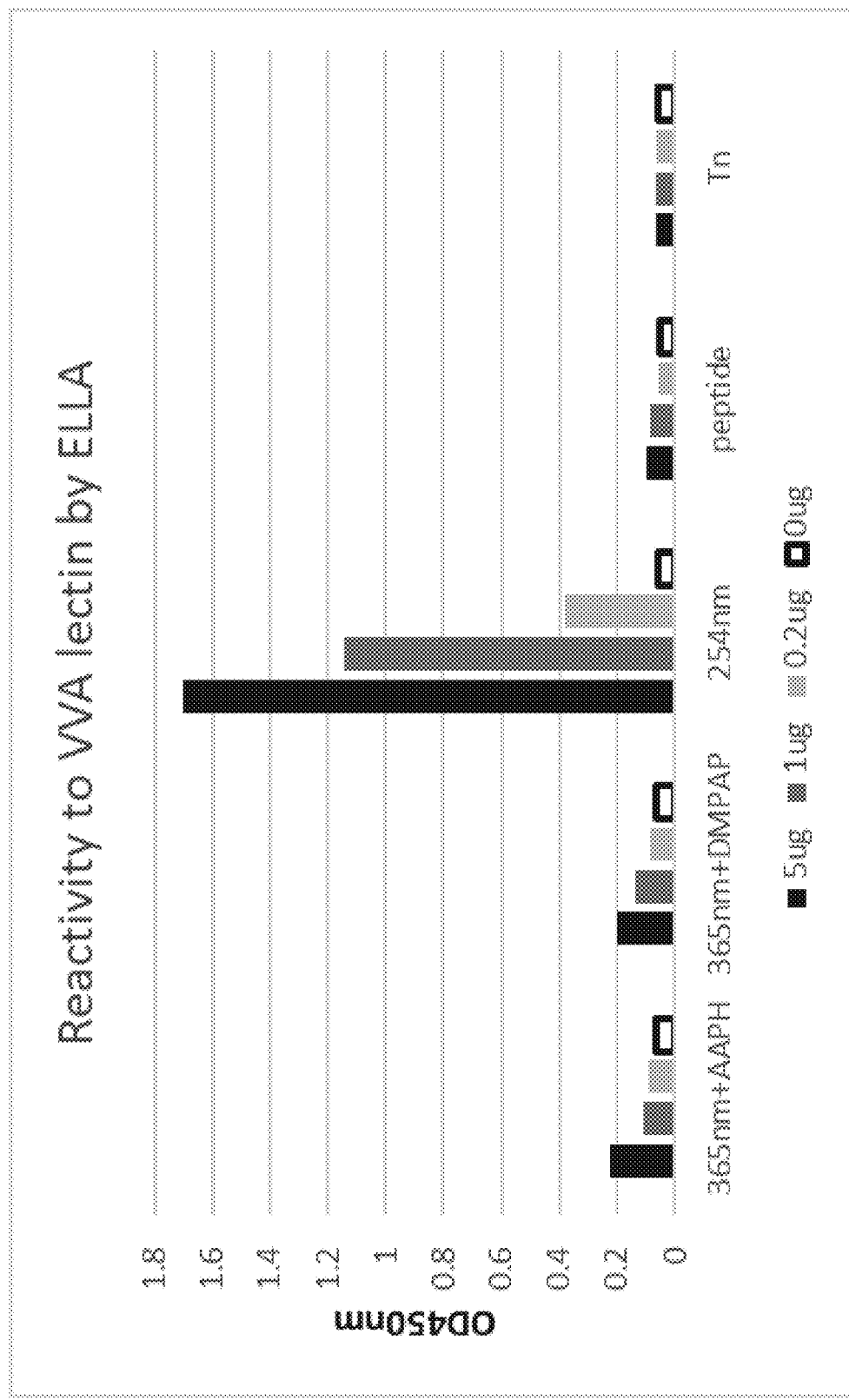
FIG. 17 shows the reactivity of the lectin *Vicia Villosa* to the peptide dTT831-840 conjugated to Tn by the photocatalytic thiol-ene conjugation reaction with O-Allyl-Tn at different wave lengths in the presence of AAPH or DMPA.

The ELLA results are presented in FIG. 17, which shows VVA lectin reactivity to various quantities of Tn-peptides conjugated by thiol-ene photoreaction at 365 nm in the presence of AAPH or DMPAP, or at 254 nm in absence of activator. The conjugation products were detected by the lectin, while the unconjugated peptide ("peptide") or O-Allyl-Tn alone ("Tn") were unreactive. Interestingly, FIG. 17 shows that conjugation at 254 nm in the absence of activator generated a glycoconjugate product that was more immunoreactive than the ones generated by 365 nm or 355 nm in the presence of activator.

Figure 18:
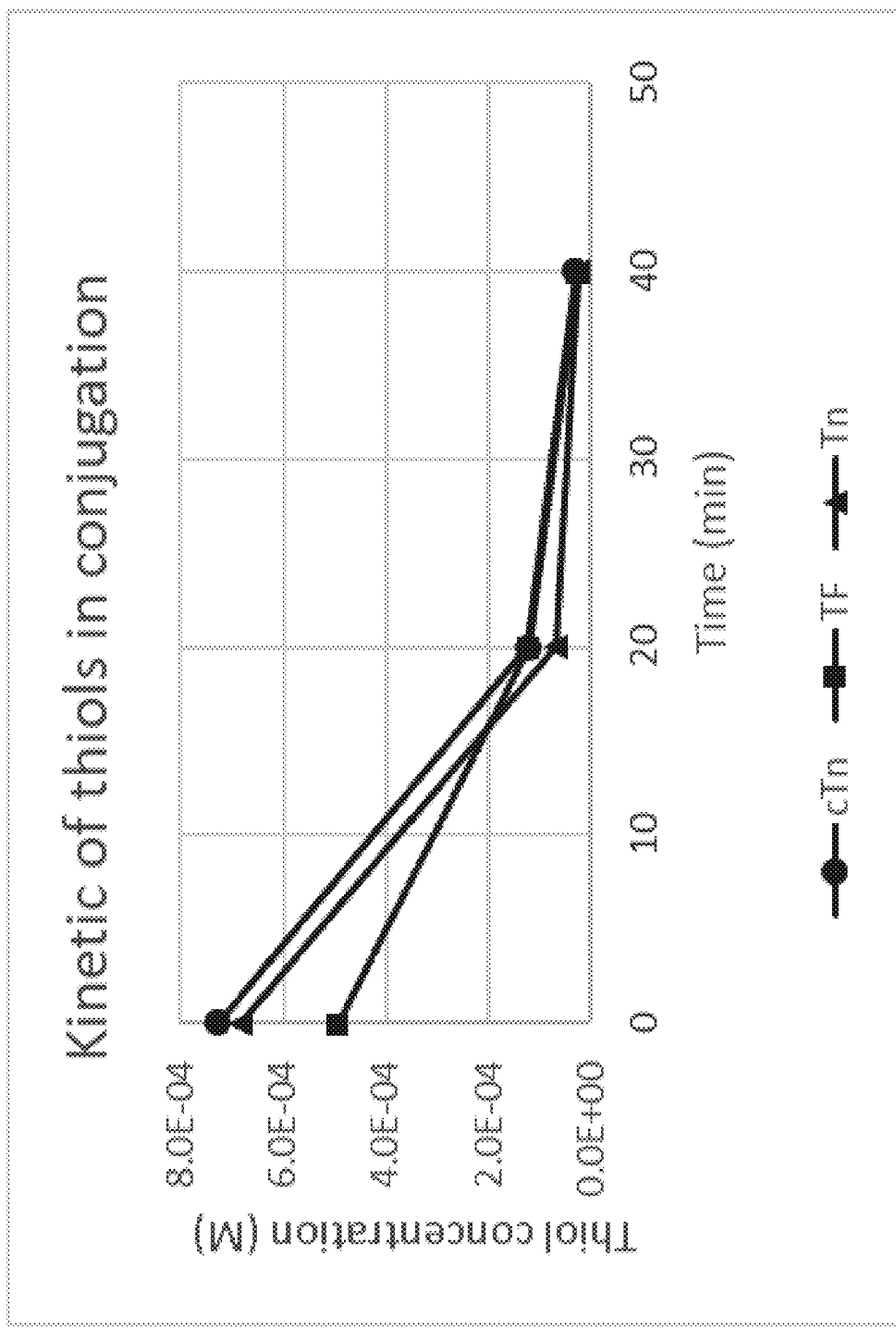
FIG. 18 shows the kinetics of thiol concentration of the peptide dTT831-840 in the photocatalytic thiol-ene conjugation reaction with C-Allyl and O-Allyl sugars.

Example 14: Conjugation and Reactivity of C-Allyl and O-Allyl Saccharides to Peptide dTT831-844-Cys-βAla by the Thiol-Ene Photoreaction The dTT831-844-Cys-βAla peptide (MW: 1813) was solubilized in water at a concentration of 0.55 mM and 1 mL of it was stirred at room temperature with O-Allyl-Tn, O-Allyl-TF, or C-Allyl-Tn (100 uL, 11 mM, 2.0 equiv) and AAPH (1.44 mg, 5.5 nmol, 10.0 equiv.) in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH. The solution was sampled at the indicated time and free thiol concentration was measured by the Ellman test using a cysteine standard curve. FIG. 18 shows the decrease in free thiol over time (minutes) for the different allyl saccharides tested: O-Allyl-Tn ("Tn"), O-Allyl-TF ("TF"), or C-Allyl-Tn ("cTn").

The immunoreactivity of the thiol-ene photoreaction product was measured by enzyme-linked lectin assay and enzyme-linked immunosorbent assay. The indicated quantity of peptide conjugate in 100 μL PBS pH 7.4 was allowed to adsorb to 96-well plates (Maxisorp, Nunc) for a minimum of 1 h at RT or overnight at 4° C. The wells were then washed twice with PBS-Tween™ 0.05% (PBS-T) and then filled with PBS-T+1% BSA blocking solution for 30 minutes. The wells were then washed 3 times with PBS-T and filled with 100 μL of a 1/100 dilution of the lectin *Vicia Villosa*, or Peanut agglutinin coupled to the horseradish peroxidase (VVA-hrp, PNA-hrp, EY LAbs), or 0.1 μg/ml of TF-specific purified murine monoclonal antibody JAAF11. After an incubation of 1 h at RT with gentle shaking or 12 h at 4° C., the wells containing JAAF11 were washed with PBS-T then further incubated for 60 minutes with secondary antibody goat anti-mouse IgG (H+L)-hrp (Jackson Immunoresearch). Wells were then washed 4 times with PBS-T and 100 μL of hrp substrate was added (Ultra TMB-ELISA, Thermo Scientific) to each well. The reaction was stopped by the addition of 100 μL of 0.5N sulfuric acid and the plate was read in a plate reader at 450 nm (Biotek EL808).

Figure 19:
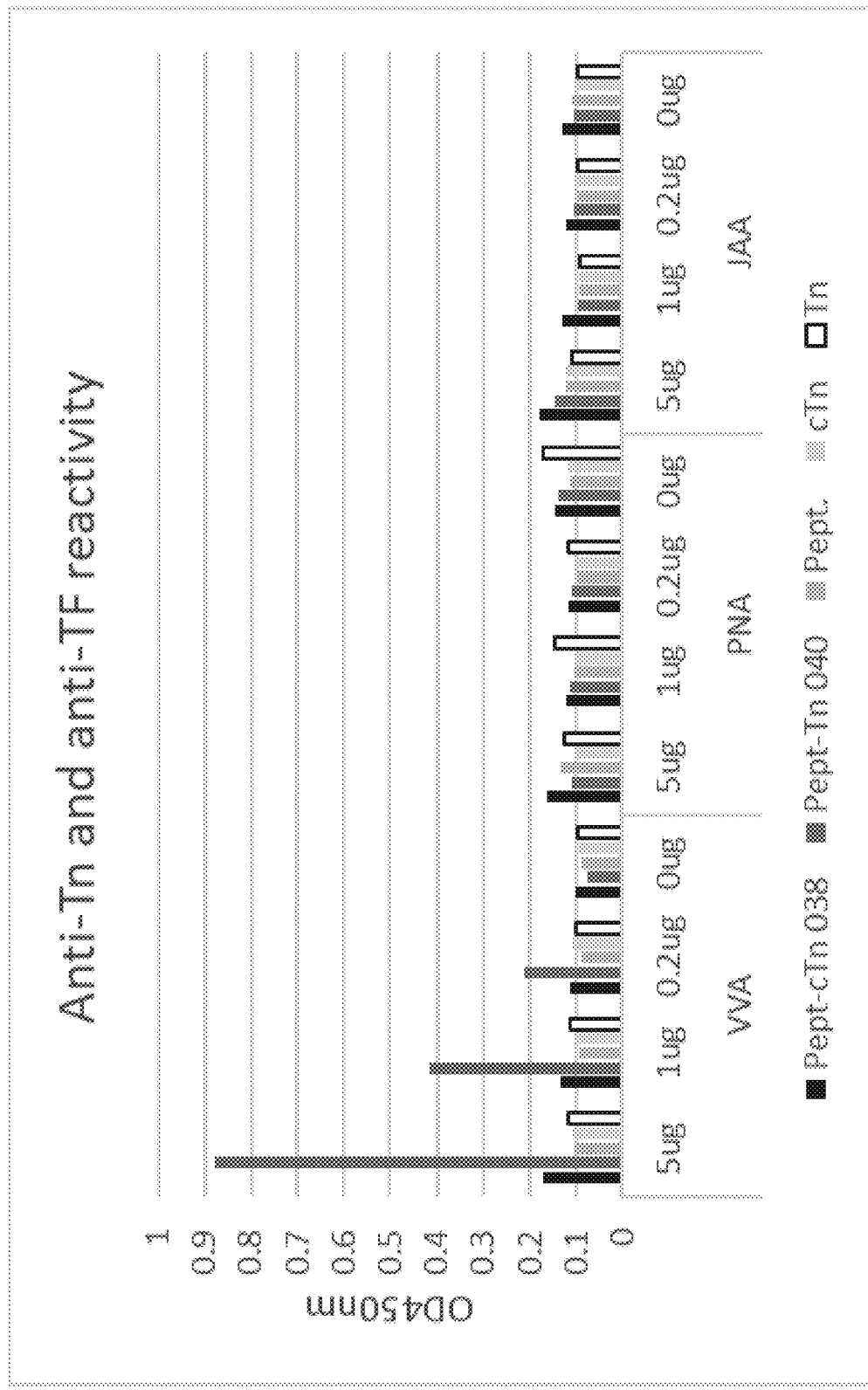
FIG. 19 shows the reactivity of lectins and anti-TF antibody to peptide dTT831-840 conjugated by the photocatalytic thiol-ene conjugation reaction with O-Allyl-Tn.

FIG. 19 shows that only the peptide conjugate generated with the O-Allyl-Tn (but not with the C-Allyl-Tn) was recognized by the anti-Tn lectin VVA. These results suggest that, while being conjugated to the peptide, the C-Allyl-Tn does not have a conformation that allows binding to the lectin.

Example 15: Conjugation of O-Allyl-TF to Chemically Reduced dTT by Thiol-Ene Photoreaction Detoxified tetanus toxoid (dTT) was dialysed in PBS pH 7.4 (MWCO 2,000) then incubated with 1000 eq DTT. After a 2 hours incubation at RT and rotation, the reduced protein solution was washed in PBS pH 7.4 by centrifugal filtration (MWCO 10,000, Amicon). The reduced protein (1 mL, 3.51 mg/mL, 0.02 nmol) was then stirred with O-Allyl-TF (30.0 equiv.) and AAPH (2.0 equiv.) in a final volume of 1.0 mL PBS in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction then stopped after 2 h.

The free thiol concentration of the reduced dTT generated by the DTT treatment compared to native dTT was measured on buffer exchanged dTT sample by an Ellman test using a cysteine standard curve and the protein concentration was measured by a Bradford assay using a BSA standard curve.

To measure the immunoreactivity of the dTT samples, 1 μg of protein sample was diluted into 100 μL of PBS pH 7.4 and allowed to adsorb to the well of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 μL of 0.1 μg/mL of TF-specific purified murine monoclonal antibody JAAF11. After an incubation of 1 h at RT with gentle shaking or 12 h at 4° C., the plate was washed with PBS-T then further incubated for 60 minutes with 100 μL of 1/1000 dilution of the secondary antibody goat anti-mouse IgG (H+L)-hrp (Jackson Immunoresearch). Wells were then washed 4 times with PBS-T and 100 μL of hrp substrate was added (Ultra TMB-ELISA, Thermo Scientific) to each well. The reaction was stopped by the addition of 100 μL of 0.5N sulfuric acid and the plate was read in a plate reader at 450 nm (Biotek EL808).

Figure 20:
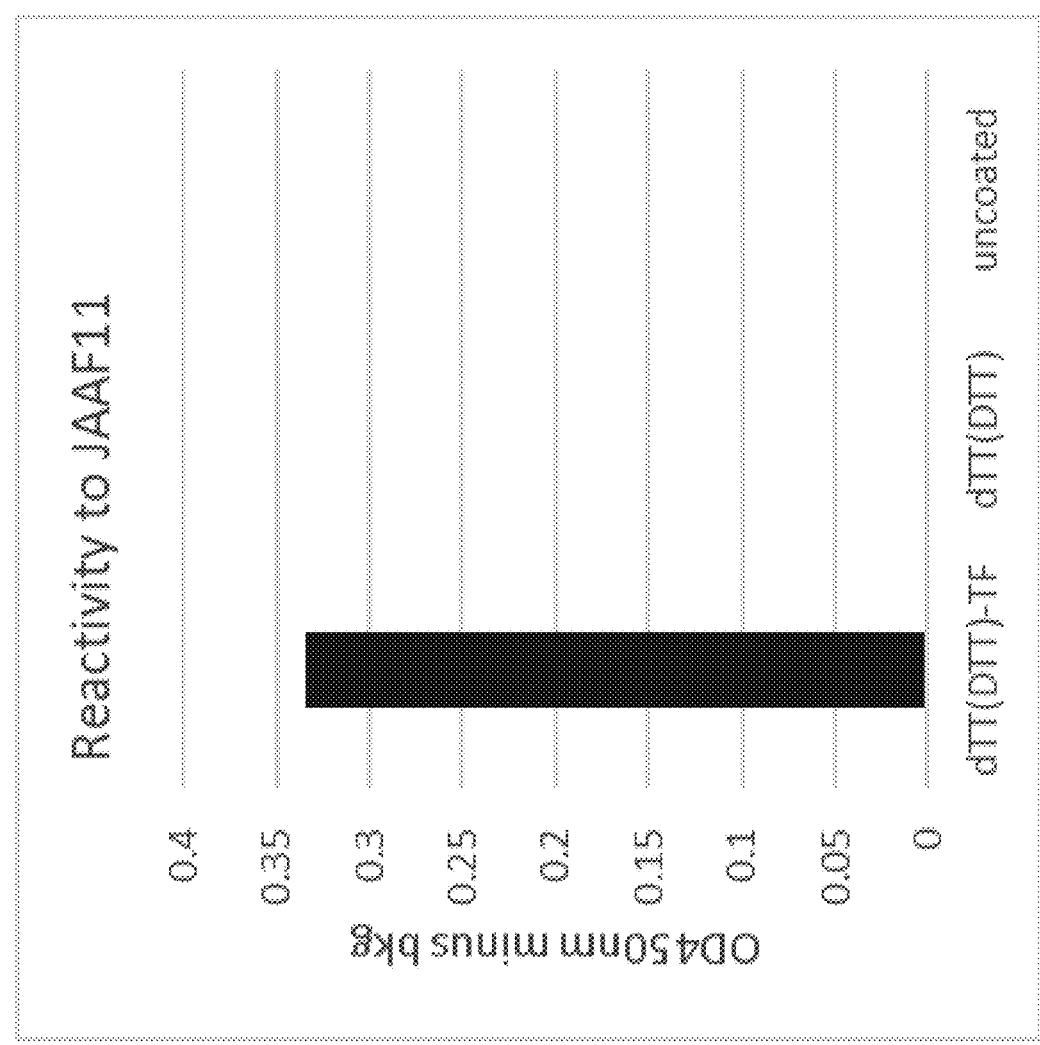
FIG. 20 shows the reactivity of anti-TF antibody to reduced dTT or reduced dTT conjugated by the photocatalytic thiol-ene conjugation reaction with O-Allyl-TF.

FIG. 20 shows the immunoreactivity dTT-TF to JAAF11 ("dTT(DTT)-TF"), while the reduced dTT ("dTT(DTT)") or native dTT (data not shown) were unreactive. This indicates that the O-Allyl-TF was indeed conjugated to dTT by the thiol-ene photo reaction in an immunoreactive conformation.

Example 16: Conjugation of O-Allyl-Tn to Chemically Reduced dTT by Thiol-Ene Photoreaction dTT was dialysed in PBS pH 7.4 (MWCO 30,000) then 0.5 mL (5.8 mg/mL) was incubated with 50 or 500 eq DTT at RT under rotation. After 2 h, the reduced protein solution was washed in PBS pH 7.4 by centrifugal filtration (MWCO 10,000, Amicon). The protein reduced with 500 eq of DTT (70 uL, 0.5 mmol/mL) was then stirred with 0.1M O-Allyl-TF (60.0 equiv.) and 0.1M AAPH (4.0 equiv.) in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction then stopped after 45 minutes. To verify that the free thiols of the reduced dTT have formed a reduction-resistant thio-ether bond as a result of conjugation, or re-oxidized into di-sulfide bond, the conjugated product was treated with 100 Eq of DTT for 1 h then washed by centrifugal filtration, and then the thiol content was measured before and after the reducing treatment. The free thiol dosage was measured by an Ellman test using a cysteine standard curve. The protein concentration was measured by a Bradford assay using a BSA standard curve.

Figure 21:
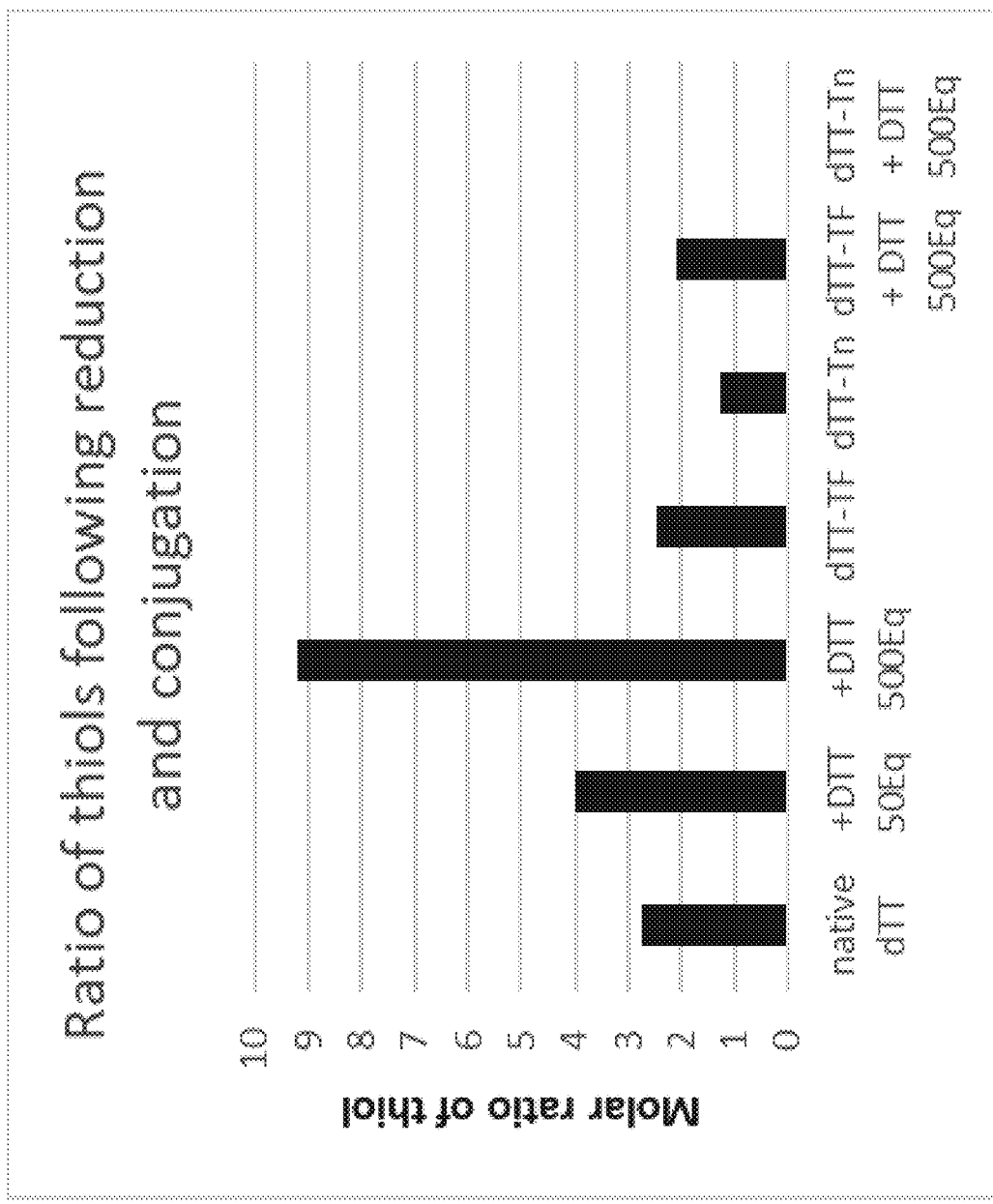
FIG. 21 shows the molar ratio of thiols of dTT at various steps of the photocatalytic thiol-ene conjugation reaction and following reduction of the conjugated dTT.

FIG. 21 shows the molar ratio of free thiols in dTT after the different conjugation conditions. The results indicate that the dTT protein was reduced in a dose-dependent manner and reached 9 free thiols upon treatment with 500 Eq DTT (out of a maximal theoretical number of 10 cysteines in dTT). Conjugation of O-Allyl-Tn or O-Allyl-TF by the thiol-ene photo-reaction lowered the free thiol to at or below the level of the non-reduced dTT. The resistance of the dTT-Tn conjugate to reduction confirmed the presence of a reduction-resistant thio-ether bond that formed by the thiol-ene photo reaction.

To measure the immunoreactivity of the dTT samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 1/100 dilution of the lectin *Vicia Villosa* or Peanut Agglutinin coupled to the horseradish peroxidase (VVA-hrp, PNA-hrp EY LAbs), or 0.1 µg/mL of TF-specific purified murine monoclonal antibody JAAF11. After an incubation of 1 h at RT with gentle shaking or 12 h at 4° C., the wells with JAAF11 were washed with PBS-T then further incubated for 60 minutes with 100 µL of 1/1000 dilution of the secondary antibody goat anti-mouse IgG (H+L)-hrp (Jackson Immunoresearch). After an incubation of 1 h at RT with gentle shaking or 12 h at 4° C., the plate washed 4 times with PBS-T and 100 µL of hrp substrate was added (Ultra TMB-ELISA, Thermo Scientific) to each well. The reaction was stopped by the addition of 100 µL of 0.5N sulfuric acid and the plate was read in a plate reader at 450 nm (Biotek EL808).

Figure 22:
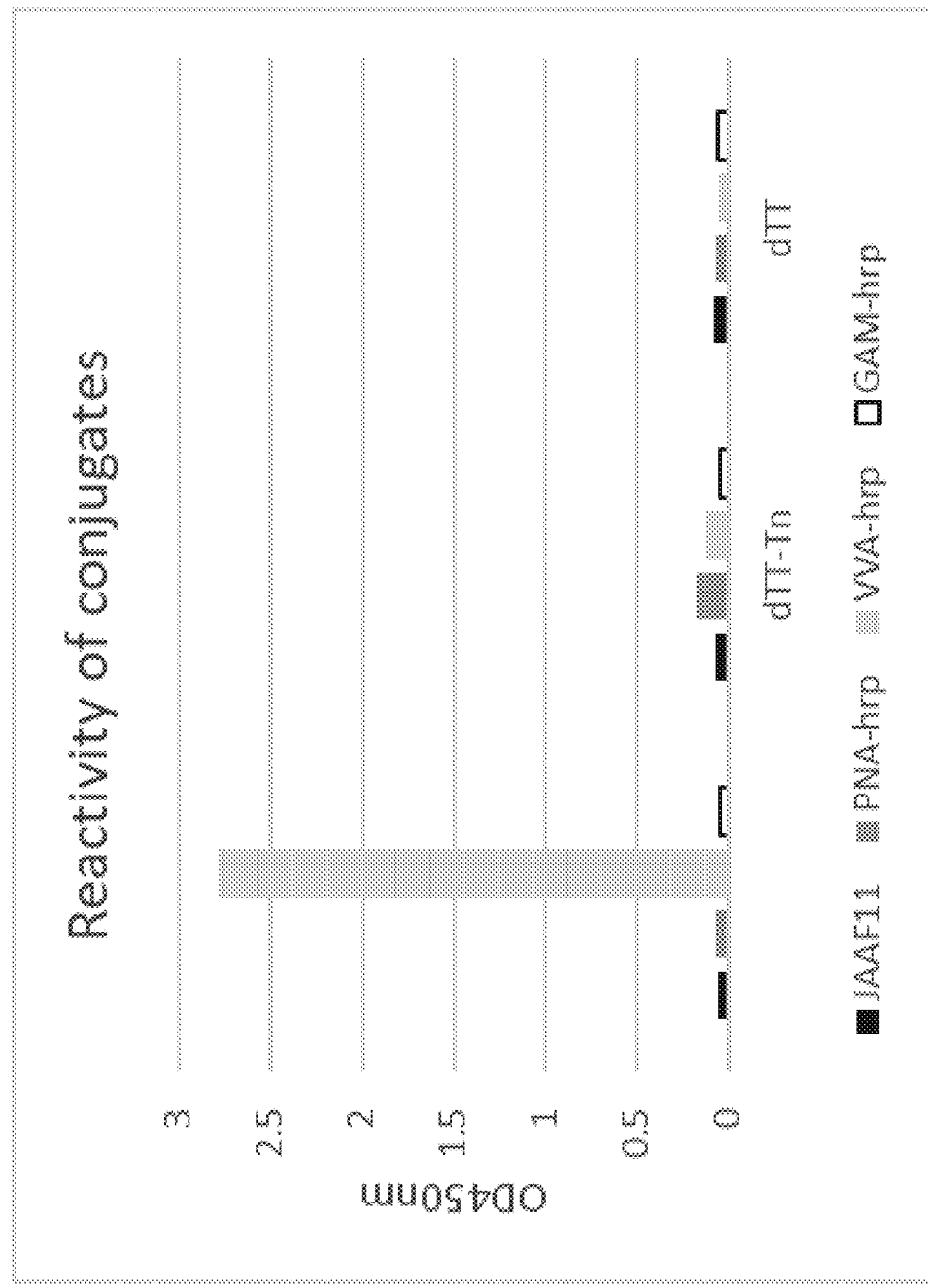
FIG. 22 shows the reactivity to lectins and anti-TF mAb of dTT conjugated by the photocatalytic thiol-ene conjugation reaction to O-Allyl-Tn.

FIG. 22 shows the high reactivity of the dTT-Tn conjugate to the lectin VVA compared to the unconjugated dTT.

The native dTT and dTT-Tn conjugate were analyzed by SDS-PAGE electrophoresis on a 10% polyacrylamide gel, then stained with Coomassie blue. The gel electrophoresis results showed that the dTT-Tn conjugate migrated at higher molecular weight than the native non-conjugated dTT (data not shown).

Example 17: Effect of AAPH Concentration on the Conjugation of O-Allyl-Tn to Chemically Thiolated dTT by Thiol-Ene Photoreactivity dTT was dialysed in PBS pH 8 (MWCO 30,000) then 100 µL (0.8 mg) was stirred with 200 Eq/protein of a solution of 0.1 M 2-imminothiolane hydrochloride in water (Sigma), 200 Eq/protein of 0.1 M O-Allyl-TF in water, and 0.8 Eq/protein or approximately 450 Eq/protein AAPH in water in a final volume of 124 µL in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction. Samples were retrieved during the photoreaction at 15 minutes and at the completion of the reaction at 45 minutes. The conjugation product was buffer exchanged to PBS pH 7.4 by size exclusion chromatography using Sephadex™ G25-filled mini-spin column. The free thiol concentration was measured by Ellman assay using a cysteine standard curve. The protein concentration was measured by a Bradford assay using BSA as standard.

Figure 23:
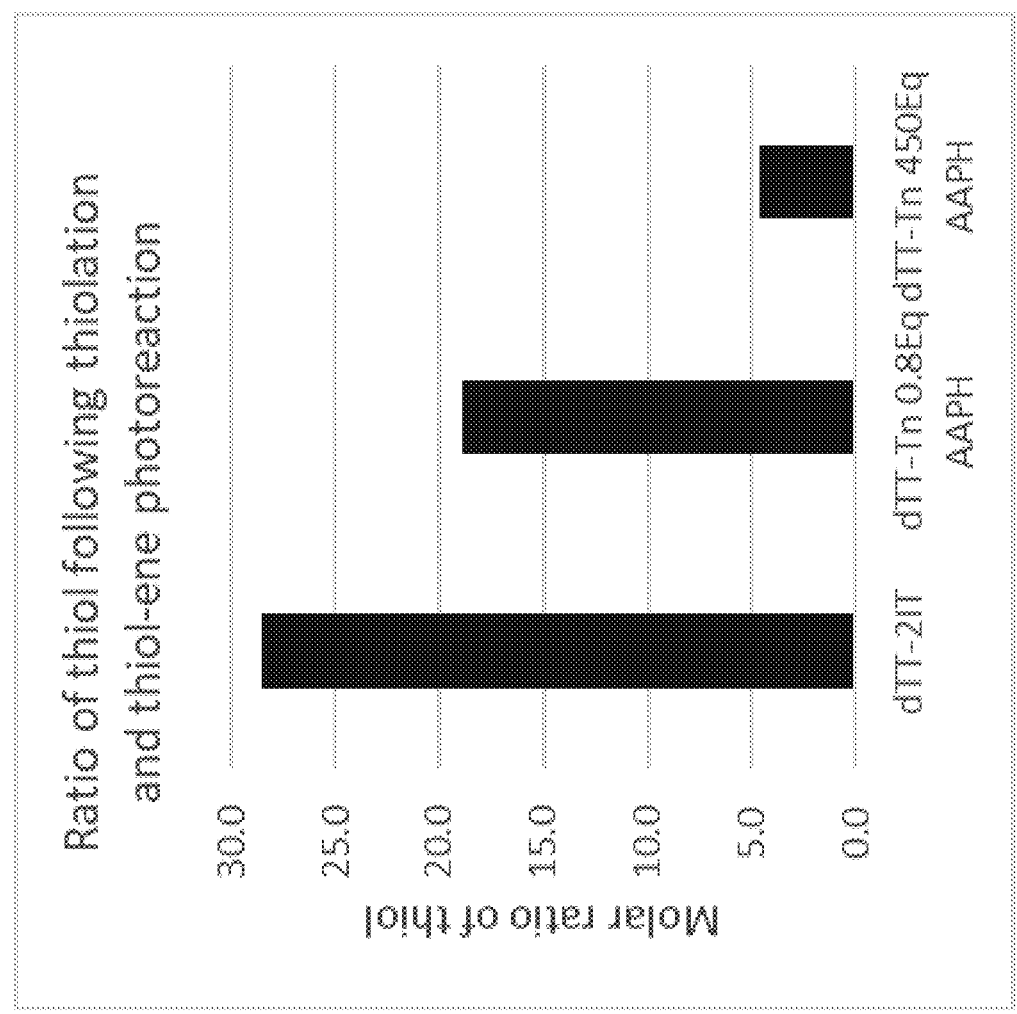
FIG. 23 shows the molar ratio of thiol of chemically thiolated dTT conjugated or not by the photocatalytic thiol-ene conjugation reaction with O-Allyl-Tn in the presence of low or high amount of AAPH.

FIG. 23 shows that the ratio of free thiol in the dTT samples subsequent to chemical thiolation with 2-imminothiolane and thiol-ene photoreaction in the absence of O-Allyl-Tn reaches 25-30, while the presence of O-Allyl-Tn reduces the thiol ratio of dTT to approximately 20 and 5 in a dose-dependent manner respective to the AAPH concentration, suggesting that a thio-ether bond was formed by the thiol-ene photo-reaction.

To measure the immunoreactivity of the dTT samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 1/100 dilution of the lectin *Vicia Villosa* coupled to the horseradish peroxidase (VVA-hrp, EY LAbs). After an incubation of 1 h at RT with gentle shaking or 12 h at 4° C., the plate washed 4 times with PBS-T and 100 µL of hrp substrate was added (Ultra TMB-ELISA, Thermo Scientific) to each well. The reaction was stopped by the addition of 100 µL of 0.5N sulfuric acid and the plate was read in a plate reader at 450 nm (Biotek EL808).

Figure 24:
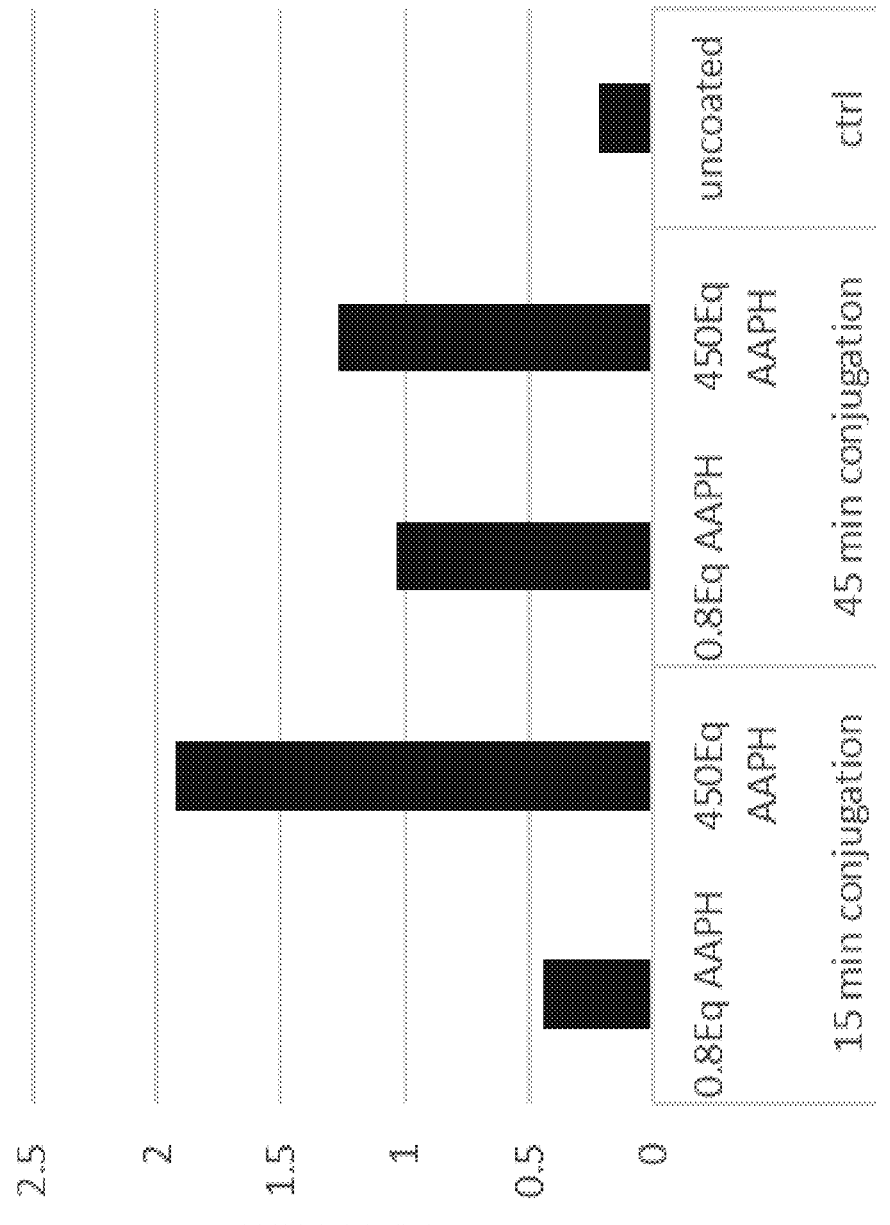
FIG. 24 shows the reactivity of the lectin *Vicia Villosa* to chemically thiolated dTT conjugated by the photocatalytic thiol-ene conjugation reaction with O-Allyl-Tn in the presence of low or high amount of AAPH at two different times.

FIG. 24 shows the reactivity of dTT samples to the lectin VVA-hrp. Higher reactivity of Tn conjugates compared to native unconjugated dTT was observed. Further, the reactivity correlated with the duration of the photo-reaction and the amount of AAPH activator used.

The dTT conjugates (5 µg) were analyzed by SDS-PAGE electrophoresis on a 10% polyacrylamide gel either stained with Coomassie blue or transferred to a membrane (Immobilon-P, Merck Millipore) for western blot analysis. The membrane was blocked in PBS-T+1% BSA for 1 h, washed with PBS-T, then incubated with a 1/100 dilution of the lectin *Vicia Villosa* coupled to the horseradish peroxidase (VVA-hrp, EY LAbs) in PBS-T for 1 h at RT or overnight at 4° C. The membrane was then extensively washed with PBS-T and the bound VVA-hrp was detected with the horseradish peroxidase chromogenic substrate 4-Chloro 1-Naphthol (0.3 mg/mL in PBS containing 0.03% hydrogen peroxide, Sigma). The results from both the Coomassie-stained SDS-PAGE and corresponding Western blot stained with VVA-hrp, revealed that the dTT-Tn migrated at a higher molecular weight than the native dTT, and was specifically reactive to VVA, indicating that the product is indeed conjugated to Tn (data not shown).

Example 18: Conjugation of O-Allyl-Tn and O-Allyl-TF to Chemically Reduced BSA by Thiol-Ene Photoreaction BSA (7 mg in 1 mL PBS, pH 7.4) was incubated with 600 eq DTT for 2 h then washed in PBS pH 7.4 by centrifugal filtration (MWCO 10,000, Amicon). The reduced protein was then conjugated to O-Allyl-Tn or to O-Allyl-TF by the thiol-ene photoreaction. Reduced BSA (600 uL, 5.3 mg/mL, 0.047 nmol) was stirred with of O-Allyl-sugar (60 eq) and AAPH (4.0 equiv.) and PBS pH 7.4 (720 uL) in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction. After 45 min., the product was washed with PBS pH 7.4 by centrifugal filtration (MWCO 10,000, Amicon) to remove any un-reacted O-Allyl and reagents. The free thiol concentration of the reduced BSA was measured by Ellman assay using a cysteine standard curve, and the protein concentration by a Bradford assay using BSA as standard.

To measure the immunoreactivity of the BSA samples, 1 μg of protein sample was diluted into 100 μL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 μL of a 1/100 dilution of the lectin *Vicia Villosa*, or Peanut agglutinin coupled to the horseradish peroxidase (VVA-hrp, PNA-hrp, EY LAbs) or 0.1 μg/mL of TF-specific purified murine monoclonal antibody JAAF11. After an incubation of 1 h at RT with gentle shaking or 12 h at 4° C., the wells containing JAAF11 were washed with PBS-T then further incubated for 60 minutes with secondary antibody goat anti-mouse IgG (H+L)-hrp (Jackson Immunoresearch). Wells were then washed 4 times with PBS-T and 100 μL of hrp substrate was added (Ultra TMB-ELISA, Thermo Scientific) to each well. The reaction was stopped by the addition of 100 μL of 0.5N sulfuric acid and the plate was read in a plate reader at 450 nm (Biotek EL808).

Figure 25:
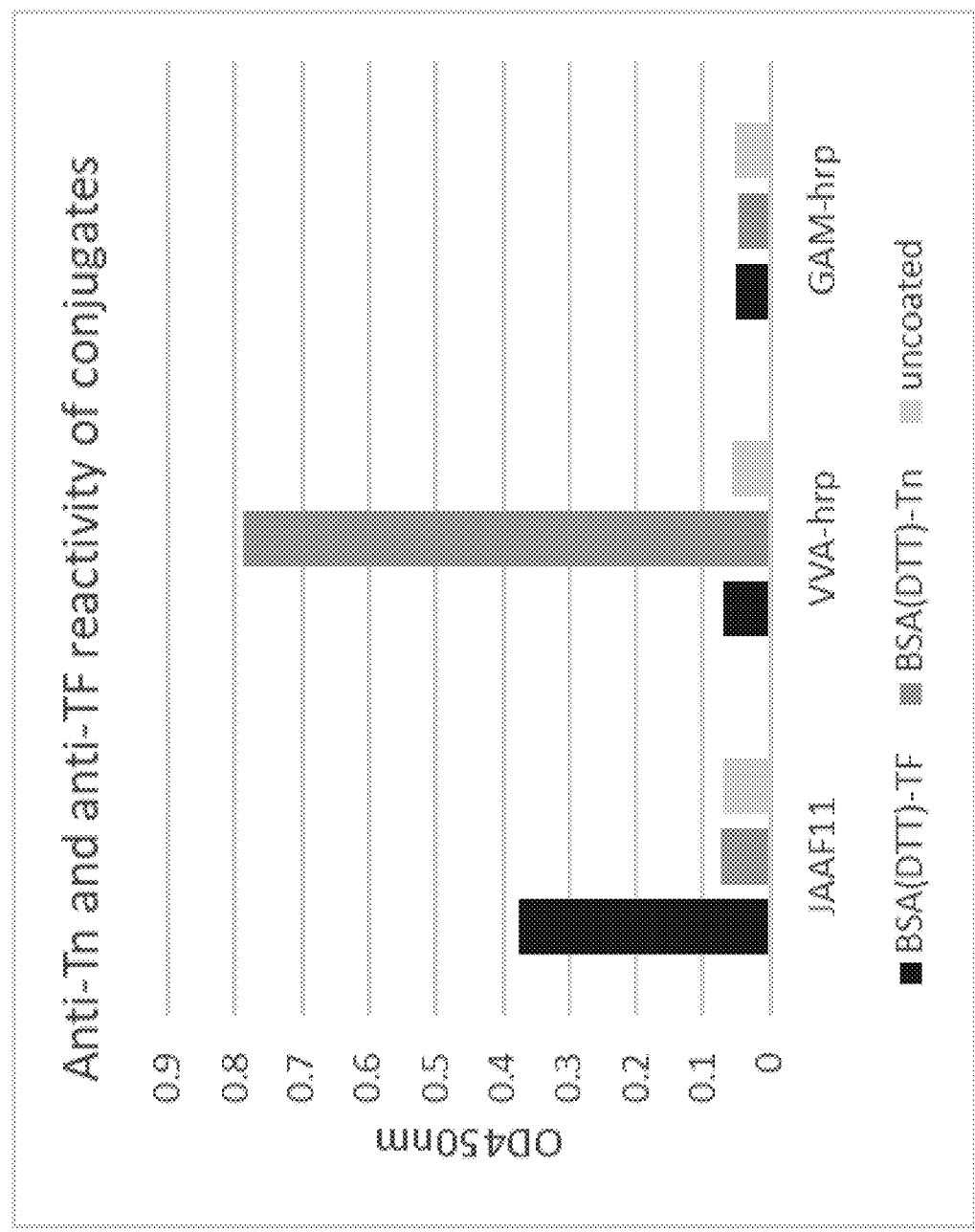
FIG. 25 shows the reactivity of lectins and anti-TF antibody to reduced BSA conjugated by the photocatalytic thiol-ene conjugation reaction with O-Allyl-Tn.

FIG. 25 shows that the BSA-TF and BSA-Tn generated under these conditions were highly reactive and specific to anti-TF JAAF11 monoclonal antibody and for the anti-Tn lectin VVA, respectively.

The BSA-Tn and BSA-TF conjugates (5 μg) were analyzed by SDS-PAGE electrophoresis on a 10% polyacrylamide gel stained with Coomassie blue. The reduction of BSA under the conditions used generated a molar ratio of 19.29 thiols as measured by the Ellman test. Following conjugation with either O-Allyl-sugars, the Ellman's test was negative, suggesting that the free thiols were chemically coupled to the O-Allyl sugars by the thiol-ene photoreaction (data not shown). The Coomassie-stained SDS-PAGE gel showed both BSA-conjugates migrated at the expected molecular weight of BSA, and to higher molecular weight species (data not shown).

Example 19: Conjugation of O-Allyl-Tn to Chemically Reduced BSA by Thiol-Ene Photoreaction BSA (500 μL, 7 mg/mL) was incubated with 400, 200 or 1000 Eq of DTT (0.5 M) for 1 h at RT and rotation. The reduced BSA solution was then dialysed overnight in PBS pH 7.4. The free thiol concentration of the reduced BSA was then measured by Ellman assay using a cysteine standard curve, and the protein concentration by a Bradford assay using BSA as standard, from which the molar ratio of free thiol/BSA was calculated.

Figure 26:
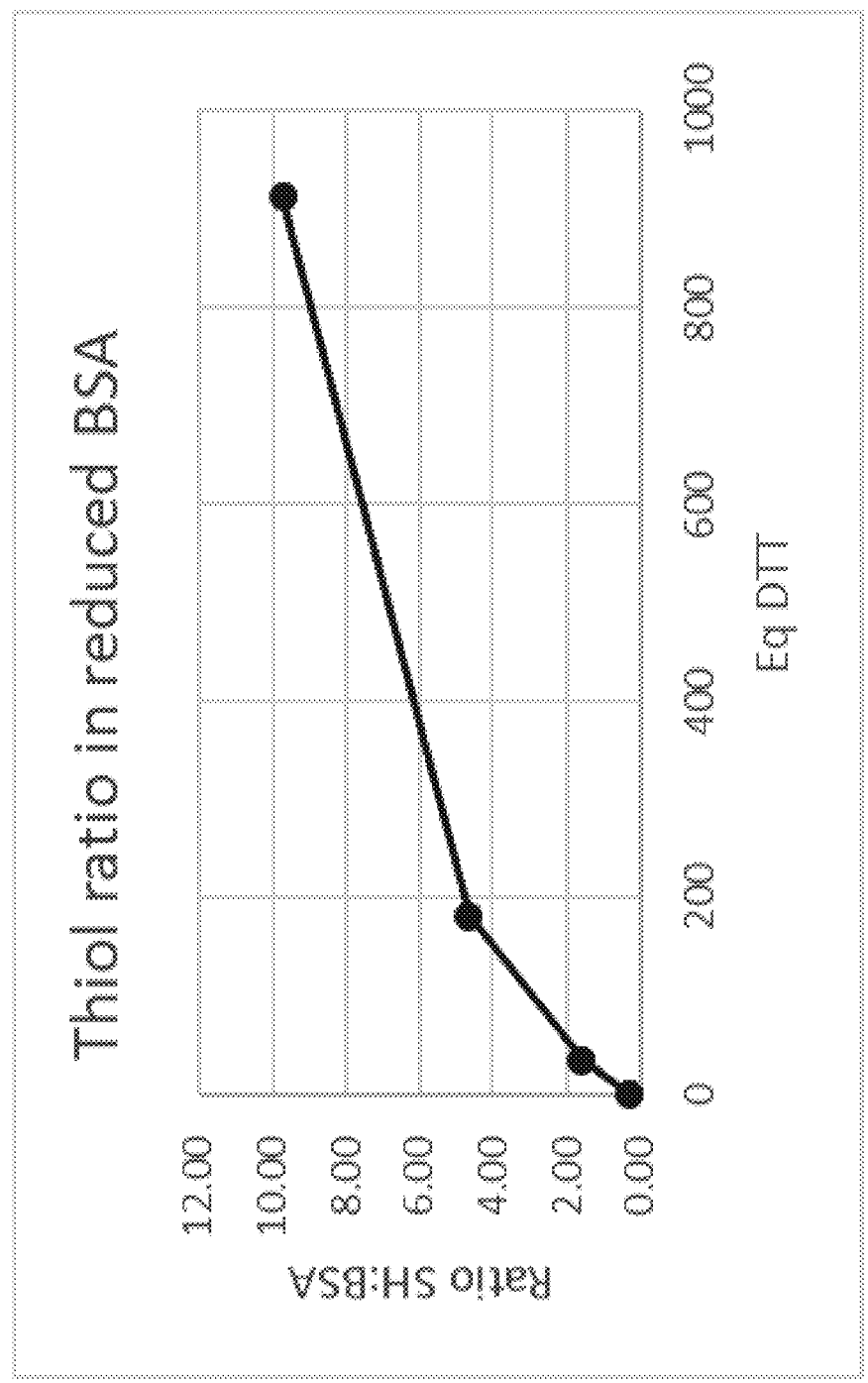
FIG. 26 shows the relationship between the reducing conditions and the molar ratio of thiols of reduced BSA.

FIG. 26 shows a correlation between the amount of free thiol generated and the amount of the reducing agent DTT, which reaches about 10 thiol/BSA when the reduction was conducted with 1000 Eq DTT under the conditions employed.

The reduced protein was then conjugated to various ratios of O-Allyl-Tn. Reduced BSA (5 nmols) was stirred with 100 Eq of O-Allyl-Tn/reduced BSA or 100 Eq of O-Allyl-Tn/BSA-thiol with AAPH and PBS pH 7.4 in a final volume of 500 μL in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction. After 45 minutes, the product was washed with PBS pH 7.4 by centrifugal filtration (MWCO 10,000, Amicon) to remove unreacted 0-Allyl and reagents.

To measure the immunoreactivity of the BSA samples, 1 μg of protein sample was diluted into 100 μL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 μL of a 1/100 dilution of the lectin *Vicia Villosa*, coupled to the horseradish peroxidase (VVA-hrp, EY LAbs) or 0.1 μg/mL of TF-specific purified murine monoclonal antibody JAAF11. After an incubation of 1 h at RT with gentle shaking or 12 h at 4° C., the wells containing JAAF11 were washed with PBS-T then further incubated for 60 minutes with secondary antibody goat anti-mouse IgG (H+L)-hrp (Jackson Immunoresearch). After an incubation of 1 h at RT with gentle shaking or 12 h at 4° C., the plate was washed 4 times with PBS-T and 100 ul of hrp substrate was added (Ultra TMB-ELISA, Thermo Scientific) to each well. The reaction was stopped by the addition of 100 μL of 0.5N sulfuric acid and the plate was read in a plate reader at 450 nm (Biotek EL808).

Figure 27:
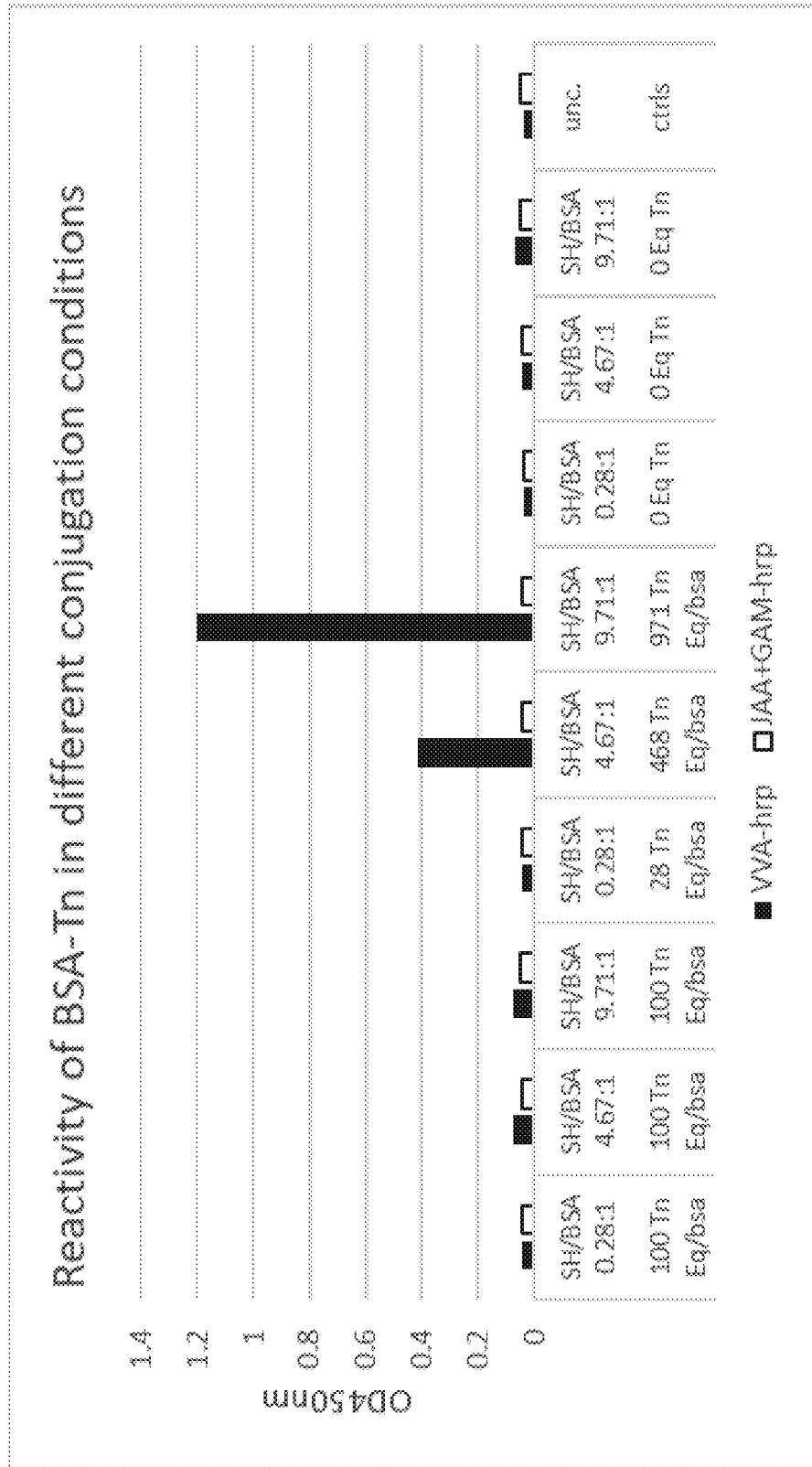
FIG. 27 shows the reactivity of the Tn-specific *Vicia Villosa* lectin and anti-TF antibody to BSA with various free thiol molar ratio and conjugated by the photocatalytic thiol-ene conjugation reaction with various amount of O-Allyl-Tn.

FIG. 27 shows the reactivity of the various BSA-Tn conjugates to the lectin VVA and to the anti-TF monoclonal antibody JAAF11 (+goat anti-mouse IgG-hrp conjugate). Two of the BSA-conjugates, conjugated at the highest ratio of O-Allyl, were found to be highly reactive to VVA specifically, as a result of the thiol-ene photoreaction.

The BSA-Tn conjugates (5 μg) were analyzed by SDS-PAGE electrophoresis on a 10% polyacrylamide gel either stained with Coomassie blue or for glycoproteins according to the manufacturer's instructions (Pierce). The results showed that the BSA conjugates that migrated at a high molecular weight were positively stained for glycan, while the native unconjugated BSA was not (data not shown).

Example 19: Conjugation of O-Allyl-TF to Chemically Thiolated BSA by Thiol-Ene Photoreaction BSA (1 mL, 0.088 μmol, 5.89 mg/mL, PBS pH 8.0) was incubated with 5, 10, or 20 Eq of 2-imminothiolane (5, 10, 20 μL, 0.1 mmol/mL) for 1 h. Thiolated BSA was then washed by centrifugal filtration (MWCO 10,000, Amicon) to remove unreacted reagents before conjugating to O-Allyl-TF by thiol-ene photoconjugation. Thiolated BSA (440; 480; 575 μL, 6.8; 6.4; 5.2 mg/mL) was stirred with 3 eq/thiol of O-Allyl-Tn and AAPH (0.2 Eq/thiol) and PBS pH 7.4 in a final volume of 1 mL in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction. After 1 h, the product was washed with PBS pH 7.4 by centrifugal filtration (MWCO 10,000, Amicon) to remove un-reacted O-Allyl and other reagents. The free thiol concentrations of the BSA samples were measured by Ellman assay using a cysteine standard curve, and the protein concentration by a Bradford assay using BSA as standard.

To measure the immunoreactivity of the BSA samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 1/100 dilution of the lectin peanut agglutinin coupled to the horseradish peroxidase (PNA-hrp, EY LAbs), or 0.1 µg/mL of TF-specific purified murine monoclonal antibody JAAF11. After an incubation of 1 h at RT with gentle shaking or 12 h at 4° C., the wells containing JAAF11 were washed with PBS-T then further incubated for 60 minutes with secondary antibody goat anti-mouse IgG (H+L)-hrp (Jackson Immunoresearch). Wells were then washed 4 times with PBS-T and 100 µL of hrp substrate was added (Ultra TMB-ELISA, Thermo Scientific) to each wells. The reaction was stopped by the addition of 100 µL of 0.5 N sulfuric acid and the plate was read in a plate reader at 450 nm (Biotek EL808).

Figure 28:
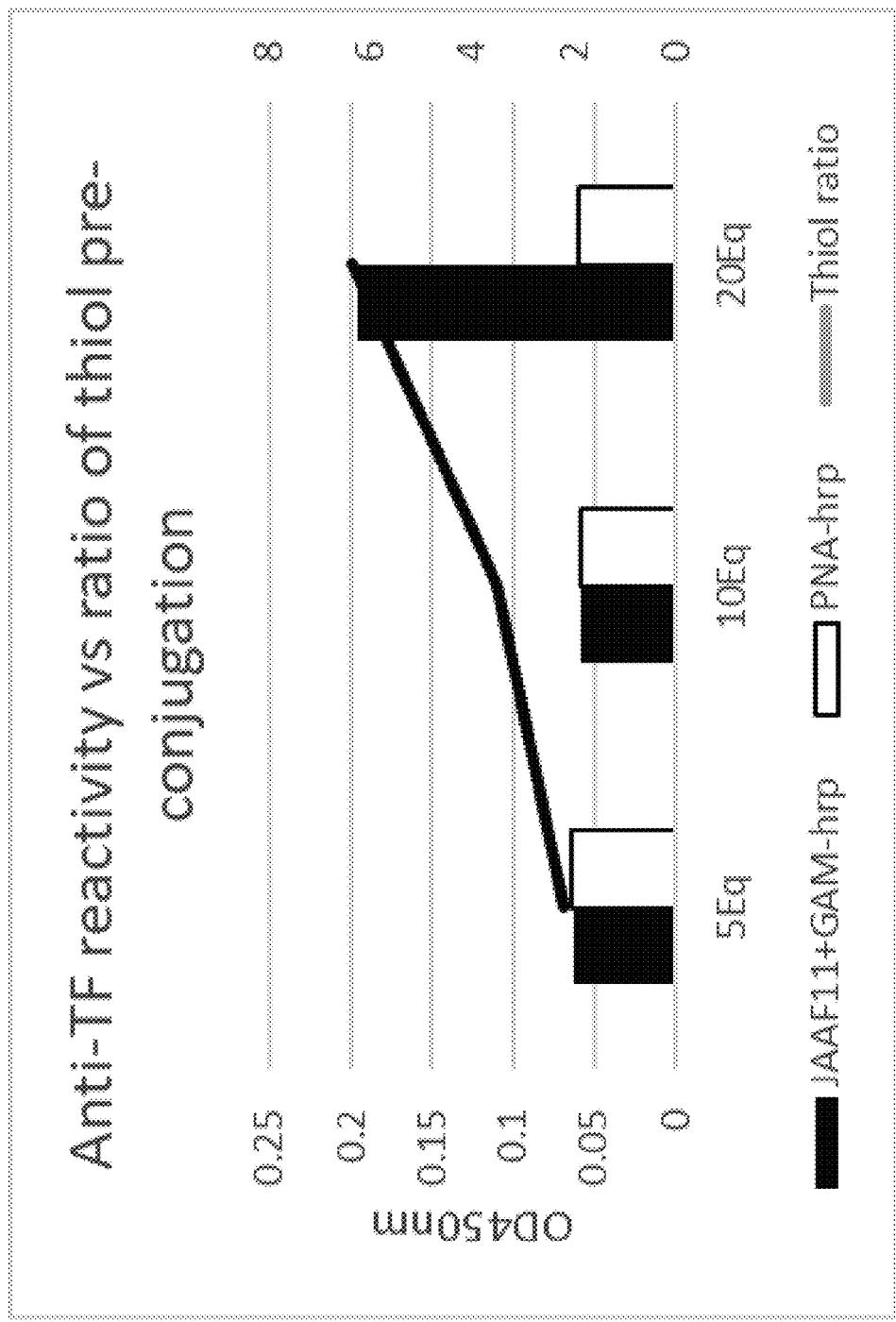
FIG. 28 shows the relationship between the reducing conditions, the molar ratio of thiols of reduced BSA and the TF reactivity of reduced BSA conjugated by the photocatalytic thiol-ene conjugation reaction with O-Allyl-TF.

In FIG. 28, the dual axis graph shows the reactivity of the BSA-TF conjugates to the anti-TF lectin PNA or mAb JAAF11 in relation to the thiol ratio of the respective conjugates measured before TF conjugation. These results show that JAAF11 reactivity is detected with the BSA that was the most thiolated.

Example 20: Conjugation of O-Allyl-Tn to Chemically Thiolated BSA by Thiol-Ene Photoreaction BSA (250 µL, 4.3 mg/mL) was incubated with 200 eq of 0.1 M 2-imminothiolane (Sigma) in the presence or the absence of 200 Eq of 0.1 M O-Allyl-Tn and approximately 450 Eq AAPH and PBS pH 8 in a final volume of 316 µL in a quartz cuvette (10×10 mm path length, Fisher) placed between two hand held UV lamps at 365 nm (0.16 amps, VWR) at a distance of 2-5 cm from the cuvette. The UV was turned on immediately following the addition of AAPH to initiate the reaction. Samples were taken at the indicated time during the reaction. The reaction was stopped after 45 minutes after which the product was buffer exchanged to PBS pH 7.4 by gel filtration chromatography using Sephadex™ G25 mini spin column. The free thiol concentration of the BSA samples were measured by Ellman assay using a cysteine standard curve, and the protein concentration by a Bradford assay using BSA as standard.

Figure 29:
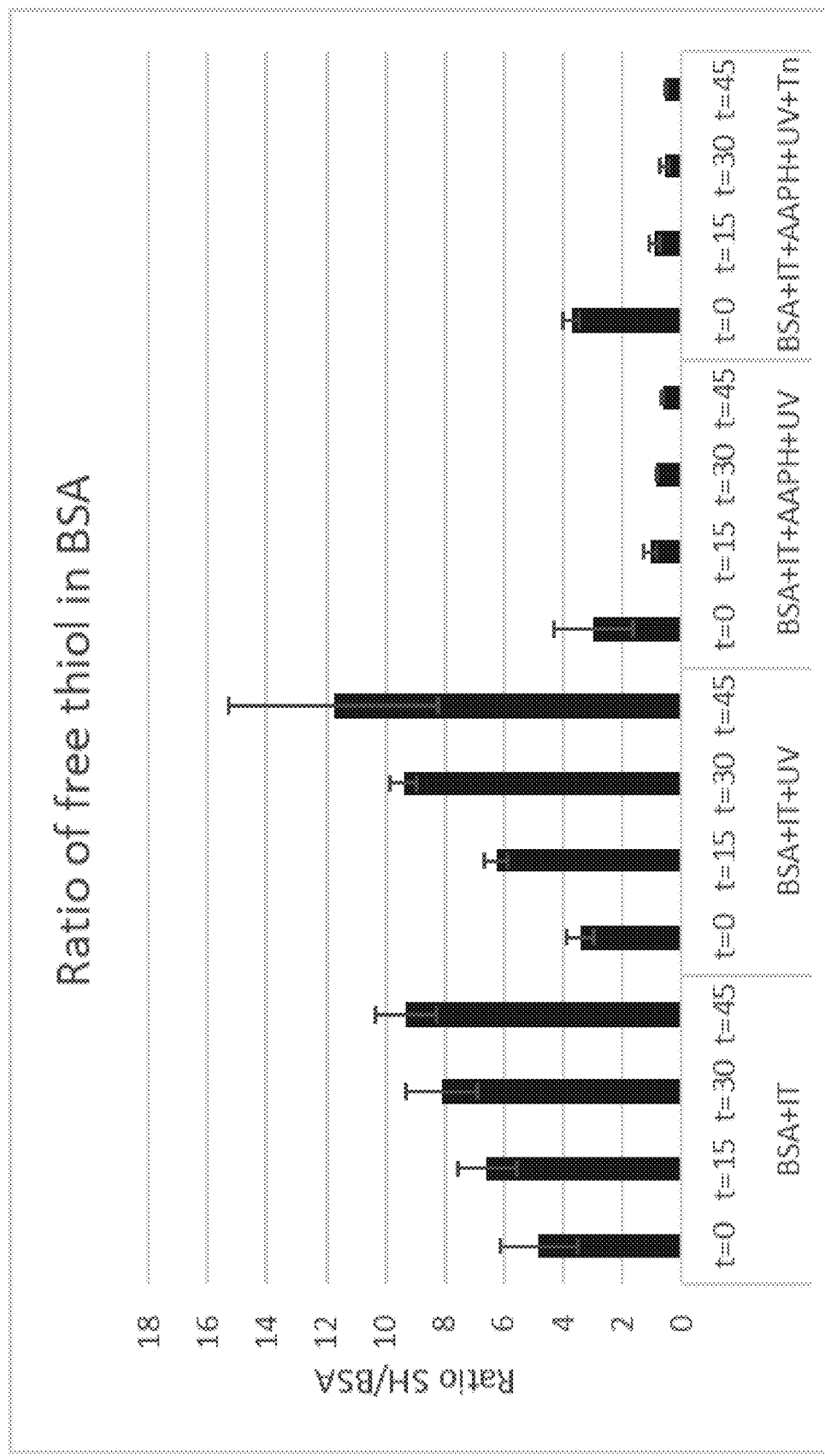
FIG. 29 shows the molar ratio of thiols adducts in BSA in function of time by chemical thiolation alone or thiolation with simultaneous photocatalytic thiol-ene conjugation reaction in the presence or absence of AAPH and O-Allyl-Tn.

FIG. 29 shows a time-dependent increase of free thiol function upon reaction of the BSA with 2-imminothiolane alone or in the presence of 365 nm light, while the addition of AAPH in the presence or the absence of O-Allyl-Tn in the photoreaction prevent the formation of detectable free thiols.

To measure the immunoreactivity of the BSA samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 1/100 dilution of the lectin *Vicia Villosa* coupled to the horseradish peroxidase (VVA-hrp, EY Labs). After an incubation of 1 h at RT with gentle shaking or 12 h at 4° C., the wells were then washed 4 times with PBS-T and 100 µL of hrp substrate was added (Ultra TMB-ELISA, Thermo Scientific) to each wells. The reaction was stopped by the addition of 100 µL of 0.5 N sulfuric acid and the plate was read in a plate reader at 450 nm (Biotek EL808).

Figure 30:
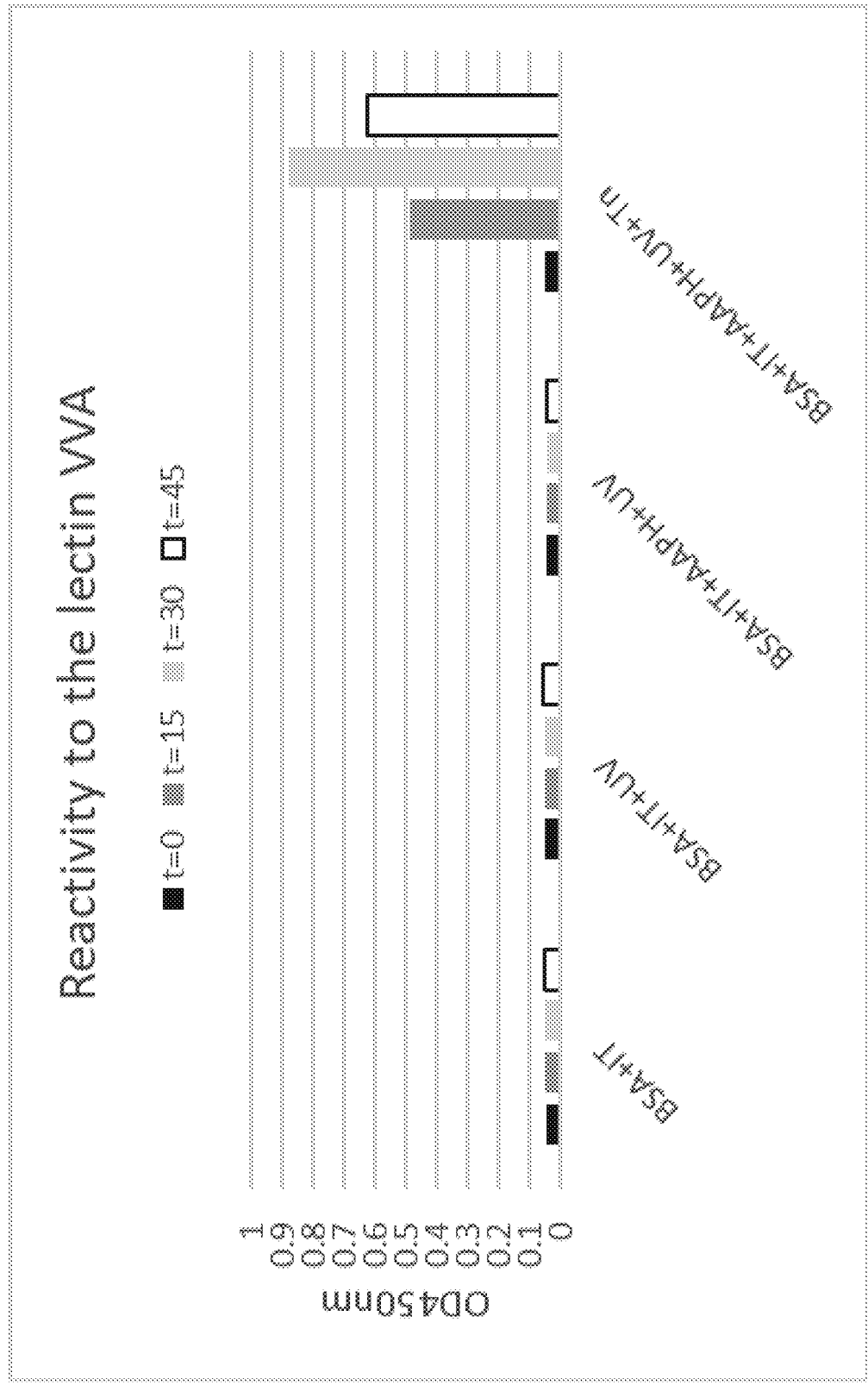
FIG. 30 shows the reactivity of the Tn-specific *Vicia Villosa* lectin with thiolated BSA or BSA simultaneously thiolated and conjugated by photocatalytic thiol-ene conjugation reaction in the presence or absence of AAPH and O-Allyl-Tn.

In FIG. 30, the reactivity of the BSA conjugates to the lectin VVA indicates that only the BSA generated by the thiol-ene photoreaction in the presence of O-Allyl-Tn is detected by the VVA, while the product generated in the absence of O-Allyl-Tn is negative in the ELLA. These results suggest that the AAPH and UV365 nm light catalyse the re-oxidation of the free disulfide into di-sulfide in the absence of O-Allyl-sugar, which competes with the formation of thio-ether bond in the presence of O-Allyl-Tn.

Example 21: Conjugation of O-Allyl-Tn to Chemically Thiolated BSA by Thiol-Ene Photoreaction BSA (250 µL, 4.3 mg/mL) was incubated with 200 Eq of 0.1 M 2-imminothiolane (Sigma), 200 Eq of 0.1 M O-Allyl-Tn, and either 0.8 Eq of AAPH or approximately 450 Eq AAPH and PBS pH 8 in a final volume of 316 µL in a quartz cuvette (10×10 mm path length, Fisher). The effect of the anti-oxidant Vitamin C (approx. 5 mM) on conjugation was tested in the condition containing a high amount of AAPH. The cuvettes were placed between two hand held UV lamps at 365 nm (0.16 amps, VWR) at a distance of 2-5 cm from the cuvette. The UV was turned on immediately following the addition of AAPH to initiate the reaction. Samples were taken at the indicated time during the reaction. The reaction was stopped after 45 minutes after which the product was buffer exchanged to PBS pH 7.4 by gel filtration chromatography using Sephadex™ G25 mini spin column. The free thiol concentration of the conjugated BSA samples was measured by Ellman assay using a cysteine standard curve, and the protein concentration by a Bradford assay using BSA as standard.

To measure the immunoreactivity of the BSA samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 1/100 dilution of the lectin *Vicia Villosa* coupled to the horseradish peroxidase (VVA-hrp, EY Labs). After an incubation of 1 h at RT with gentle shaking or 12 h at 4° C., the wells were then washed 4 times with PBS-T and 100 µL of hrp substrate was added (Ultra TMB-ELISA, Thermo Scientific) to each well. The reaction was stopped by the addition of 100 µL of 0.5 N sulfuric acid and the plate was read in a plate reader at 450 nm (Biotek EL808).

Figure 31:
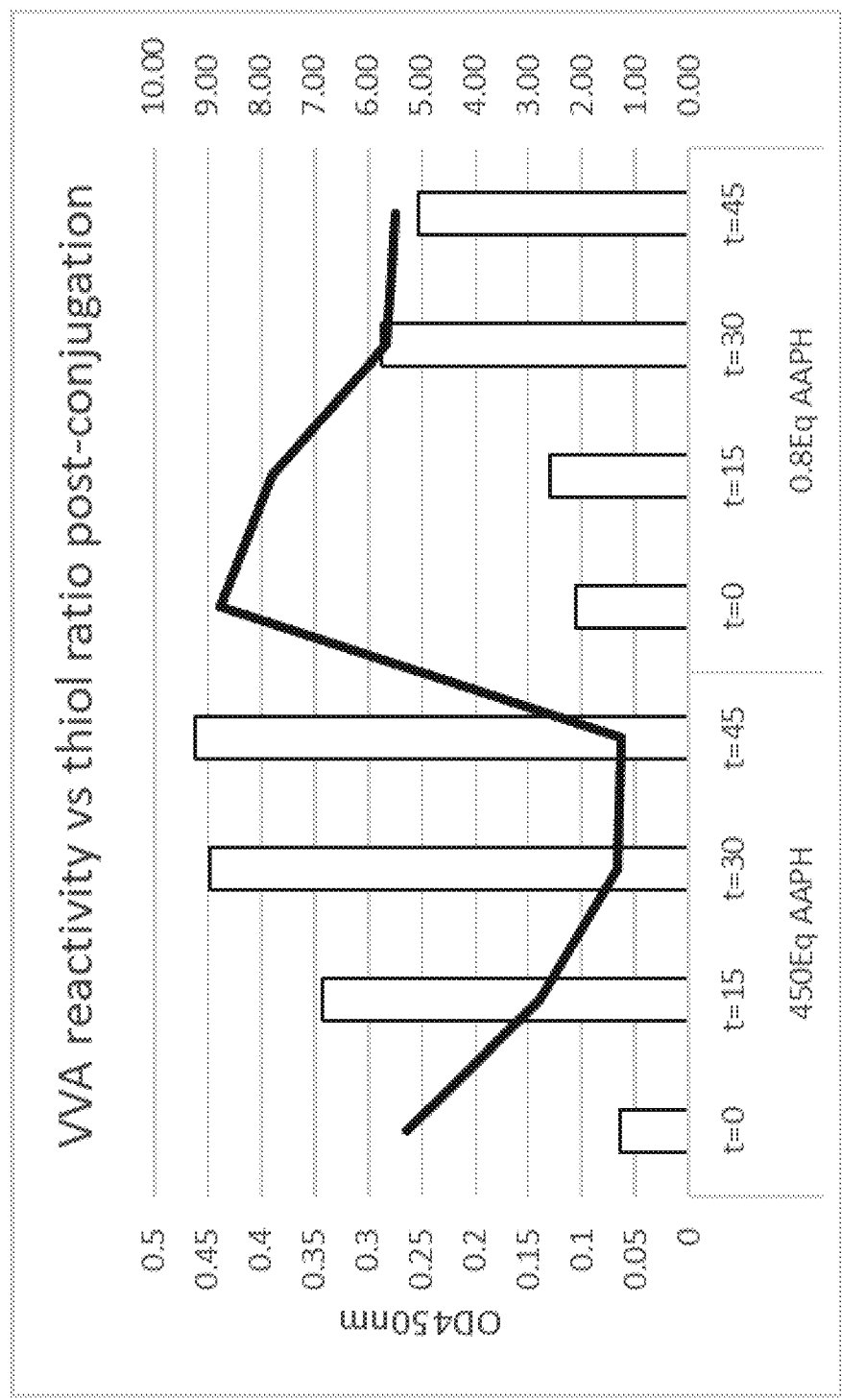
FIG. 31 shows the relationship between the thiol molar ratio and the reactivity of the Tn-specific *Vicia Villosa* lectin of BSA conjugated by the photocatalytic thiol-ene conjugation reaction with O-Allyl-Tn in a function of time.

FIG. 31 having a dual Y-axis shows an increase in reactivity of the conjugation product to the lectin VVA as a function of time, and a corresponding decrease in free-thiol as a result of the thiol-ene photoconjugation of the O-Allyl-Tn to BSA. These results suggest that the reaction was more effective at higher concentrations of AAPH. Product generated in the presence of vitamin C was not reactive to the VVA lectin (not shown).

The BSA-Tn conjugates (5 µg) were analyzed by SDS-PAGE electrophoresis on a 10% polyacrylamide gel stained with Coomassie blue. The results showed a higher amount of high molecular weight species in the reaction at high AAPH than at lower AAPH. Vitamin C prevented the formation of high molecular weight species (data not shown).

Example 22: Conjugation of O-Allyl-Tn to BSA by Thiol-Ene Photoreaction in Function of Protein Thiolation BSA (93 µL, 11.7 mg/mL) was incubated with 200 Eq of 0.1 M 2-imminothiolane (Sigma), 200 Eq of 0.1 M O-Allyl-Tn and either 0.08 Eq, 0.8 Eq or approximately 450 Eq AAPH and PBS pH 8 in a final volume of 316 µL in a quartz cuvette (10×10 mm path length, Fisher). In some samples, the 2-imminothiolane and/or the AAPH was omitted and replaced by PBS pH 8. The cuvette was placed between two hand held UV lamps at 365 nm or at 254 nm (0.16 amps, VWR) at a distance of 2-5 cm from the cuvette. The UV was turned on immediately following the addition of AAPH to initiate the reaction. The reaction was stopped after 45 minutes after which the product was buffer exchanged to PBS pH 7.4 by gel filtration chromatography using Sephadex™ G25 mini spin column. The protein concentration was measured by a Bradford assay using BSA as standard.

To measure the immunoreactivity of the BSA samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 1/100 dilution of the lectin *Vicia Villosa* coupled to the horseradish peroxidase (VVA-hrp, EY Labs). After an incubation of 1 h at RT with gentle shaking or 12 h at 4° C., the wells were then washed 4 times with PBS-T and 100 µL of hrp substrate was added (Ultra TMB-ELISA, Thermo Scientific) to each well. The reaction was stopped by the addition of 100 µL of 0.5 N sulfuric acid and the plate was read in a plate reader at 450 nm (Biotek EL808).

Figure 32:
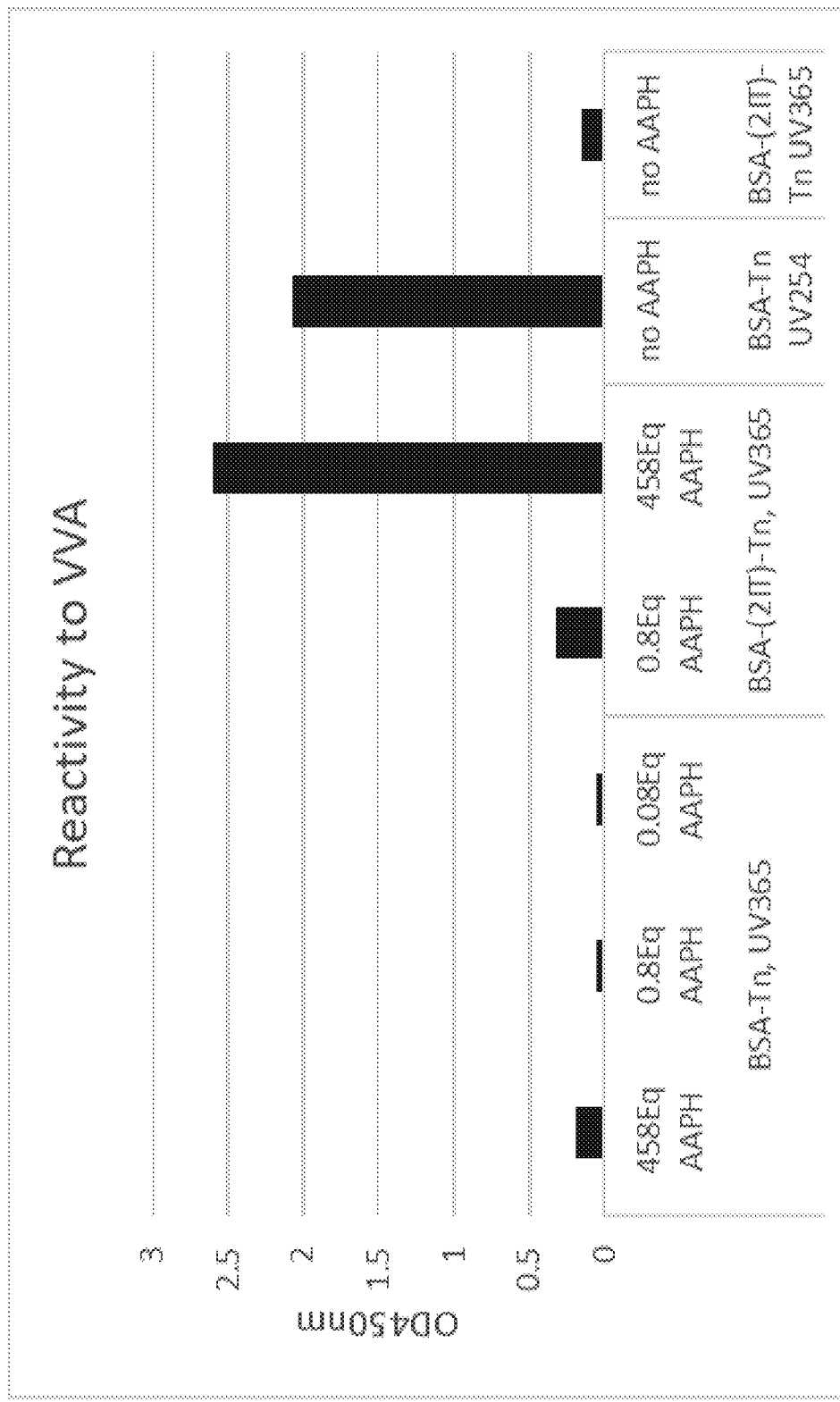
FIG. 32 shows the reactivity of the Tn-specific *Vicia Villosa* lectin to the native or thiolated BSA conjugated by photocatalytic thiol-ene conjugation reaction with O-Allyl-Tn in the presence of low or high amount of AAPH and at two wave-lengths.

FIG. 32 shows the minimal reactivity of product to VVA when the conjugation is performed in absence of protein thiolation or when the thiolated protein is conjugated in the absence of activator AAPH. However, a VVA reactive product is generated by UV254 nm in the absence of protein thiolation and AAPH.

Example 23: Absence of BSA-TF Reactivity at High Conjugation Ratio

BSA (93 µL, 11.7 mg/mL) was incubated in the presence or absence of 200 Eq of 0.1 M 2-imminothiolane (Sigma), 200 Eq of 0.1 M O-Allyl-TF and 0.8 Eq or approximately 450 Eq AAPH and PBS pH 8 in a final volume of 316 µL in a quartz cuvette (10×10 mm path length, Fisher) on the bench at RT or placed between two hand held UV lamps at 365 nm (0.16 amps, VWR) at a distance of 2-5 cm from the cuvette. The UV was turned on immediately following the addition of AAPH to initiate the reaction. The reaction was stopped after 45 minutes after which the product was buffer exchanged to PBS pH 7.4 by gel filtration chromatography using Sephadex™ G25 mini spin column. The protein concentration was measured by a Bradford assay using BSA as a standard. The conjugated galactose of the TF epitope was measured by the method of Dubois using a galactose standard.

To measure the immunoreactivity of the BSA samples, 1 µg of protein sample was diluted into 100 µL of PBS pH 7.4 and allowed to adsorb to the wells of a 96-well plate (Maxisorp, Nunc) for a minimum of 1 h at RT or overnight at 4° C. The wells were then washed twice with PBS-Tween™ 0.05% (PBS-T) and then filled with blocking solution for 30 minutes. The wells were then washed 3 times with PBS-T and filled with 100 µL of a 0.1 µg/mL dilution of the anti-TF monoclonal antibody JAAF11. After an incubation of 1 h at RT with gentle shaking or 12 h at 4° C., the wells were then washed 4 times with PBS-T and further incubated for 60 minutes with 100 µL of 1/1000 dilution of secondary antibody goat anti-mouse IgG (H+L)-hrp (Jackson Immunoresearch). Wells were then washed 4 times with PBS-T and 100 µL of hrp substrate was added (Ultra TMB-ELISA, Thermo Scientific) to each wells. The reaction was stopped by the addition of 100 µL of 0.5 N sulfuric acid and the plate was read in a plate reader at 450 nm (Biotek EL808).

Figure 33:
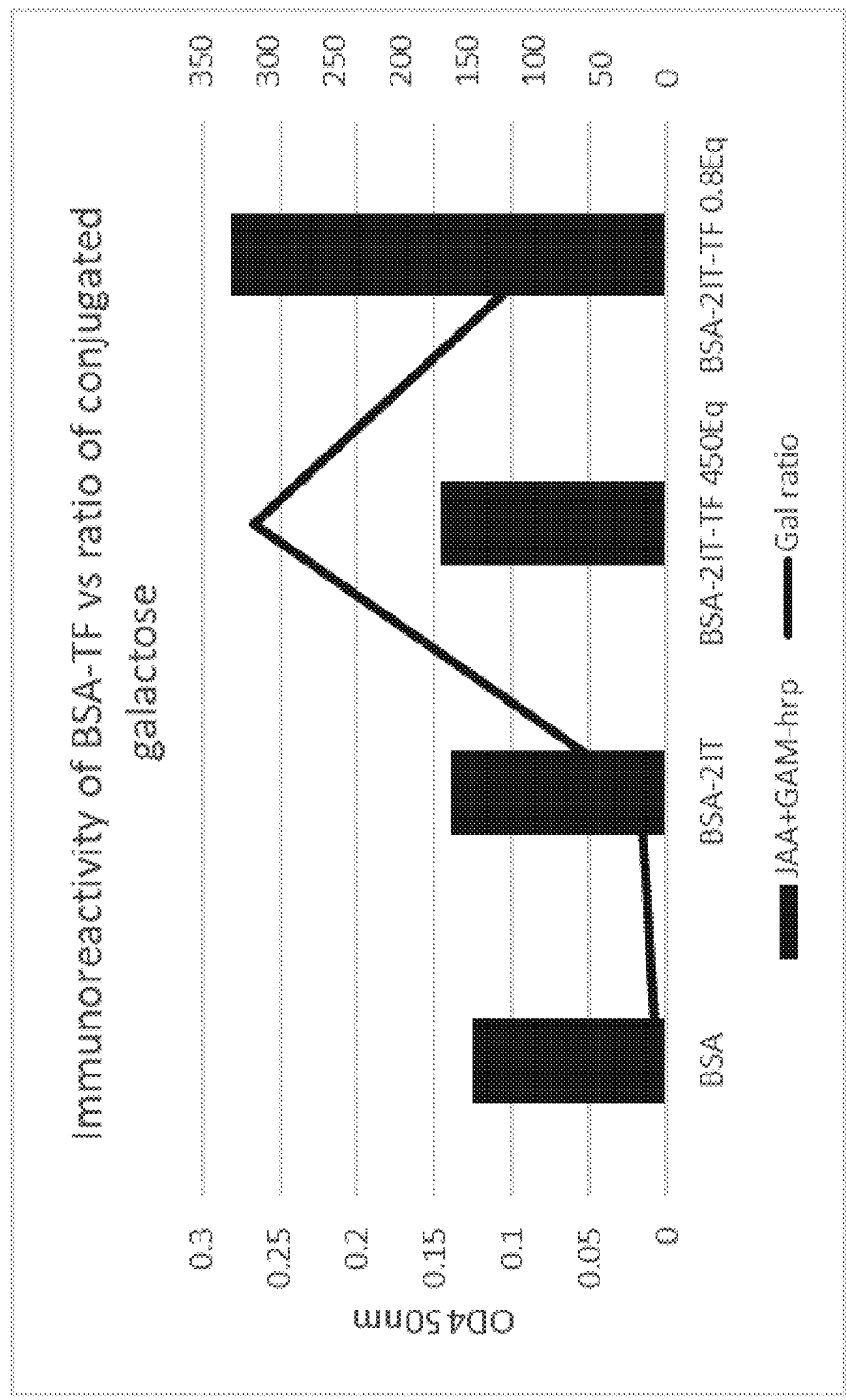
FIG. 33 shows the relationship between the galactose molar ratio and the reactivity of the anti-TF mAb to BSA at different steps of thiolation and photocatalytic thiol-ene conjugation reaction with O-Allyl-Tn at low or high amount of AAPH.

FIG. 33 having a dual Y-axis shows the lower immunoreactivity of the BSA-TF with a high galactose ratio compared to the lower galactose conjugate. The detection of galactose in the two conjugates confirms that TF is conjugated to BSA but conjugated TF immunoreactivity is compromised at high ratio.

Example 24: Conjugation of O-Allyl-Tn to Peptide dTT831-844-Cys-(Tn)-βAla BSA by Thiol-Ene Photoreaction FIG. 34 shows the chemical structures of the dTT831-844-Cys-βAla and the Cys-dTT831-844-βAla with a cysteine residue at the C- and N-terminal, respectively together with their tabulated LC-MS data.

Figure 35:
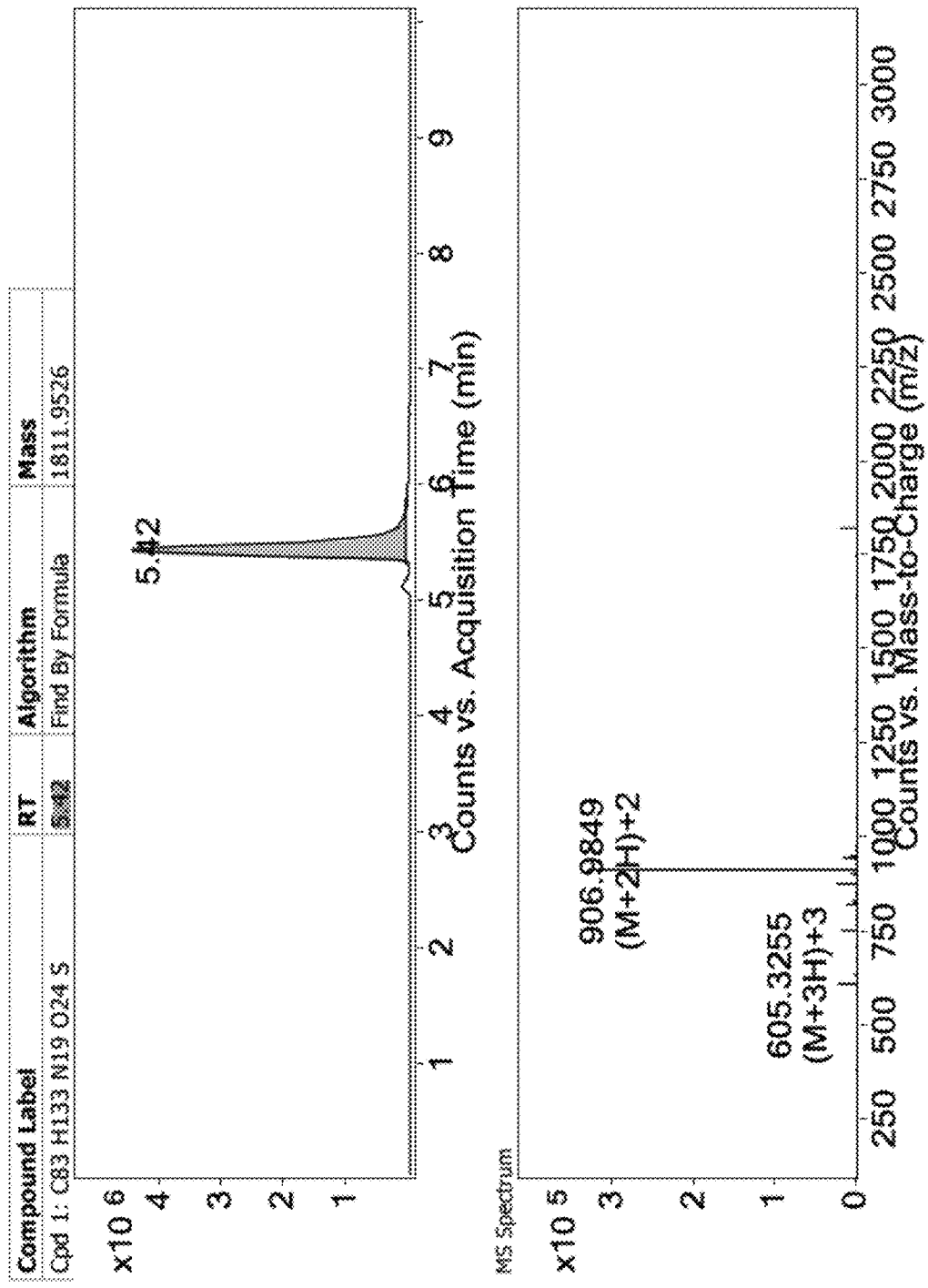
FIG. 35 shows the detailed LC-MS data of the peptide dTT831-844-Cys-βAla.

FIG. 35 shows the detailed LC-MS data of the peptide dTT831-844-Cys-βAla (C-terminal).

Figure 36:
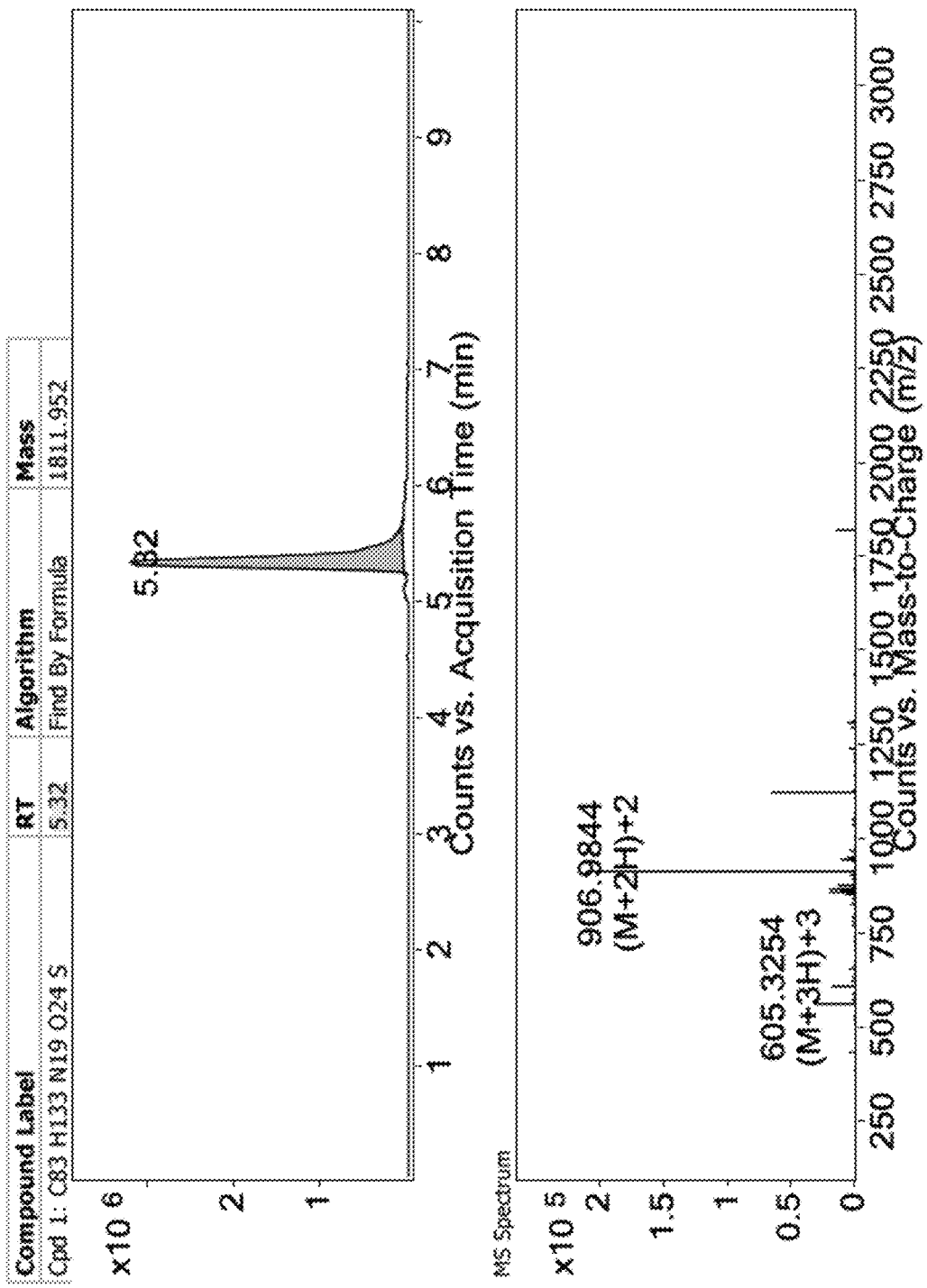
FIG. 36 shows the detailed LC-MS data of the peptide Cys-dTT831-844-βAla.

FIG. 36 shows the detailed LC-MS data of the peptide Cys-dTT831-844-βAla (N-terminal).

Procedure A:

To a solution of peptide in water (1 mL, 2 mM) was added a solution of O-allyl-Tn in H$_2$O (200 µL, 0.1M, 10 equiv) and a catalytic amount of AAPH in UV cuvette. The mixture was stirred at room temperature under 365 nm irradiation for 60 min Ellman's test showed the reaction was finished in 45 min. The solution was then lyophilized to afford the white power and LC-MS showed the presence of desired Tn-conjugated peptide; LC-MS: [M] calcd for C$_{94}$H$_{152}$O$_{31}$N$_{20}$S, 2089.0653. found, 2089.0780. CAN/H$_2$O 5 to 95% 5.08 min.

Procedure B in organic solvent: dTT831-844-Cys-(Tn)-βAla (FIG. 34) To a solution of peptide in MeOH (1 mL, 2 mM) was added a solution of Tn in H$_2$O (200 µL, 0.1M, 10 equiv) and a catalytic amount of DMPAP in UV cuvette. The mixture was stirred at room temperature under 365 nm irradiation for 60 min. Ellman's test showed the reaction was finished in 45 min. The solution was then lyophilized to afford the white power and LC-MS constated the presence of desired peptide-TN. LC-MS: [M] calcd for C$_{94}$H$_{152}$O$_{31}$N$_{20}$S, 2089.0653. found, 2089.0675. CAN/H$_2$O 5 to 95% 5.07 min.

FIG. 37 shows the photolytic AAPH-catalyzed thiol-ene reaction of the O-Allyl Tn on the C-terminal peptide dTT831-844-Cys-βAla.

Figure 38:
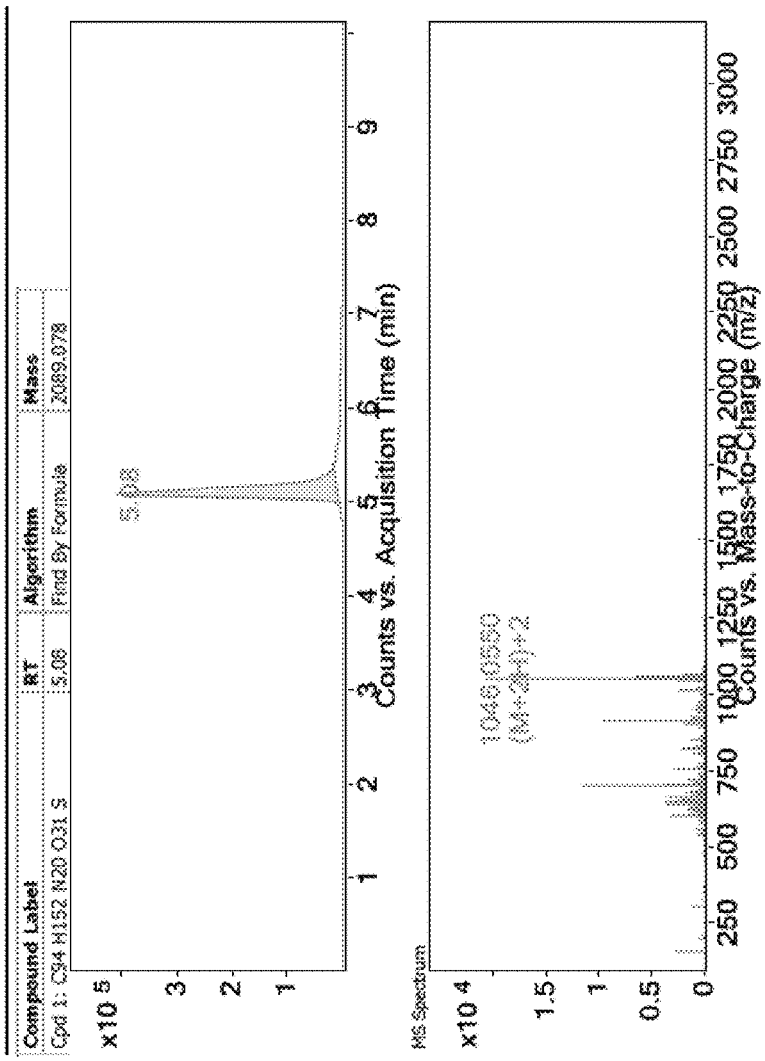
FIG. 38 shows the LC-MS profile of the O-Allyl Tn on the C-terminal peptide

FIG. 38 shows the LC-MS profile of the O-Allyl Tn on the C-terminal peptide

Example 25: Conjugation of O-Allyl-Tn to Peptide Cys-(Tn)-dTT831-844-βAla by Thiol-Ene Photoreaction Procedure A:

To a solution of peptide Cys-(Tn)-dTT831-844-βAla (FIG. 33) in water (2 mL, 0.482 mM) was added a solution of Tn in H$_2$O (100 µL, 0.1M, 10 equiv) and a catalytic amount of AAPH in UV cuvette. The mixture was stirred at room temperature under 365 nm irradiation for 60 min Ellman's test showed the reaction to be finished in 45 min. The solution was then lyophilized to afford the white power and LC-MS showed the presence of desired peptide-Tn conjugate LC-MS: [M] calcd for $C_{94}H_{152}O_{31}N_{20}S$, 2089.0653. found, 2089.0719. CAN/$H_2O$ 5 to 95% 5.11 min.

Procedure B:

Cys-(Tn)-dTT831-844-βAla (FIG. 33) To a solution of peptide in methanol (2 mL, 0.482 mM) was added a solution of Tn in $H_2O$ (100 μL, 0.1M, 10 equiv) and a catalytic amount of DMPA in UV cuvette. The mixture was stirred at room temperature under 365 nm irradiation for 60 min Ellman's test showed the reaction to be finished in 45 min. The solution was then lyophilized to afford the white power and LC-MS showed the presence of desired peptide-Tn. LC-MS: [M] calcd for $C_{94}H_{152}O_{31}N_{20}S$, 2089.0653. found, 2089.0817. CAN/$H_2O$ 5 to 95% 5.10 min.

Figure 39:
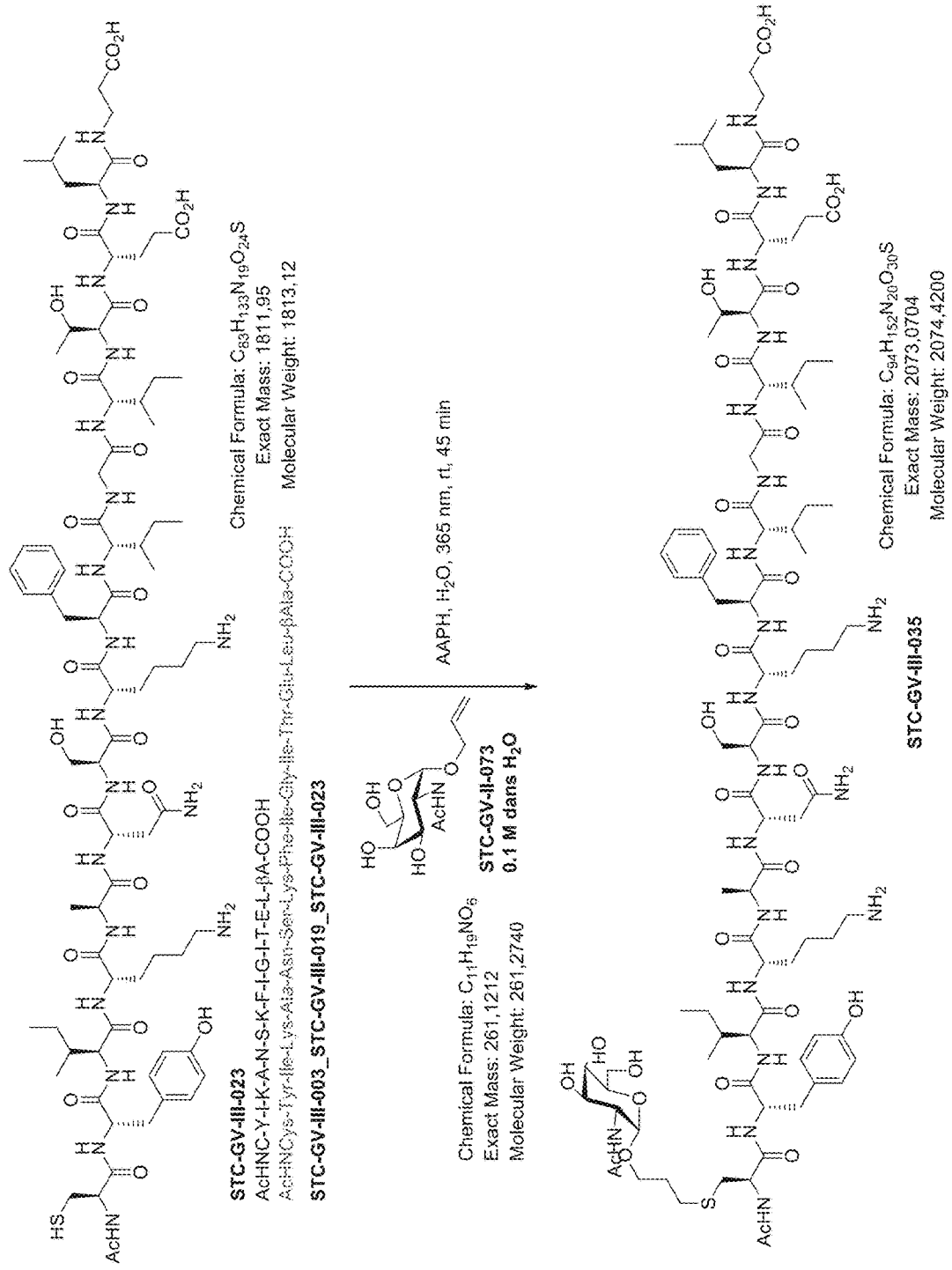
FIG. 39 shows the photolytic AAPH-catalyzed thiol-ene reaction of the O-Allyl Tn on the N-terminal peptide Cys-dTT831-844-βAla.

FIG. 39 shows the photolytic AAPH-catalyzed thiol-ene reaction of the O-Allyl Tn on the N-terminal peptide Cys-dTT831-844-βAla.

FIG. 40 shows the detailed LC-MS profile of the O-Allyl Tn on the N-terminal peptide.

REFERENCES

Cipolla et al., "Stereoselective synthesis of α-C-glycosides of N-acetylgalactosamine", *Tetrahedron Asymm.* (2000), 11: 295-303.

Cui et al., "Stereocontrolled allylation of 2-amino-2-deoxy sugar derivatives by a free-radical procedure", *Carbohydr. Res.*, (1998), 309: 319-330.

Danishefsky et al., "Development of Globo-H Cancer Vaccine", *Acc. Chem Res.*, (2015), 48(3): 643-652.

Demian et al., "Direct targeted glycation of the free sulfhydryl group of cysteine residue (Cys-34) of BSA. Mapping of the glycation sites of the anti-tumor Thomsen-Friedenreich neoglycoconjugate vaccine prepared by Michael addition reaction," *J. Mass Spectrom.*, (2014), 49: 1223-1233.

Dondoni et al., "A new ligation strategy for peptide and protein glycosylation: Photoinduced thiol-ene coupling", *Chem. Eur. J.*, (2009), 15: 11444-11449.

Dondoni et al., "Recent applications in thiol-ene coupling as a click process for glycoconjugation", *Chem. Soc. Rev.*, (2012), 41: 573-586.

Feng et al., "Chemo-enzymatic synthesis of fluorinated 2-N-acetamidosugar nucleotides using UDP-GlcNAc pyrophosphorylase", *Org. Biomol. Chem.* (2004), 2: 1617-1623.

Heimburg et al., "Inhibition of spontaneous breast cancer metastasis by anti-Thomsen-Friedenreich antigen monoclonal antibody JAA-F11.", *Neoplasia*, (2006) 8(11): 939-48.

Knapp et al., "Synthesis of α-GalNAc Thioconjugates from an α-GalNAc Mercaptan", *J. Org. Chem.* (2002), 67: 2995-2999.

Papadopoulos, "Diazo transfer and click chemistry in the solid phase syntheses of lysine-based glycodendrimers as antagonists against *Escherichia coli* FimH." *Molecular Pharmaceutics* (2012), 9(3): 394-403.

Rittenhouse-Diakun et al., "Development and characterization of monoclonal antibody to T-antigen: (gal beta1-3GalNAc-alpha-O)", *Hybridoma*, (1998), 17: 165-173.

Tati et al., "Humanization of JAA-F11, a Highly Specific Anti-Thomsen-Friedenreich Pancarcinoma Antibody and InVitro Efficacy Analysis.", *Neoplasia*, (2017), 19(9): 716-733.

The invention claimed is:

1. A method for producing a glycoconjugate immunogen, the method comprising:
   (a) providing a water-soluble carbohydrate antigen covalently linked to a terminal alkene (alkenyl carbohydrate antigen), the terminal alkene being directly conjugatable to a thiol group via a thiol-ene reaction and wherein the alkenyl carbohydrate antigen is an unprotected, water-soluble alkenyl carbohydrate antigen;
   (b) providing a carrier protein having one or more free thiol groups; and
   (c) performing a photocatalytic thiol-ene reaction to directly conjugate the carbohydrate antigen to the carrier protein at the one or more free thiol groups, thereby producing the glycoconjugate immunogen;
   wherein the carrier protein is immunogenic when administered to a subject, and wherein conjugation of the carbohydrate antigen to the carrier protein increases the immunogenicity of the carbohydrate antigen upon administration to the subject, as compared to administration of the unconjugated carbohydrate antigen.

2. The method of claim 1, wherein said photocatalytic thiol-ene reaction is performed under reaction conditions that avoid carrier protein denaturation, and/or that retain the carrier protein's activity, antigenicity, and/or structure.

3. The method of claim 1, wherein said photocatalytic thiol-ene reaction is performed in the presence of an organic solvent at a concentration sufficiently low to avoid carrier protein denaturation, or in the absence of any organic solvent.

4. The method of claim 1, wherein said photocatalytic thiol-ene reaction is performed in the presence of a water-soluble catalyst.

5. The method of claim 4, wherein the water-soluble catalyst is a free radical-generating azo compound, 2,2'-azobis[2-(2-imidazolin-2-yl)propane]dihydrochloride (Vazo 44 or VA-044); 2,2'-azobis(2-amidinopropane) dihydrochloride (AAPH); metals or metal ions having photoinitiator activity; a peroxide; tert-butyl hydroperoxide; benzoylperoxide; ammonium persulfate; or any derivative thereof having photoinitiator activity.

6. The method of claim 1, wherein said photocatalytic thiol-ene reaction is performed in the presence of a water-insoluble catalyst.

7. The method of claim 6, wherein the water-insoluble catalyst is a free radical-generating azo compound, 2,2-dimethoxy-2-phenylacetophenone (DMPA), azobisisobutyronitrile (AIBN), 2,2'-azobis(2-methylpropionitrile), 4,4'-Azobis(4-cyanopentanoic acid) (ACVA), 1,1'-azobis (cyanocyclohexane) (ACHN), diazenedicarboxylic acid bis (N,N-dimethylamide) (TMAD); azodicarboxylic acid dipiperidide (ADD), or any derivative thereof having photoinitiator activity.

8. The method of claim 1, wherein said photocatalytic thiol-ene reaction comprises irradiation under ultraviolet light.

9. The method of claim 1, wherein said photocatalytic thiol-ene reaction comprises reacting between 1 to 200 molar equivalents of the alkenyl carbohydrate antigen per free thiol group of the carrier protein.

10. The method of claim 1, wherein said photocatalytic thiol-ene reaction is performed at a pH that avoids carrier protein denaturation.

11. The method of claim 1, wherein said carbohydrate antigen, following conjugation to the carrier protein, is not cleavable from the carrier protein by an endogenous enzyme of the subject.

12. The method of claim 1, wherein said alkenyl carbohydrate antigen is covalently linked to the terminal alkene, and/or the carbohydrate antigen is conjugated to the carrier protein, via an O-glycosidic bond, an S-glycosidic bond, an N-glycosidic bond, or a C-glycosidic bond, or a bond obtained by reductive amination between an allyl amine and a reducing sugar.

13. The method of claim 1, wherein the carbohydrate antigen is or comprises a tumor associated carbohydrate antigen (TACA), or a viral polysaccharide antigen, or a bacterial capsular polysaccharide (CPS).

14. The method of claim 13, wherein the TACA is, is from, or comprises: Tn, S-Tn, Thomsen-Friedenreich (TF), (2,3)-S-TF, (2,6)-S-TF, Globo H, GD2, GD3, GM2, GM3, N-glycolyl-GM3, Lea, sLea, Lex, sLex, or any combination thereof; and wherein the bacterial CPS is, is from, or comprises a Pneumococcal and/or Streptococcal polysaccharide serotype, meningococcal CPS, or influenza CPS.

15. The method of claim 1, wherein said photocatalytic thiol-ene reaction conjugates more than one type of carbohydrate antigen to the carrier protein.

16. The method of claim 1, wherein the carbohydrate antigen in (a) is linked to the terminal alkene via a linker.

17. The method of claim 1, wherein the carrier protein provided in step (b) is:
   (i) a carrier protein comprising one or more cysteine residues having the one or more free thiol groups,
   (ii) a carrier protein engineered to add one or more further cysteine residues at a solvent-accessible position of the carrier protein;
   (iii) a carrier protein treated with a thiolating agent;
   (iv) a carrier protein treated with a reducing agent; or
   (v) any combination of (i) to (iv).

18. The method of claim 1, wherein the carrier protein is, is from, or comprises: Tetanus Toxoid (TT), Diphtheria Toxoid (DT), cross-reacting material 197 (CRM197), Meningococcal Outer Membrane Protein Complex (OMPC), H. influenzae Protein D (HiD), a cytokine, an immunogenic peptide, Tetanus Toxin 831-844 (SEQ ID NO: 1 or 2), albumin, or an immunogenic fragment thereof.

19. A method for producing a glycoconjugate vaccine or an adaptive immune response-triggering composition, the method comprising formulating the glycoconjugate immunogen prepared by the method of claim 1 with a pharmaceutically acceptable excipient, and/or an adjuvant.

20. A synthetic glycoconjugate immunogen prepared by the method of claim 1, comprising one or more carbohydrate antigens and an immunogenic carrier protein having one or more solvent-accessible cysteine residues, wherein the one or more carbohydrate antigens are linked to the immunogenic carrier protein at the one or more solvent-accessible cysteine residues, and wherein conjugation of the one or more carbohydrate antigens to the immunogenic carrier protein increases the immunogenicity of the one or more carbohydrate antigens upon administration to a subject, as compared to administration of the unconjugated carbohydrate antigen.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: Clostridium tetani

<400> SEQUENCE: 1

Tyr Ile Lys Ala Asn Ser Lys Phe Ile Gly Ile Thr Glu Leu
1               5                   10

<210> SEQ ID NO 2
<211> LENGTH: 16
<212> TYPE: PRT
<213> ORGANISM: Artificial Sequence
<220> FEATURE:
<223> OTHER INFORMATION: dTT831-844-Cys-beta-Ala
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: bAla

<400> SEQUENCE: 2

Tyr Ile Lys Ala Asn Ser Lys Phe Ile Gly Ile Thr Glu Leu Cys Ala
1               5                   10                  15
```